(12) United States Patent
Huigens, III et al.

(10) Patent No.: US 11,008,290 B2
(45) Date of Patent: May 18, 2021

(54) HALOGENATED QUINOLINE DERIVATIVES AS ANTIMICROBIAL AGENTS

(71) Applicant: University of Florida Research Foundation, Incorporated, Gainesville, FL (US)

(72) Inventors: Robert William Huigens, III, Williston, FL (US); Akash Basak, South Bend, IN (US); Yasmeen Abouelhassan, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 15/762,456

(22) PCT Filed: Sep. 23, 2016

(86) PCT No.: PCT/US2016/053295
§ 371 (c)(1),
(2) Date: Mar. 22, 2018

(87) PCT Pub. No.: WO2017/053696
PCT Pub. Date: Mar. 30, 2017

(65) Prior Publication Data
US 2018/0265475 A1     Sep. 20, 2018

Related U.S. Application Data

(60) Provisional application No. 62/301,594, filed on Feb. 29, 2016, provisional application No. 62/232,362, filed on Sep. 24, 2015.

(51) Int. Cl.
| C07D 215/48 | (2006.01) |
| C07D 215/04 | (2006.01) |
| C07D 215/12 | (2006.01) |
| C07D 215/14 | (2006.01) |
| C07D 215/28 | (2006.01) |
| A61K 31/47 | (2006.01) |
| A61P 31/04 | (2006.01) |
| A61K 45/06 | (2006.01) |
| C07D 215/38 | (2006.01) |

(52) U.S. Cl.
CPC ............ C07D 215/48 (2013.01); A61K 31/47 (2013.01); A61K 45/06 (2013.01); A61P 31/04 (2018.01); C07D 215/04 (2013.01); C07D 215/12 (2013.01); C07D 215/14 (2013.01); C07D 215/28 (2013.01); C07D 215/38 (2013.01)

(58) Field of Classification Search
CPC .. C07D 215/48; C07D 215/04; C07D 215/12; C07D 215/14
See application file for complete search history.

(56) References Cited

U.S. PATENT DOCUMENTS

| 3,910,925 A * | 10/1975 | Kreider ................ C07D 401/12 546/153 |
| 2009/0227626 A1* | 9/2009 | Deraeve ............... C07D 215/40 514/313 |
| 2010/0144693 A1* | 6/2010 | Bush .................. A61K 31/4375 514/186 |
| 2012/0165370 A1* | 6/2012 | Tang .................... C07D 215/14 514/312 |
| 2014/0336221 A1 | 11/2014 | Pegan et al. |

FOREIGN PATENT DOCUMENTS

WO     WO 2015/100331 A2     7/2015

OTHER PUBLICATIONS

Hassani et al. J. Med. Chem. 2005, 48, 7733-7749 (Year: 2005).*

(Continued)

*Primary Examiner* — Matthew P Coughlin
(74) *Attorney, Agent, or Firm* — Wolf, Greenfield & Sacks, P.C.

(57) ABSTRACT

The present invention provides halogenated quinoline derivatives, such as compounds of Formula (I) or (I'), and pharmaceutically acceptable salts thereof, and methods of preparing the halogenated quinoline derivatives. The halogenated quinoline derivatives are expected to be antimicrobial agents and may act through an iron(II)-dependent mode of action. The present invention also provides pharmaceutical compositions, kits, uses, and methods that involve the halogenated quinoline derivatives and may be useful in preventing or treating a microbial infection (e.g., a bacterial infection) in a subject, inhibiting the growth and/or reproduction of a microorganism (e.g., a bacterium), killing a microorganism (e.g., a bacterium), inhibiting the formation and/or growth of a biofilm, reducing or removing a biofilm, and/or disinfecting a surface.

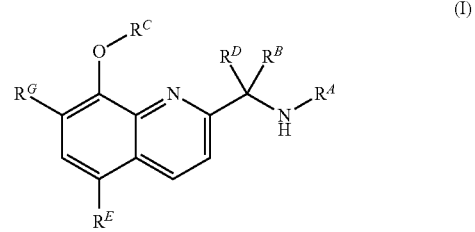

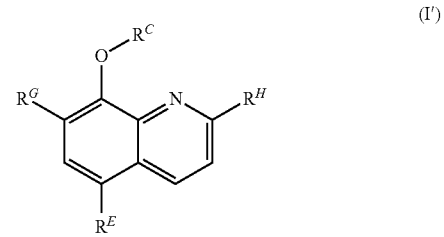

28 Claims, 12 Drawing Sheets

(56) References Cited

OTHER PUBLICATIONS

Ex parte Cao, Decision rendered by the Board of Patent Appeals and Interferences in U.S. Appl. No. 10/696,862 on Sep. 21, 2011 (Year: 2011).*
Albrecht et al. Eur. J. Org. Chem. 2007, 2850-2858 (Year: 2007).*
Vaidya et al. Journal of Medicinal & Pharmaceutical Chemistry 1962, 5, 389-397 (Year: 1962).*
Invitation to Pay Additional Fees for PCT/US2016/053295, mailed Mar. 27, 2017.
International Search Report and Written Opinion for PCT/US2016/053295, dated Jun. 9, 2017.
International Preliminary Report on Patentability for PCT/US2016/053295, dated Apr. 5, 2018.
[No Author Listed] PubChem SID No. 141693651 dated Aug. 20, 2012.
Abouelhassan et al., Discovery of quinoline small molecules with potent dispersal activity against methicillin-resistant *Staphylococcus aureus* and *Staphylococcus epidermidis* biofilms using a scaffold hopping strategy. Bioorg Med Chem Lett. Nov. 1, 2014;24(21):5076-80. doi: 10.1016/j.bmcl.2014.09.009. Epub Sep. 15, 2014.
Almohamad et al., Influence of isolate origin and presence of various genes on biofilm formation by Enterococcus faecium. FEMS Microbiology Letters, 2014;353 (2): 151-156. https://doi.org/10.1111/1574-6968.12418.
Archer et al., *Staphylococcus aureus* biofilms: properties, regulation, and roles in human disease. Virulence. Sep.-Oct. 2011;2(5):445-59. doi: 10.4161/viru.2.5.17724. Epub Sep. 1, 2011.
Basak et al., Halogenated quinolines discovered through reductive amination with potent eradication activities against MRSA, MRSE and VRE biofilms. Org. Biomol. Chem., 2015;13:10290-10294. DOI: 10.1039/C5OB01883H.
Basak et al., Synthetically Tuning the 2-Position of Halogenated Quinolines: Optimizing Antibacterial and Biofilm Eradication Activities via Alkylation and Reductive Amination Pathways. Chemistry. Jun. 27, 2016;22(27):9181-9. doi: 10.1002/chem.201600926. Epub Jun. 1, 2016.
Camilli et al., Bacterial Small-Molecule Signaling Pathways. Science. Feb. 24, 2006;311(5764):1113-6.
Chambers et al., Waves of resistance: *Staphylococcus aureus* in the antibiotic era. Nat Rev Microbiol. Sep. 2009;7(9):629-41. doi: 10.1038/nrmicro2200.
Davies et al., Understanding biofilm resistance to antibacterial agents. Nat Rev Drug Discov. Feb. 2003;2(2):114-22.
Donlan et al., Biofilms: survival mechanisms of clinically relevant microorganisms. Clin Microbiol Rev. Apr. 2002;15(2):167-93.
Fletcher et al., Draining the moat: disrupting bacterial biofilms with natural products. Tetrahedron 2014;70(37):6373-6383.
Garrison et al., Bromophenazine derivatives with potent inhibition, dispersion and eradication activities against *Staphylococcus aureus* biofilms. RSC Adv., 2015;5:1120-1124. DOI: 10.1039/C4RA08728C.
Geske et al., Small Molecule Inhibitors of Bacterial Quorum Sensing and Biofilm Formation. J. Am. Chem. Soc., 2005;127(37):12762-12763. DOI: 10.1021/ja0530321.
Heim et al., A mouse model of *Staphylococcus* catheter-associated biofilm infection. Methods in Molecular Biology Jan. 2014;1106:183-191. DOI: 10.1007/978-1-62703-736-5_17.
Hirt et al., Antimicrobial Peptide GL13K Is Effective in Reducing Biofilms of Pseudomonas aeruginosa. Antimicrob. Agents Chemother. Oct. 2013;57(10):4903-4910.
Hoque et al., Membrane Active Small Molecules Show Selective Broad Spectrum Antibacterial Activity with No Detectable Resistance and Eradicate Biofilms. J. Med. Chem., 2015;58(14):5486-5500. DOI: 10.1021/acs.jmedchem.5b00443.
Miller et al., Quorum sensing in bacteria. Annu Rev Microbiol. 2001;55:165-99.
Musk et al., Chemical countermeasures for the control of bacterial biofilms: effective compounds and promising targets. Curr Med Chem. 2006;13(18):2163-77.
Ng et al., Bacterial quorum-sensing network architectures. Annu Rev Genet. 2009;43:197-222. doi: 10.1146/annurev-genet-102108-134304.
Otto et al., Staphylococcal biofilms. Curr Top Microbiol Immunol. 2008;322:207-28.
Rabin et al., Agents that inhibit bacterial biofilm formation. Future Med Chem. 2015;7(5):647-71. doi: 10.4155/fmc.15.7.
Snowden et al., Biofilm-Infected Intracerebroventricular Shunts Elicit Inflammation within the Central Nervous System. Infect. Immun. Sep. 2012;80(9):3206-3214.
Uckay et al., Foreign body infections due to *Staphylococcus epidermidis*. Ann Med. 2009;41(2):109-19. doi: 10.1080/07853890802337045.
Zoysa et al., Antimicrobial Peptides with Potential for Biofilm Eradication: Synthesis and Structure Activity Relationship Studies of Battacin Peptides. J. Med. Chem., 2015;58(2):625-639. DOI: 10.1021/jm501084q.

* cited by examiner

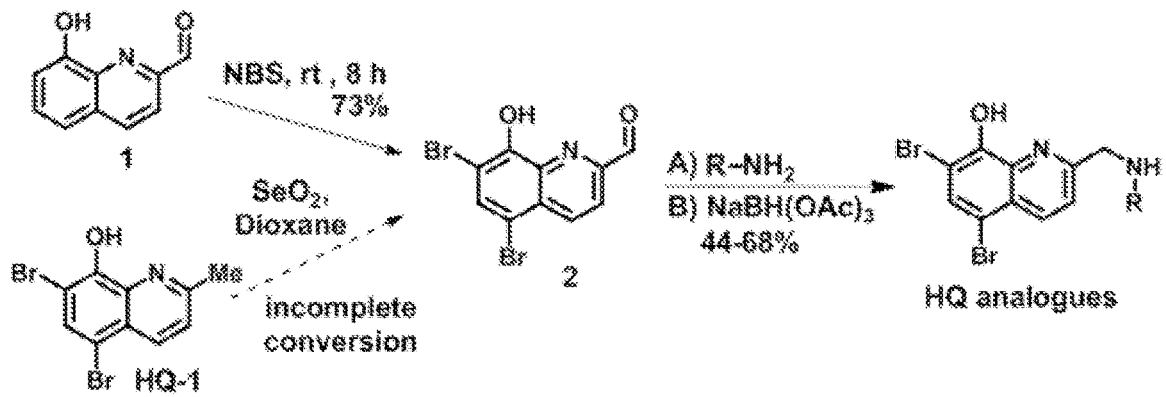
Figure 2A
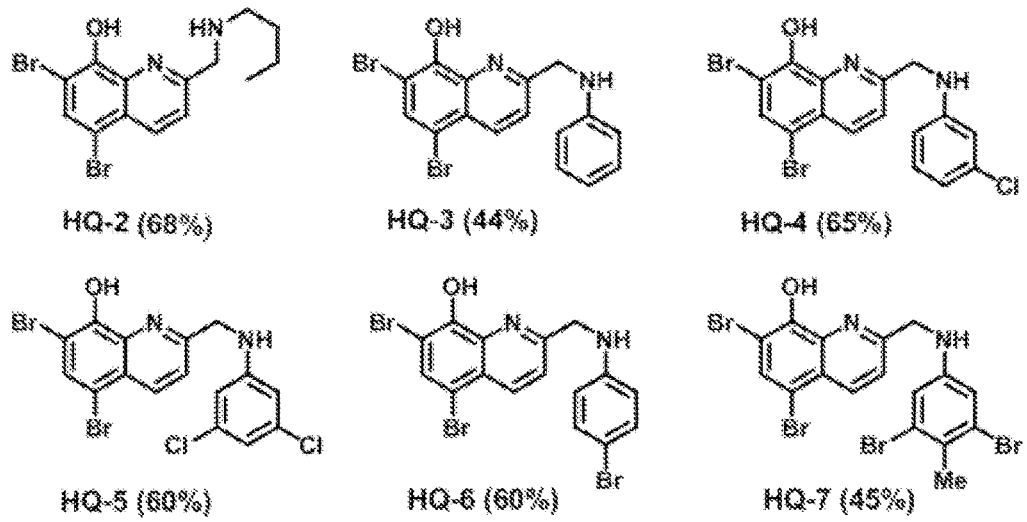
Figure 2B
Figure 2C

HALOGENATED QUINOLINE DERIVATIVES AS ANTIMICROBIAL AGENTS

RELATED APPLICATIONS

The present application is a national stage filing under 35 U.S.C. § 371 of international PCT application, PCT/US2016/053295, filed Sep. 23, 2016, which claims priority under 35 U.S.C. § 119(e) to U.S. provisional patent applications, U.S. Ser. No. 62/301,594, filed Feb. 29, 2016, and U.S. Ser. No. 62/232,362, filed Sep. 24, 2015, each of which is incorporated herein by reference.

BACKGROUND OF THE INVENTION

The arsenal of antibiotics was discovered as growth inhibiting agents against rapidly-dividing bacteria; however, non-replicating bacteria that reside within surface-attached biofilms have proven difficult, if not impossible, to eradicate with current therapeutic options.[1-4] Biofilms occur in ~80% of bacterial infections as biofilm-associated infections are prevalent in both community- and hospital-acquired infections (HAIs).[4,5] Bacteria that live inside a biofilm are encased within a protective matrix of biomolecules and display contrasting gene expressing profiles, physiologies and greatly reduced growth-rates compared to their planktonic counterparts.[1,2,5] In addition, bacterial biofilms house persister cells, which are metabolically dormant, non-replicating cells that display antibiotic-tolerance significantly contributing to chronic and recurring bacterial infection.[6,7]

Several major gram-positive pathogens are involved in biofilm-associated HAIs, which are responsible for ~100,000 deaths each year in the United States.[8] Staphylococcal pathogens, in particular *S. aureus* and *S. epidermidis*, are the leading cause of biofilm-associated HAIs, including indwelling medical device/implant infections (e.g., hip joint replacements).[9] *S. epidermidis* is also known for playing a major role in biofilm-associated cerebral shunt[10] and catheter[11] infections. *Enterococcus faecium*, the causative agent in VRE (vancomycin-resistant *E. faecium*), is another major pathogen involved in a multitude of biofilm-associated bacterial infections, including: endocarditis, catheter-associated urinary tract infections and peridontitis.[12]

In recent years, there has been significant interest in the identification of biofilm inhibitors and biofilm dispersal agents that operate via the control of quorum sensing[13] (the communication system bacteria use to govern biofilm processes)[14] and other non-growth inhibiting mechanisms to address biofilm-associated problems.[15] Biofilm inhibitors and dispersal agents are indeed important; however, biofilm-eradication is a distinct phenotype that involves the killing of biofilm cells[16,17] and has potential to be standalone antibiofilm therapies.

Antimicrobial peptides (AMPs)[18-20] and mimics[21] are the most well-known biofilm-eradicating agents. AMPs are naturally occurring peptides used in host immune or general defense responses to bacterial infection and operate through the destruction of bacterial membranes causing cell lysis and death.[18-21] The challenge in developing AMP-based therapeutics that are safe in humans is the identification of agents that selectively target and lyse bacterial cell membranes and not mammalian cell membranes. New biofilm-eradicating agents that operate through alternative mechanisms are of great importance to human health and could lead to effective treatments for biofilm-associated infections.

SUMMARY OF THE INVENTION

In one aspect, the present invention provides halogenated quinoline derivatives (HQs, HQ compounds, HQ analogues), such as compounds of Formula (I'), and salts, hydrates, solvates, polymorphs, co-crystals, tautomers, stereoisomers, isotopically labeled derivatives, prodrugs, thereof:

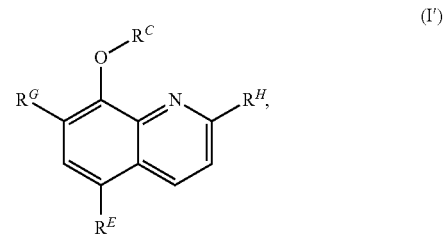

(I')

wherein $R^C$, $R^E$, $R^G$, $R^H$ are as described herein.

In certain embodiments, the present invention provides halogenated quinoline derivatives (HQs, HQ compounds, HQ analogues), such as compounds of Formula (I), and salts, hydrates, solvates, polymorphs, co-crystals, tautomers, stereoisomers, isotopically labeled derivatives, prodrugs, thereof:

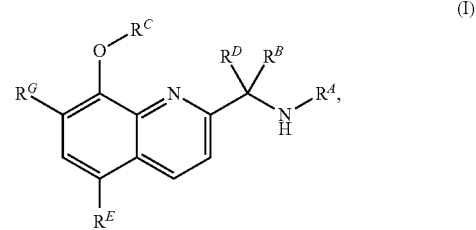

(I)

wherein $R^A$, $R^B$, $R^D$, $R^C$, $R^E$, and $R^G$ are as described herein. In certain embodiments, the compound of the invention is not of the formula:

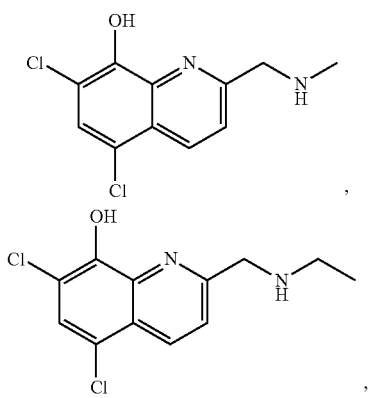

or a pharmaceutically acceptable salt thereof.

Exemplary compounds of the invention include, but are not limited to:

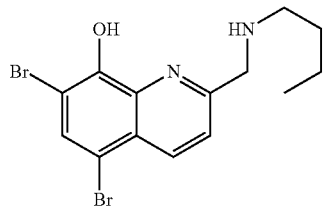

and pharmaceutically acceptable salts, solvates, hydrates, polymorphs, co-crystals, tautomers, stereoisomers, isotopically labeled derivatives, and prodrugs thereof.

Exemplary compounds of the invention also include, but are not limited to:

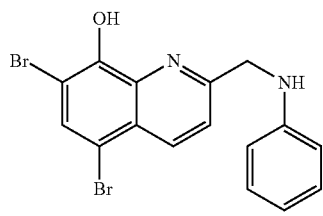

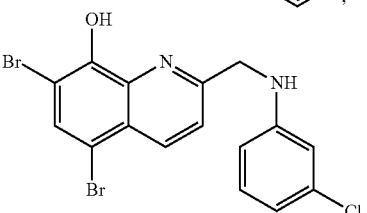

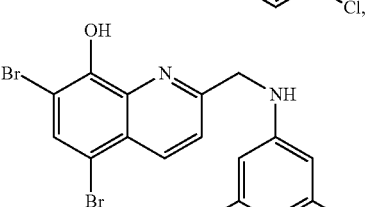

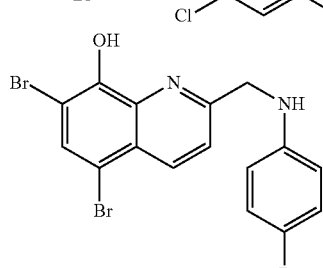

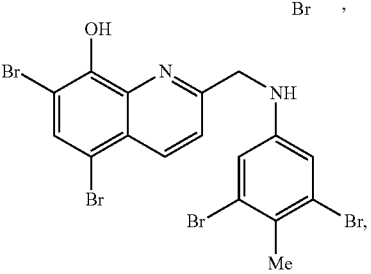

and pharmaceutically acceptable salts, solvates, hydrates, polymorphs, co-crystals, tautomers, stereoisomers, isotopically labeled derivatives, and prodrugs thereof.

Exemplary compounds of the invention also include, but are not limited to:

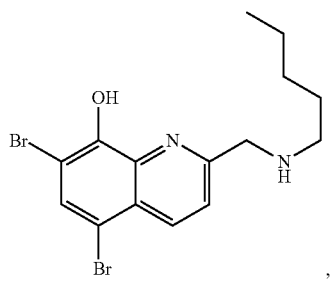

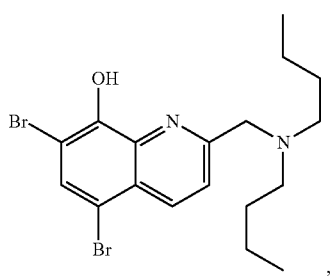

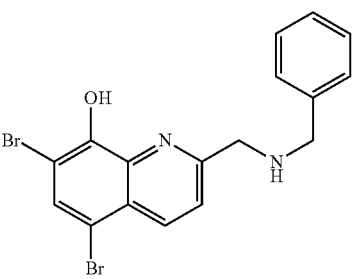

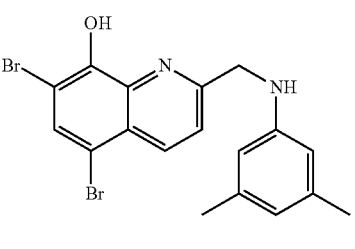

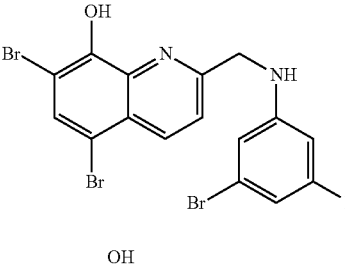

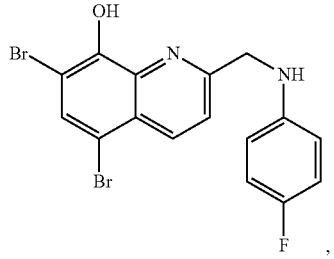

-continued
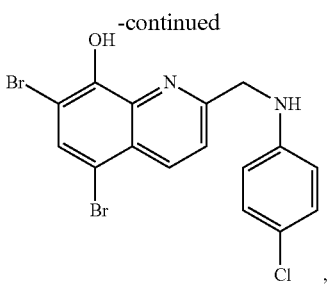
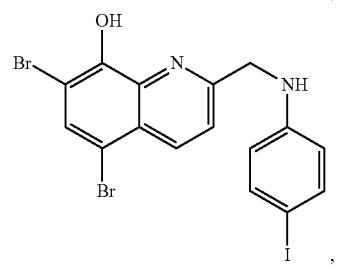
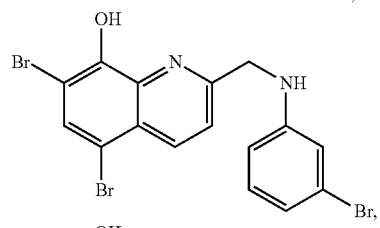
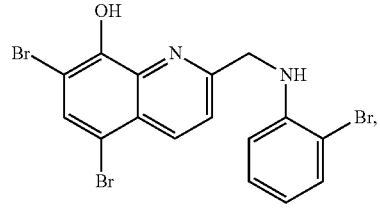
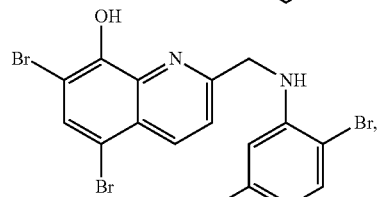
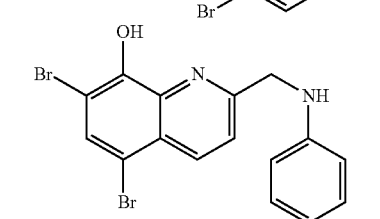
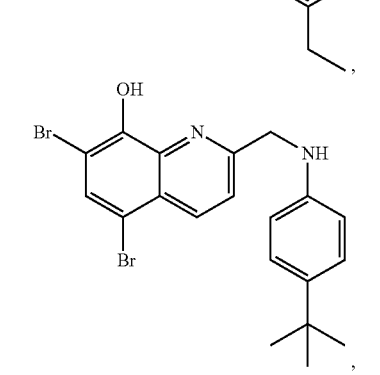
-continued
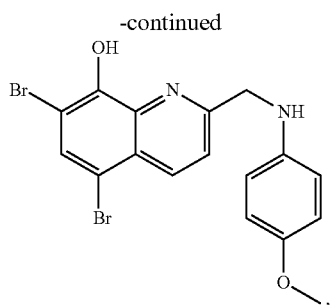
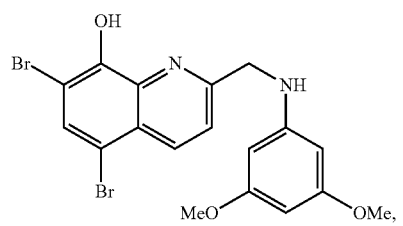
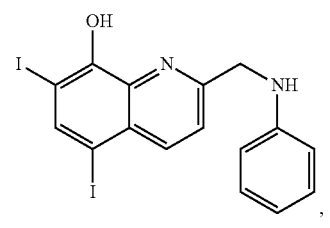
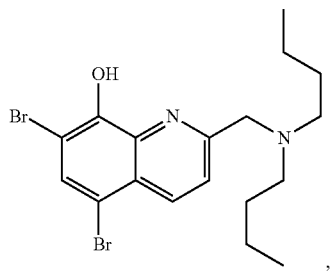
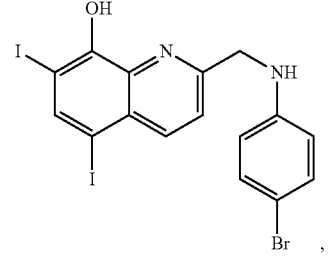
and pharmaceutically acceptable salts, solvates, hydrates, polymorphs, co-crystals, tautomers, stereoisomers, isotopically labeled derivatives, and prodrugs thereof.
Exemplary compounds of the invention also include, but are not limited to:
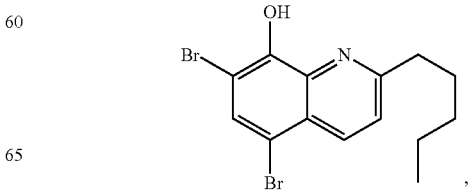

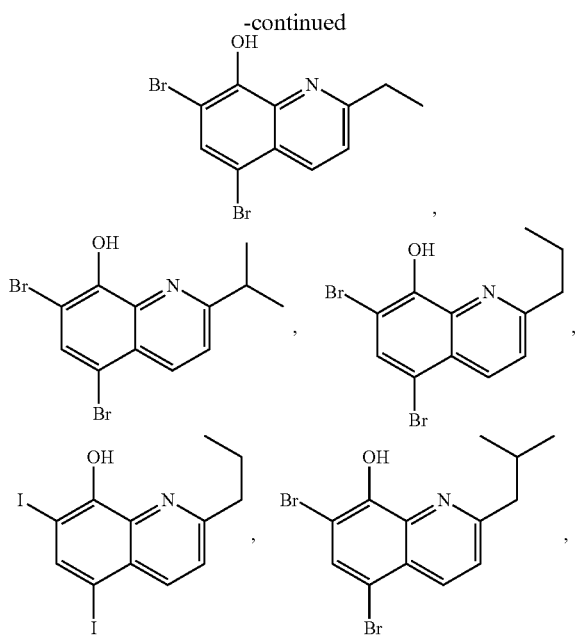

and pharmaceutically acceptable salts, solvates, hydrates, polymorphs, co-crystals, tautomers, stereoisomers, isotopically labeled derivatives, and prodrugs thereof.

Exemplary compounds of the invention also include, but are not limited to:

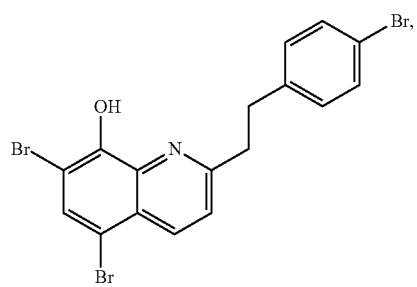 [SMILES: Oc1c(Br)cc(Br)c2ccc(CCc3ccc(Br)cc3)nc12]

and pharmaceutically acceptable salts, solvates, hydrates, polymorphs, co-crystals, tautomers, stereoisomers, isotopically labeled derivatives, and prodrugs thereof.

Exemplary compounds of the invention also include, but are not limited to:

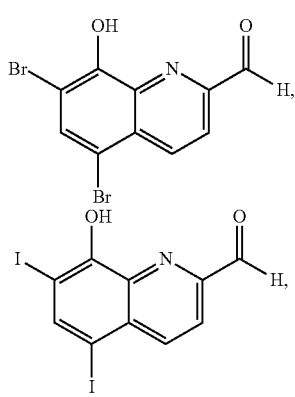

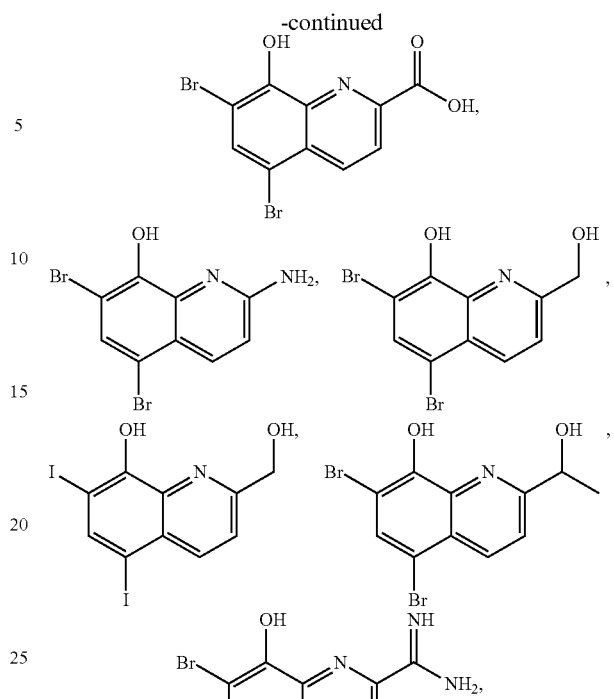

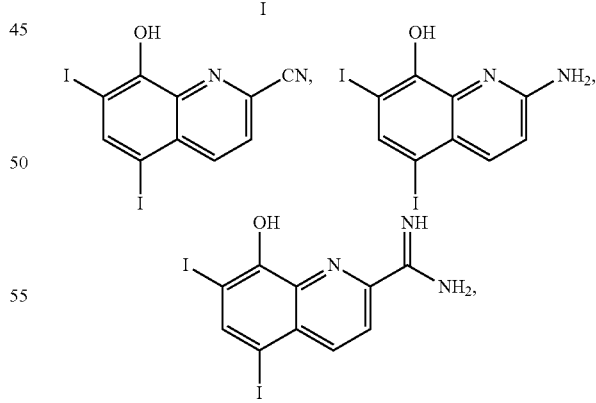

and pharmaceutically acceptable salts, solvates, hydrates, polymorphs, co-crystals, tautomers, stereoisomers, isotopically labeled derivatives, and prodrugs thereof.

The compounds of the invention may exhibit antimicrobial activity (e.g., antibacterial activity, such as antibacterial activity against strains of *Staphylococcus aureus* (e.g., methicillin-resistant strains of *Staphylococcus aureus*

(MRSA)), strains of *Staphylococcus epidermidis* (e.g., methicillin-resistant strains of *Staphylococcus epidermidis* (MRSE)), and strains of *Enterococcus faecium* (e.g., vancomycin-resistant strains of *Enterococcus faecium* (VRE))). The inventive compounds may be able to reduce, inhibit, and/or remove biofilms (e.g., *Staphylococcus aureus* biofilms (e.g., methicillin-resistant *Staphylococcus aureus* biofilms), *Enterococcus faecium* biofilms (e.g., vancomycin-resistant *Enterococcus faecium* biofilms), and/or *Staphylococcus epidermidis* biofilms (e.g., methicillin-resistant *Staphylococcus epidermidis* biofilms)). Without wishing to be bound by any particular theory, the compounds of the invention may inhibit and/or kill a microorganism, and/or reduce or remove biofilms through a mechanism other than the destruction of microbial membranes, e.g., the compounds of the invention may inhibit and/or kill a microorganism, and/or reduce or remove a biofilm through an iron(II)-dependent mode of action. The inventive compounds may have minimal or no adverse side effects. In certain embodiments, the inventive compounds have low cytotoxicity with respect to mammalian cells and/or demonstrate low hemolysis activity.

In another aspect, the present invention provides methods of preparing the compounds of the invention. In certain embodiments, described herein are methods of preparing the compounds of Formula (I), and salts thereof (Method A), the methods including contacting a compound of Formula (B):

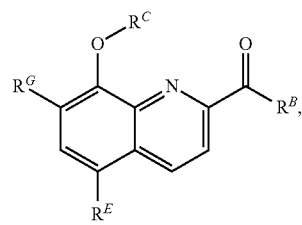

(B)

or a salt thereof, with an amine of Formula (C):

(C)

or a salt thereof, in the presence of a reductant to provide the compound of Formula (I), or salt thereof.

In certain embodiments, described herein are methods of preparing the compounds of Formula (I) (Method B), and salts thereof, the methods including contacting an imine of Formula (D):

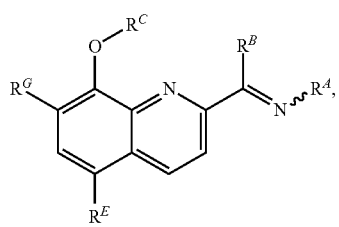

(D)

or a salt thereof, with a reductant to provide the compound of Formula (I), or salt thereof.

In certain embodiments, Method B further comprises contacting a compound of Formula (B):

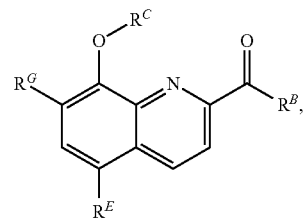

(B)

or a salt thereof, with an amine of Formula (C):

(C)

or a salt thereof, to provide the imine of Formula (D), or salt thereof.

In certain embodiments, Method A and/or Method B further comprise contacting a compound of Formula (A1):

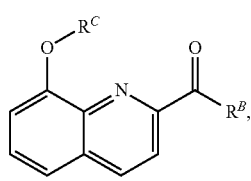

(A1)

or a salt thereof, with a halogenating agent to provide the compound of Formula (B), or salt thereof.

In certain embodiments, Method A and/or Method B further comprise contacting a compound of Formula (A2):

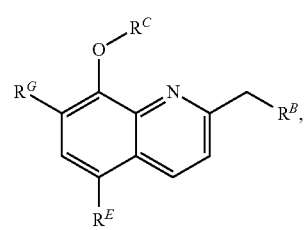

(A2)

or a salt thereof, with an oxidant to provide the compound of Formula (B), or salt thereof.

In another aspect, the present invention provides methods of preparing the compounds of the invention. In certain embodiments, described herein are methods of preparing the compounds of Formula (I'-b), and salts thereof (Method C):

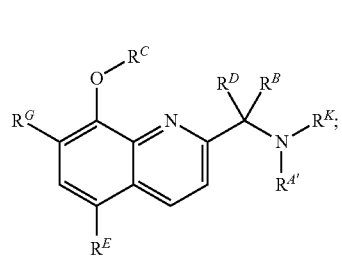

(I'-b)

the methods including contacting a compound of Formula (B):

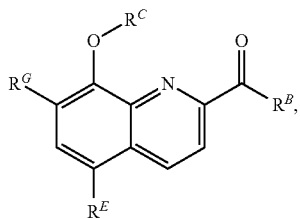

or a salt thereof, with an amine of Formula (E):

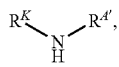

or a salt thereof, in the presence of a reductant to provide the compound of Formula (I'-b), or salt thereof.

In certain embodiments, described herein are methods of preparing the compounds of Formula (I'-b) (Method D), and salts thereof:

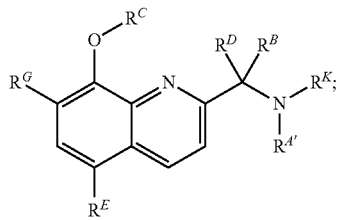

the methods including contacting an imine or iminium ion of Formula (F):

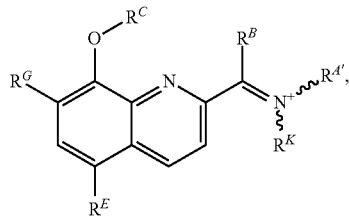

or a salt thereof, with a reductant to provide the compound of Formula (I'-b), or salt thereof.

In certain embodiments, Method D further comprises contacting a compound of Formula (B):

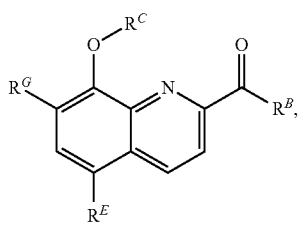

or a salt thereof, with an amine of Formula (E):

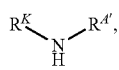

or a salt thereof, to provide the imine or iminium ion of Formula (F), or salt thereof.

In certain embodiments, Method C and/or Method D further comprise contacting a compound of Formula (A1):

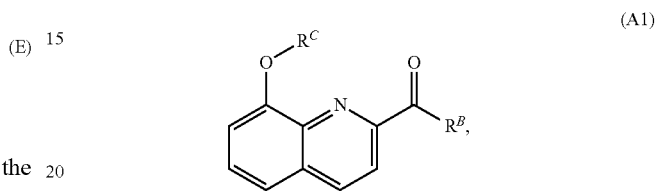

or a salt thereof, with a halogenating agent to provide the compound of Formula (B), or salt thereof.

In certain embodiments, Method C and/or Method D further comprise contacting a compound of Formula (A2):

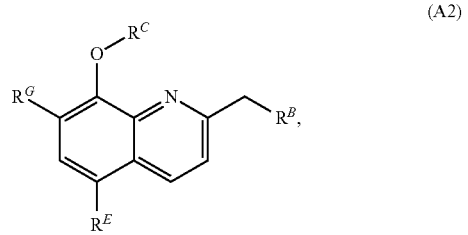

or a salt thereof, with an oxidant to provide the compound of Formula (B), or salt thereof.

In another aspect, the present invention provides methods of preparing the compounds of the invention. In certain embodiments, described herein are methods of preparing the compounds of Formula (G), and salts thereof (Method E):

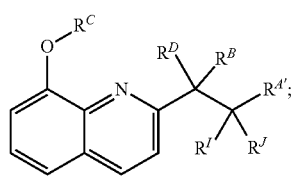

the methods including contacting a compound of Formula (H):

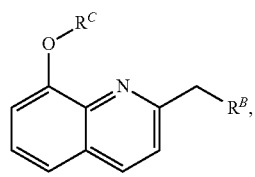

or a salt thereof, with a base and an halide of Formula (J):

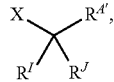

or a salt thereof, to provide the compound of Formula (G), or salt thereof.

In another aspect, the present invention provides methods of preparing the compounds of the invention. In certain embodiments, described herein are methods of preparing the compounds of Formula (G), and salts thereof (Method E):

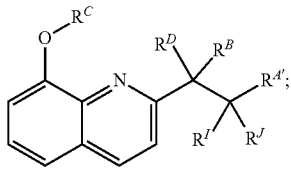

the methods including contacting a compound of Formula (H'):

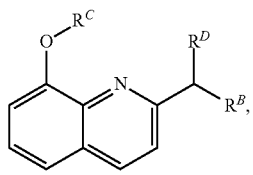

or a salt thereof, with a base and an halide of Formula (J):

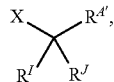

or a salt thereof, to provide the compound of Formula (G), or salt thereof.

In certain embodiments, Method E further comprises contacting a compound of Formula (G):

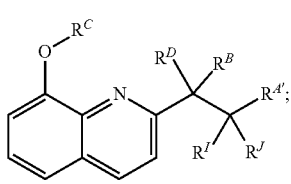

or a salt thereof, with a halogenating agent to provide the compound of Formula (I'-a):

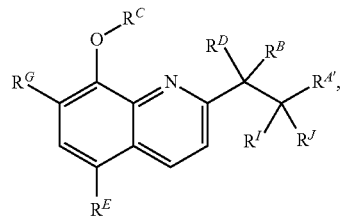

or salt thereof.

In another aspect, the present invention provides compositions including a compound of the invention and optionally an excipient. In certain embodiments, the composition includes an effective amount of the compound for disinfecting a surface. In certain embodiments, the composition is a pharmaceutical composition including a compound of the invention and optionally a pharmaceutically acceptable excipient. In certain embodiments, a pharmaceutical composition of the invention includes an effective amount of a compound of the invention for administration to a subject. In certain embodiments, the pharmaceutical composition is useful in a method of the invention (e.g., a method of treating a microbial infection, preventing a microbial infection, inhibiting the growth of a microorganism, inhibiting the reproduction of a microorganism, killing a microorganism, inhibiting the formation and/or growth of a biofilm, reducing or removing (e.g., eradicating) a biofilm, or disinfecting a surface). In certain embodiments, the microorganism is a bacterium. In certain embodiments, the bacterium is a Gram-positive bacterium (e.g., a *Staphylococcus* species or *Enterococcus* species). In certain embodiments, the bacterium is a Gram-negative bacterium (e.g., an *Acinetobacter* species). In certain embodiments, the microorganism is a *mycobacterium*.

Another aspect of the present invention relates to methods of treating and/or preventing a microbial infection in a subject in need thereof, the method including administering to the subject a therapeutically or prophylactically effective amount of a compound or pharmaceutical composition of the invention. In certain embodiments, the microbial infection is treated and/or prevented by the inventive methods. The microbial infections that may be treated and/or prevented by the inventive methods include, but are not limited to, microbial respiratory tract infections, microbial gastrointestinal tract infections, microbial urogenital tract infections, microbial bloodstream infections, microbial ear infections, microbial skin infections, microbial oral infections, microbial dental infections, microbial wound or surgical site infections, microbial infections associated with cystic fibrosis, and microbial infections associated with implanted devices. In certain embodiments, the microbial infection described herein is a bacterial infection. In certain embodiments, the bacterium causing the bacterial infections is a Gram-positive bacterium (e.g., a *Staphylococcus* species or *Enterococcus* species). In certain embodiments, the bacterium causing the bacterial infections is a Gram-negative bacterium (e.g., an *Acinetobacter* species). In certain embodiments, the subject is a human. In certain embodiments, the subject is a human with cystic fibrosis. In certain embodiments, the subject is a non-human animal.

In another aspect, the present invention provides methods of inhibiting the growth of a microorganism (e.g., a bacterium, *mycobacterium*, archaeon, protist, fungus, or parasite) in vitro or in vivo.

In yet another aspect, the present invention provides methods of inhibiting the reproduction of a microorganism (e.g., a bacterium, *mycobacterium*, archaeon, protist, fungus, or parasite) in vitro or in vivo.

In yet another aspect, the present invention provides methods of killing a microorganism (e.g., a bacterium, *mycobacterium*, archaeon, protist, fungus, or parasite) in intro or in vivo.

In certain embodiments, an inventive method includes contacting a microorganism (e.g., bacterium, *mycobacterium*, archaeon, protist, fungus, or parasite) with a compound or pharmaceutical composition of the invention in an amount effective at inhibiting the growth and/or reproduction of or killing the microorganism.

Another aspect of the invention relates to methods of inhibiting the formation and/or growth of, reducing, or removing a biofilm, the method including contacting the biofilm with an effective amount of a compound or pharmaceutical composition of the invention. In certain embodiments, the biofilm includes a microorganism (e.g., a bacterium, *mycobacterium*, archaeon, protist, fungus, or parasite). In certain embodiments, the biofilm includes bacteria. The biofilm may include one or more species of bacteria and/or other microorganisms.

Another aspect of the present invention relates to methods of disinfecting a surface, the methods including contacting the surface with an effective amount of a compound or composition of the invention. In certain embodiments, the surface is a biological surface (e.g., skin). In certain embodiments, the surface is a non-biological surface.

Another aspect of the present invention relates to kits comprising a container with a compound or composition (e.g., pharmaceutical composition) of the invention. The kits of the invention may include a single dose or multiple doses of the compound or pharmaceutical composition thereof. The provided kits may be useful in a method of the invention (e.g., a method of treating a microbial infection, preventing a microbial infection, inhibiting the growth of a microorganism (e.g., bacterium, *mycobacterium*, archaeon, protist, fungus, or parasite), inhibiting the reproduction of a microorganism, killing a microorganism, inhibiting the formation and/or growth of a biofilm, reducing or removing a biofilm, or disinfecting a surface). A kit of the invention may further include instructions for using the kit (e.g., instructions for using the compound or composition (e.g., pharmaceutical composition) included in the kit).

In another aspect, the present invention provides uses of the compounds and pharmaceutical compositions of the invention for manufacturing a medicament for treating and/or preventing a microbial infection.

In another aspect, the present invention provides the compounds and pharmaceutical compositions of the invention for use in methods of preventing and/or treating a microbial infection.

In another aspect, the present invention provides the compounds and pharmaceutical compositions of the invention for treating and/or preventing a microbial infection.

The present application refers to various issued patent, published patent applications, journal articles, and other publications, all of which are incorporated herein by reference. The details of one or more embodiments of the invention are set forth herein. Other features, objects, and advantages of the invention will be apparent from the Detailed Description, Figures, Examples, and Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and subrange within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" refers to alkyl, alkenyl, alkynyl, and carbocyclic groups. Likewise, the term "heteroaliphatic" as used herein, refers to heteroalkyl, heteroalkenyl, heteroalkynyl, and heterocyclic groups.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is substituted $C_{1-10}$ alkyl (such as substituted $C_{1-6}$ alkyl, e.g., —$CF_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C═C double bond for which the stereochemistry is not specified (e.g., —CH═$CHCH_3$ or

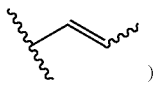
)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, aziridinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 p electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix -ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group) if not otherwise provided explicitly. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$R$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{aa}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ -C —C(=S)N($C_{1-6}$ alkyl)$_2$, —C(=S)NH($C_{1-6}$ alkyl), —C(=S)NH$_2$, —C(=O)S($C_{1-6}$ alkyl), —C(=S)S$C_{1-6}$ alkyl, —SC(=S) S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —ON($R^{bb}$)$_2$, —OC(=O) $SR^{aa}$, —OC(=O)$R^{aa}$, —OCO$_2R^{aa}$, —OC(=O)N($R^{bb}$)$_2$, —OC(=N$R^{bb}$)$R^{aa}$, —OC(=N$R^{bb}$)O$R^{aa}$, —OC(=N$R^{bb}$)N ($R^{bb}$)$_2$, —OS(=O)$R^{aa}$, —OSO$_2R^{aa}$, —OSi($R^{aa}$)$_3$, —OP ($R^{cc}$)$_2$, —OP($R^{cc}$)$_3^+X^-$, —OP(O$R^{cc}$)$_2$, —OP(O$R^{cc}$)$_3^+X^-$, —OP(=O)($R^{aa}$)$_2$, —OP(=O)(O$R^{cc}$)$_2$, and —OP(=O)(N ($R^{bb}$))$_2$, wherein $X^-$, $R^{aa}$, $R^{bb}$, and $R^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

"Acyl" refers to a moiety selected from the group consisting of —C(=O)$R^{aa}$, —CHO, —CO$_2R^{aa}$, —C(=O)N ($R^{bb}$)$_2$, —C(=N$R^{bb}$)$R^{aa}$, —C(=N$R^{bb}$)O$R^{aa}$, —C(=N$R^{bb}$) N($R^{bb}$)$_2$, —C(=O)N$R^{bb}$SO$_2R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —N($R^{cc}$)$_2$, —CN, —C(=O)$R^{aa}$, —C(=O)N ($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is a nitrogen protecting group (also referred to as an amino protecting group). Nitrogen protecting groups include, but are not limited to, —OH, —$OR^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N ($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O) (R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), tert-butoxycarbonyl, methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris (levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate, alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4{}^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I) or (I') may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound and wherein x is a number greater than 0. A given compound may form more than one type of hydrate, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2 $H_2O$) and hexahydrates (R.6 $H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-toimide, lactam-to-lactim, enamine-to-imine, and enamine-to-(a different enamine) tautomerizations.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Polymorph" refers to a particular polymorphic variant of a given compound. Polymorphism is the ability of a solid substance of a given chemical composition to exist in more than one form or crystalline structure. Polymorphism can exist as a result of differences in crystal packing (packing polymorphism), conformational differences (conformational polymorphism), or changes due to co-crystallization with other chemical entities (pseudopolymorphism). Polymorphism is an important aspect of pharmaceutical development, in which case drugs typically receive regulatory approval for only a single form. Distinct polymorphic forms frequently vary considerably in terms of their physical properties. Altered dissolution rates, thermal stability, and hygroscopicity are frequently observed.

The term "prodrugs" refers to compounds that have cleavable groups and become by solvolysis or under physiological conditions the compounds of Formula (I) or (I'), which are pharmaceutically active in vivo. Such examples include, but are not limited to, ester derivatives and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases, it is desirable to prepare double ester type prodrugs such as (acyloxy)alkyl esters or ((alkoxycarbonyl)oxy)alkylesters. $C_1$ to $C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formula (I) or (I') may be preferred.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The terms "administer," "administering," or "administration," refers to implanting, absorbing, ingesting, injecting, inhaling, or otherwise introducing an inventive compound, or a pharmaceutical composition thereof.

The terms "treatment," "treat," and "treating" refer to reversing, alleviating, delaying the onset of, or inhibiting the progress of a microbial infection (e.g., a bacterial infection). In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of exposure to microorganisms, in light of a history of symptoms, and/or in light of genetic or other susceptibility factors). Treatment may also be continued after symptoms have resolved, for example, to delay and/or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound of Formula (I) or (I') is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent. In certain embodiments, a therapeutically effective amount is effective for treating a microbial infection (e.g., a bacterial infection) in a subject, for inhibiting the growth and/or reproduction of a microorganism (e.g., a bacterium), for killing a microorganism (e.g., a bacterium), for inhibiting the formation and/or growth of a biofilm, for reducing or removing a biofilm, and/or for disinfecting a surface.

A "prophylactically effective amount" of a compound of Formula (I) or (I') is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is effective for preventing a microbial infection (e.g., a bacterial infection) in a subject, for inhibiting the growth and/or reproduction of a microorganism (e.g., a bacterium), for killing a microorganism (e.g., a bacterium), for inhibiting the formation and/or growth of a biofilm, for reducing or removing a biofilm, and/or for disinfecting a surface.

The term "inhibition", "inhibiting", "inhibit," "inhibitory," or "inhibitor" refers to the ability of a compound to reduce, slow, halt, or prevent activity of a particular biological process (e.g., the growth or reproduction) of a microorganism (e.g., a bacterium, *mycobacterium*, archaeon, protist, fungus, or parasite) relative to vehicle.

The term "minimum inhibitory concentration" or "MIC" refers to the lowest concentration of a compound that will inhibit the visible growth of a microorganism (e.g., a bacterium, *mycobacterium*, archaeon, protist, fungus, or parasite) after overnight (e.g., about 16 to about 20 hours) incubation of the microorganism with the compound at about 37° C.

The term "minimum bactericidal concentration" or "MBC" refers to the lowest concentration of a compound required to kill a bacterium. The MBC of a compound can be determined from broth dilution MIC tests by subculturing to agar plates that do not contain the compound. In certain embodiments, the MBC of a compound is identified by determining the lowest concentration of the compound that reduces the viability of the initial bacterial inoculum by at least 99.9%.

The term "minimum biofilm eradication concentration" or "MBEC" refers to the lowest concentration of a compound required to kill at least 99.9% biofilm.

The term "microorganism" refers to a microscopic organism, which may be a single-cell or multicellular organism. In certain embodiments, the microorganism is a bacterium, *mycobacterium*, archaeon, protist (e.g., protozoon, alga), fungus (e.g., yeast, mold), or parasite. In certain embodiments, the microorganism is a bacterium. In certain embodiments, the length or diameter of a microorganism is at most about 10 cm, at most about 1 cm, at most about 1 mm, at most about 100 µm, at most about 10 µm, at most about 1 µm, at most about 100 nm, or at most about 10 nm. In certain embodiments, the length or diameter of a microorganism is at most about 10 µm.

The term "biofilm" refers to a group of microorganisms (e.g., bacteria) in which cells of the microorganisms stick to each other on a surface. These adherent cells are frequently embedded within a self-produced matrix of extracellular polymeric substance (EPS). The EPS is a polymeric conglomeration generally composed of extracellular DNA, proteins, and polysaccharides. Biofilms may form on living or non-living surfaces and can be prevalent in natural, industrial, and hospital settings. The cells growing in a biofilm are physiologically distinct from planktonic cells of the same microorganism, which are single-cells that may float or swim in a liquid medium. Biofilms have been found to be involved in a wide variety of microbial infections. Biofilms are formed by numerous Gram-negative and Gram-positive bacterial species. Non-limiting examples include *Bacillus* spp, *Staphylococcus* spp, *Pseudomonas* spp, and *Acinetobacter* spp.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

The term "planktonic" refers to any of the group of passively floating, drifting, or somewhat motile organisms occurring in a liquid medium (e.g., an aqueous solution). This group includes, but is not limited to, microscopic bacteria, algae, or protozoa.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 2A shows the structures and exemplary antimicrobial activities of broxyquinoline and HQ-1. FIG. 2B shows an exemplary synthesis of certain compounds of the invention using reductive amination. FIG. 2C shows the structures and exemplary yields of certain compounds of the invention prepared by reductive amination.

DETAILED DESCRIPTION OF CERTAIN EMBODIMENTS OF THE INVENTION

Figure 1:
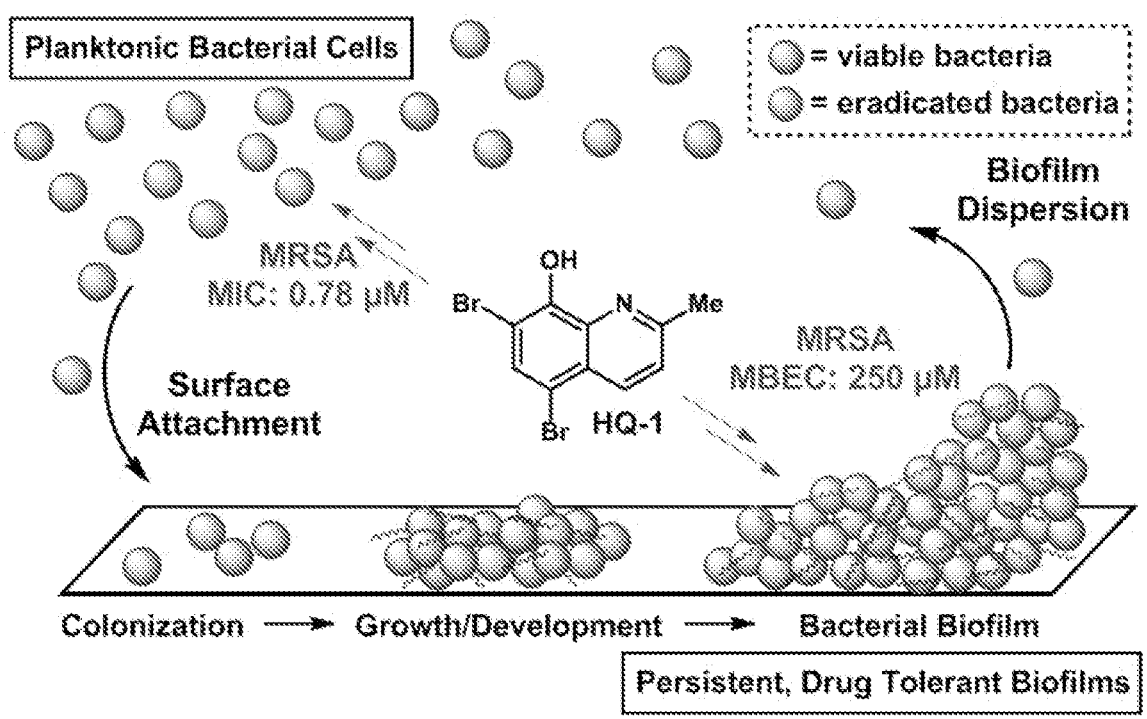
FIG. 1 shows planktonic bacteria attaching to a surface and developing into bacterial biofilms, and also shows HQ-1 as a small molecule active against both planktonic and biofilm MRSA cells.

Certain antimicrobial phenazine derivatives and quinoline derivatives have been reported in international PCT application publication, WO 2015/100331, published Jul. 2, 2015; and U.S. provisional patent applications, U.S. Ser. No. 62/193,045, filed Jul. 15, 2015, and U.S. Ser. No. 62/136,053, filed Mar. 20, 2015; each of which is incorporated herein by reference. The present invention provides, in one aspect, halogenated quinoline derivatives, such as compounds of Formula (I), and salts (e.g., pharmaceutically acceptable salts), solvates, hydrates, polymorphs, co-crystals, tautomers, stereoisomers, isotopically labeled derivatives, and prodrugs thereof. The present invention provides, in another aspect, halogenated quinoline derivatives, such as compounds of Formula (I'), and salts (e.g., pharmaceutically acceptable salts), solvates, hydrates, polymorphs, co-crystals, tautomers, stereoisomers, isotopically labeled derivatives, and prodrugs thereof. The compounds of the invention are expected to be antimicrobial agents. Without wishing to be bound by any particular theory, the compounds of the invention may inhibit and/or kill a microorganism, and/or reduce or remove biofilms through a mechanism other than the destruction of microbial membranes, e.g., the compounds of the invention may inhibit and/or kill a microorganism, and/or reduce or remove a biofilm through an iron(II)-dependent mode of action (e.g., through the targeting of a metalloprotein critical to biofilm viability). The present invention also provides compositions including pharmaceutical compositions, kits, uses, and methods that involve the compounds of the invention and may be useful in preventing and/or treating a microbial infection in a subject, inhibiting the growth and/or reproduction of a microorganism (e.g., bacterium, mycobacterium, archaeon, protist, fungus, or parasite), killing a microorganism, inhibiting the formation and/or growth of a biofilm, reducing or removing a biofilm, or disinfecting a surface. In certain embodiments, the microorganism is a bacterium. In certain embodiments, the bacterium is a Gram-positive bacterium (e.g., a species of *Staphylococcus* or *Enterococcus*). In certain embodiments, the bacterium is a Gram-negative bacterium (e.g., an *Acinetobacter* species).

In certain embodiments, the compounds of the invention are improved quinoline derivatives and showed unexpected and superior properties compared to known quinoline derivatives, such as enhanced inhibitory activity against bacteria, e.g., *Staphylococcus aureus* (*S. aureus*), *Staphylococcus epidermidis* (*S. epidermidis*), and/or *Enterococcus faecium* (*E. faecium*). *Staphylococcus aureus* is a human pathogen that is notorious for life-threatening drug-resistant infections in hospitals and the community (H. F. Chambers and F. R. DeLeo, *Nat. Rev. Microbiol.*, 2009, 7, 629-641). In the United States alone, there are more annual deaths from methicillin-resistant *Staphylococcus aureus* (MRSA) related microbial infections than AIDS (IDSA Policy Paper d CID 2011:52 (Suppl 5) d S397). *Staphylococcus epidermidis* is also a pathogen of great importance as it is particularly prevalent in persistent microbial infections associated with catheters (I. Uckay, D. Pittet, P. Vaudaux, H. Sax, D. Lew, and F. Waldvogel, *Ann. Med.*, 2009, 41, 109-119).

Furthermore, compounds disclosed herein may be effective agents for the inhibition of biofilm growth and/or clearance of existing biofilms. Bacterial biofilms are surface-attached bacterial communities that are encased within a secreted matrix of biomolecules (e.g., extracellular DNA, proteins, polysaccharides) known as the extracellular polymeric substance (EPS). Bacterial cells within a biofilm take on a completely different physiology than their free-swimming planktonic counterparts and are notorious for being highly resistant to conventional antibiotic treatments and host immune responses (Donlan, R. M. and Costerton, J. W. *Clin. Microbiol. Rev.* 2002, 15, 167-193). The National Institutes of Health has reported that biofilms are present in up to 80% of all bacterial infections. Unfortunately, biofilms are notorious for their resistance to conventional antibiotic treatments, and therefore our current arsenal of antibiotics does not include agents that effectively target biofilm machinery or clear established biofilms in a clinical setting. Such antibiofilm agents would lead to significant breakthroughs in how bacterial infections are treated and would result in the effective treatment of many life-threatening bacterial infections.

Bacterial biofilm formation is governed by a signaling process known as quorum sensing, which is used by bacteria to monitor population density and control bacterial virulence (Camilli, A. and Bassler, B. L. *Science* 2006, 311, 1113-1116; Ng, W.-L. and Bassler, B. L. *Annu. Rev. Genet.* 2009, 43, 197-222). Quorum sensing is used by free-swimming, individual planktonic bacteria to coordinate the simultaneous attachment and colonization of a surface followed by biofilm formation and maturation. The coordinated surface attachment of bacteria overwhelms immune responses mounted by host organisms, enabling the successful colonization of surfaces (e.g., tissue surfaces) by bacteria. Bacterial biofilms are known to be greater than 1000-fold more resistant to conventional antibiotics when compared to their planktonic counterparts. Therapeutic strategies targeting quorum sensing and/or biofilm formation and dispersion phenotypes have become a promising antibacterial strategy as small molecules capable of inhibiting bacterial biofilm formation via non-growth inhibitory mechanisms or removing pre-formed bacterial biofilms are of clinical importance.

The inventive compounds preferably have minimal to no adverse side effects. In certain embodiments, the compounds exhibit low cytotoxicity against mammalian (e.g., human) cells. In certain embodiments, the compounds show low hemolysis activity.

Compounds

One aspect of the invention relates to halogenated quinoline derivatives, which are compounds believed to be antimicrobial agents. In certain embodiments, the compounds of the invention are compounds of Formula (I'):

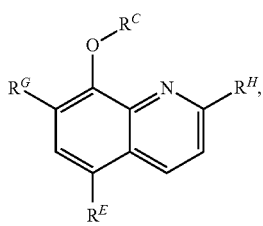

and salts (e.g., pharmaceutically acceptable salts), solvates, hydrates, polymorphs, co-crystals, tautomers, stereoisomers, isotopically labeled derivatives, and prodrugs thereof, wherein:

$R^H$ is —CO$_2$R$^L$, —C$_{1-6}$-alkylene-OR$^L$, —CHO, —CN, —NR$^M_2$,

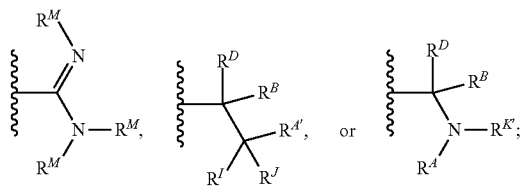

$R^{A'}$ is H or $R^A$;

$R^A$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^B$ is H, halogen, or substituted or unsubstituted C$_{1-6}$ alkyl;

$R^D$ is H, halogen, or substituted or unsubstituted C$_{1-6}$ alkyl;

$R^I$ is H, halogen, or substituted or unsubstituted C$_{1-6}$ alkyl;

$R^J$ is H, halogen, or substituted or unsubstituted C$_{1-6}$ alkyl;

$R^{K'}$ is H or $R^K$.

$R^K$ is substituted or unsubstituted C$_{1-6}$ alkyl or a nitrogen protecting group;

each $R^L$ is independently H, substituted or unsubstituted C$_{1-6}$ alkyl, or an oxygen protecting group;

each $R^M$ is independently H, substituted or unsubstituted C$_{1-6}$ alkyl, or a nitrogen protecting group;

$R^C$ is H, substituted or unsubstituted C$_{1-6}$ alkyl, or an oxygen protecting group;

$R^E$ is halogen; and $R^G$ is halogen.

Another aspect of the invention relates to halogenated quinoline derivatives, which are compounds believed to be antimicrobial agents. In certain embodiments, the compounds of the invention are compounds of Formula (I):

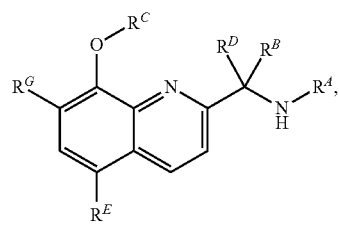

and salts (e.g., pharmaceutically acceptable salts), solvates, hydrates, polymorphs, co-crystals, tautomers, stereoisomers, isotopically labeled derivatives, and prodrugs thereof, wherein:

$R^A$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^B$ is H, halogen, or substituted or unsubstituted C$_{1-6}$ alkyl;

$R^D$ is H, halogen, or substituted or unsubstituted C$_{1-6}$ alkyl;

$R^C$ is H, substituted or unsubstituted C$_{1-6}$ alkyl, or an oxygen protecting group;

$R^E$ is halogen; and $R^G$ is halogen.

Another aspect of the invention relates to halogenated quinoline derivatives, which are compounds believed to be antimicrobial agents. In certain embodiments, the compounds of the invention are compounds of Formula (I'-c):

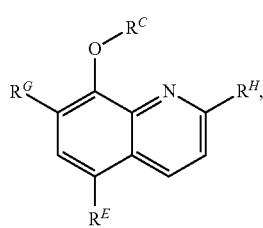

or a pharmaceutically acceptable salt thereof, wherein:

$R^H$ is —CO$_2$R$^L$, —C$_{1-6}$-alkylene-OR$^L$, —CHO, —CN, —NR$^M_2$,

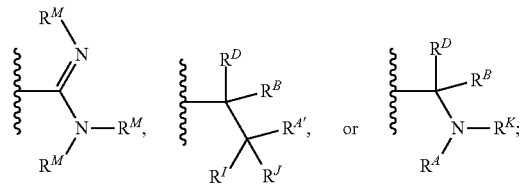

$R^{A'}$ is H or $R^A$;

$R^A$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^B$ is H, halogen, or substituted or unsubstituted $C_{1-6}$ alkyl;

$R^D$ is H, halogen, or substituted or unsubstituted $C_{1-6}$ alkyl;

$R^I$ is H, halogen, or substituted or unsubstituted $C_{1-6}$ alkyl;

$R^J$ is H, halogen, or substituted or unsubstituted $C_{1-6}$ alkyl;

$R^K$ is substituted or unsubstituted $C_{1-6}$ alkyl or a nitrogen protecting group;

each $R^L$ is independently H, substituted or unsubstituted $C_{1-6}$ alkyl, or an oxygen protecting group;

each $R^M$ is independently H, substituted or unsubstituted $C_{1-6}$ alkyl, or a nitrogen protecting group;

$R^C$ is H, substituted or unsubstituted $C_{1-6}$ alkyl, or an oxygen protecting group;

$R^E$ is halogen; and $R^G$ is halogen.

Formula (I) also includes substituent $R^A$ on a nitrogen atom. Formula (I') also includes substituent $R^A$ on a nitrogen atom. In certain embodiments, $R^A$ is substituted or unsubstituted alkyl. In certain embodiments, $R^A$ is substituted or unsubstituted $C_{1-6}$ alkyl (e.g., substituted or unsubstituted $C_{3-6}$ alkyl). In certain embodiments, $R^A$ is Me. In certain embodiments, $R^A$ is substituted methyl (e.g., —$CF_3$ or Bn). In certain embodiments, $R^A$ is Et or substituted ethyl (e.g., perfluoroethyl). In certain embodiments, $R^A$ is Pr or substituted propyl (e.g., perfluoropropyl). In certain embodiments, $R^A$ is Bu (e.g., n-Bu, t-Bu, sec-Bu, or i-Bu) or substituted butyl (e.g., perfluorobutyl). In certain embodiments, $R^A$ is unsubstituted pentyl, substituted pentyl (e.g., perfluoropentyl), unsubstituted hexyl, or substituted hexyl (e.g., perfluorohexyl). In certain embodiments, $R^A$ is not Me or Et. In certain embodiments, $R^A$ is not unsubstituted $C_{1-3}$ alkyl. In certain embodiments, $R^A$ is not substituted or unsubstituted $C_{1-3}$ alkyl. In certain embodiments, $R^A$ is substituted or unsubstituted alkenyl (e.g., substituted or unsubstituted $C_{2-6}$ alkenyl, e.g., substituted or unsubstituted $C_{3-6}$ alkenyl). In certain embodiments, $R^A$ is substituted or unsubstituted alkynyl (e.g., substituted or unsubstituted $C_{2-6}$ alkynyl, e.g., substituted or unsubstituted $C_{3-6}$ alkynyl). In certain embodiments, $R^A$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^A$ is substituted or unsubstituted cyclopropyl, substituted or unsubstituted cyclobutyl, substituted or unsubstituted cyclopentyl, or substituted or unsubstituted cyclohexyl. In certain embodiments, $R^A$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^A$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl.

In certain embodiments, $R^A$ is substituted or unsubstituted aryl (e.g., substituted or unsubstituted, 6- to 14-membered aryl). In certain embodiments, $R^A$ is unsubstituted phenyl. In certain embodiments, $R^A$ is substituted phenyl. In certain embodiments, $R^A$ is of the formula:

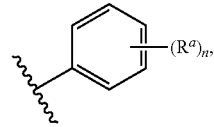

wherein:

each instance of $R^a$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^1$, —$N(R^1)_2$, —$SR^1$, —CN, —SCN, —$C(=NR^1)R^1$, —$C(=NR^1)OR^1$, —$C(=NR^1)N(R^1)_2$, —$C(=O)R^1$, —$C(=O)OR^1$, —$C(=O)N(R^1)_2$, —$NO_2$, —$NR^1C(=O)R^1$, —$NR^1C(=O)OR^1$, —$NR^1C(=O)N(R^1)_2$, —$OC(=O)R^1$, —$OC(=O)OR^1$, or —$OC(=O)N(R^1)_2$, wherein each instance of $R^1$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^1$ are joined to form a substituted or unsubstituted heterocyclic or substituted or unsubstituted heteroaryl ring; and n is 0, 1, 2, 3, 4, or 5.

$R^A$ may include one or more instances of substituent $R^a$ on the phenyl ring. When $R^A$ includes two or more instances of $R^a$ on the phenyl ring, any two instances of $R^1$ may be the same or different from each other. In certain embodiments, at least one instance of $R^a$ is halogen. In certain embodiments, at least one instance of $R^a$ is F. In certain embodiments, at least one instance of $R^a$ is Cl. In certain embodiments, at least one instance of $R^a$ is Br. In certain embodiments, at least one instance of $R^a$ is I (iodine). In certain embodiments, at least one instance of $R^a$ is substituted or unsubstituted alkyl (e.g., substituted or unsubstituted $C_{1-6}$ alkyl). In certain embodiments, at least one instance of $R^a$ is Me. In certain embodiments, at least one instance of $R^a$ is substituted methyl (e.g., —$CF_3$ or Bn). In certain embodiments, at least one instance of $R^a$ is Et or substituted ethyl (e.g., perfluoroethyl). In certain embodiments, at least one instance of $R^a$ is Pr or substituted propyl (e.g., perfluoropropyl). In certain embodiments, at least one instance of $R^a$ is Bu (e.g., n-Bu, t-Bu, sec-Bu, or i-Bu) or substituted butyl (e.g., perfluorobutyl). In certain embodiments, at least one instance of $R^a$ is unsubstituted pentyl, substituted pentyl (e.g., perfluoropentyl), unsubstituted hexyl, or substituted hexyl (e.g., perfluorohexyl). In certain embodiments, at least one instance of $R^a$ is halogen or substituted or unsubstituted $C_{1-6}$ alkyl. In certain embodiments, each instance of $R^a$ is independently halogen or substituted or unsubstituted $C_{1-6}$ alkyl. In certain embodiments, at least one instance of $R^a$ is substituted or unsubstituted alkenyl (e.g., substituted or unsubstituted $C_{2-6}$ alkenyl). In certain embodiments, at least one instance of $R^a$ is substituted or unsubstituted alkynyl (e.g., substituted or unsubstituted $C_{2-6}$ alkynyl). In certain embodiments, at least one instance of $R^a$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^a$ is substituted or unsubstituted cyclopropyl, substituted or unsubstituted cyclobutyl, substituted or unsubstituted cyclopentyl, or substituted or unsubstituted cyclohexyl. In certain embodiments, at least one instance of $R^a$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^a$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, at least one instance of $R^a$ is substituted or unsubstituted aryl (e.g., substituted or unsubstituted, 6- to 10-membered aryl). In certain embodiments, at least one instance of $R^a$ is unsubstituted phenyl. In certain embodiments, at least one instance of $R^a$ is substituted phenyl. In certain embodiments, at least one instance of $R^a$ is substituted or unsubstituted naphthyl. In certain embodiments, at least one instance of $R^a$ is substituted or unsubstituted heteroaryl. In certain embodiments, at least one instance of $R^a$ is substituted or unsubstituted, 5- to 6-membered, monocyclic heteroaryl, wherein one, two, three, or four atoms in the heteroaryl ring system are independently nitrogen, oxygen, or sulfur. In certain embodiments, at least one instance of $R^a$ is substituted or unsubstituted, 9- to 10-membered, bicyclic heteroaryl, wherein one, two, three, or four atoms in the heteroaryl ring system are independently nitrogen, oxygen, or sulfur. In certain embodiments, at least one instance of $R^a$ is —$OR^1$ (e.g., —OH, —O(substituted or unsubstituted $C_{1-6}$ alkyl) (e.g., —OMe, —$OCF_3$, —OEt, —OPr, —OBu, or —OBn), or —O(substituted or unsubstituted phenyl) (e.g., —OPh)). In certain embodiments, at least one instance of $R^a$ is —OMe. In certain embodiments, at least one instance of $R^a$ is —$SR^1$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^a$ is —$N(R^1)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^a$ is —CN or —SCN. In certain embodiments, at least one instance of $R^a$ is —$NO_2$. In certain embodiments, at least one instance of $R^a$ is —$C(=NR^1)R^1$, —$C(=NR^1)OR^1$, or —$C(=NR^1)N(R^1)_2$. In certain embodiments, at least one instance of $R^a$ is —$C(=O)R^1$ (e.g., —C(=O)(substituted or unsubstituted alkyl) (e.g., —C(=O)Me) or —C(=O)(substituted or unsubstituted phenyl)). In certain embodiments, at least one instance of $R^a$ is —$C(=O)OR^1$ (e.g., —C(=O)OH, —C(=O)O(substituted or unsubstituted alkyl) (e.g., —C(=O)OMe), or —C(=O)O(substituted or unsubstituted phenyl)). In certain embodiments, at least one instance of $R^a$ is —$C(=O)N(R^1)_2$ (e.g., —$C(=O)NH_2$, —C(=O)NH(substituted or unsubstituted alkyl) (e.g., —C(=O)NHMe), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, at least one instance of $R^a$ is —$NR^1C(=O)R^1$ (e.g., —NHC(=O)(substituted or unsubstituted $C_{1-6}$ alkyl) (e.g., —NHC(=O)Me) or —NHC(=O)(substituted or unsubstituted phenyl)). In certain embodiments, at least one instance of $R^a$ is —$NR^1C(=O)OR^1$. In certain embodiments, at least one instance of $R^a$ is —$NR^1C(=O)N(R^1)_2$ (e.g., —$NHC(=O)NH_2$, —NHC(=O)NH(substituted or unsubstituted $C_{1-6}$ alkyl) (e.g., —NHC(=O)NHMe)). In certain embodiments, at least one instance of $R^a$ is —$OC(=O)R^1$ (e.g., —OC(=O)(substituted or unsubstituted alkyl) or —OC(=O)(substituted or unsubstituted phenyl)), —$OC(=O)OR^1$ (e.g., —OC(=O)O(substituted or unsubstituted alkyl) or —OC(=O)O(substituted or unsubstituted phenyl)), or —$OC(=O)N(R^1)_2$ (e.g., —$OC(=O)NH_2$, —OC(=O)NH(substituted or unsubstituted alkyl), —OC(=O)NH(substituted or unsubstituted phenyl), —OC(=O)N(substituted or unsubstituted alkyl)-(substituted or unsubstituted alkyl), or —OC(=O)N(substituted or unsubstituted phenyl)-(substituted or unsubstituted alkyl)).

$R^a$ may include one or more instances of substituent $R^1$. When $R^a$ includes two or more instances of $R^1$, any two instances of $R^1$ may be the same or different from each other. In certain embodiments, at least one instance of $R^1$ is H. In certain embodiments, each instance of $R^1$ is H. In certain embodiments, at least one instance of $R^1$ is substituted or unsubstituted alkyl (e.g., substituted or unsubstituted $C_{1-6}$ alkyl (e.g., Me)). In certain embodiments, at least one instance of $R^1$ is substituted or unsubstituted acyl. In certain embodiments, at least one instance of $R^1$ is substituted or unsubstituted alkenyl (e.g., substituted or unsubstituted $C_{2-6}$ alkenyl) or substituted or unsubstituted alkynyl (e.g., substituted or unsubstituted $C_{2-6}$ alkynyl). In certain embodiments, at least one instance of $R^1$ is substituted or unsubstituted carbocyclyl (e.g., substituted or unsubstituted, 3- to 7-membered, monocyclic carbocyclyl comprising zero, one, or two double bonds in the carbocyclic ring system), substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur), substituted or unsubstituted aryl (e.g., substituted or unsubstituted phenyl), or substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^1$ is a nitrogen protecting group (e.g., Bn, Boc, Cbz, Fmoc, trifluoroacetyl, triphenylmethyl, acetyl, or Ts) when attached to a nitrogen atom, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom. In certain embodiments, two instances of $R^1$ are joined to form a substituted or unsubstituted heterocyclic or substituted or unsubstituted heteroaryl ring.

In certain embodiments, n is 0. In certain embodiments, n is 1. In certain embodiments, n is 2. In certain embodiments, n is 3. In certain embodiments, n is 4. In certain embodiments, n is 5. In certain embodiments, n is 1, 2, 3, 4, or 5. In certain embodiments, $R^4$ is of the formula:

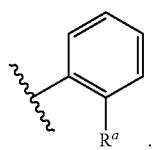

In certain embodiments, $R^A$ is of the formula:

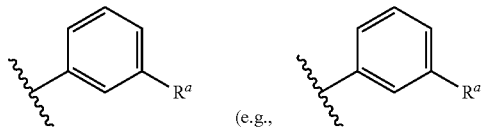

wherein $R^a$ is halogen or substituted or unsubstituted $C_{1-6}$ alkyl (e.g., 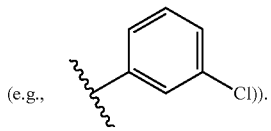).

In certain embodiments, $R^A$ is of the formula:

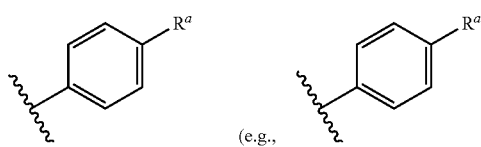

wherein $R^a$ is halogen or substituted or unsubstituted $C_{1-6}$ alkyl (e.g., 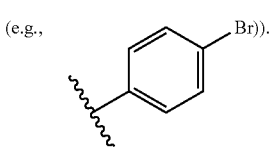).

In certain embodiments, $R^A$ is of the formula:

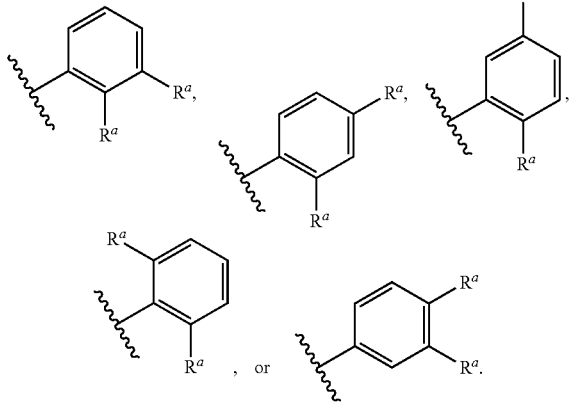

In certain embodiments, $R^A$ is of the formula:

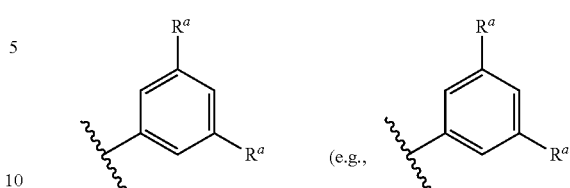

wherein each instance of $R^a$ is independently halogen or substituted or unsubstituted $C_{1-6}$ alkyl (e.g., 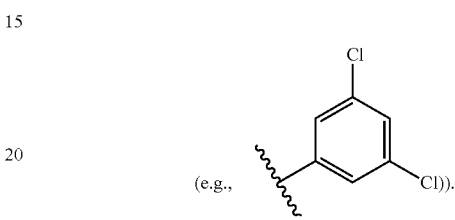).

In certain embodiments, $R^A$ is of the formula:

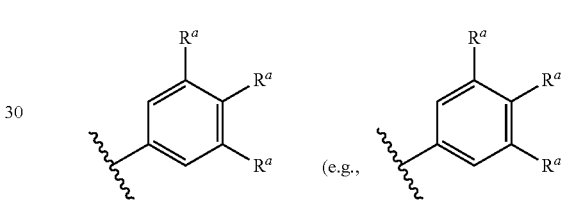

wherein each instance of $R^a$ is independently halogen or substituted or unsubstituted $C_{1-6}$ alkyl (e.g.,

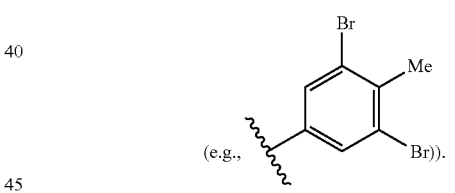).

In certain embodiments, $R^A$ is of the formula:

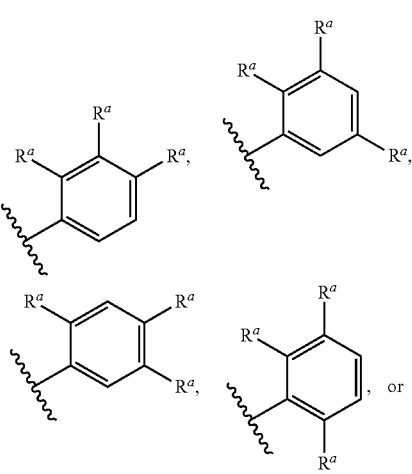

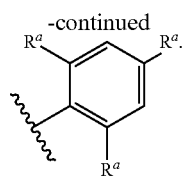

In certain embodiments, $R^A$ is substituted or unsubstituted heteroaryl. In certain embodiments, $R^A$ is substituted or unsubstituted, 5- to 6-membered, monocyclic heteroaryl, wherein one, two, three, or four atoms in the heteroaryl ring system are independently nitrogen, oxygen, or sulfur. In certain embodiments, $R^A$ is substituted or unsubstituted, 9- to 10-membered, bicyclic heteroaryl, wherein one, two, three, or four atoms in the heteroaryl ring system are independently nitrogen, oxygen, or sulfur. In certain embodiments, $R^A$ is a nitrogen protecting group (e.g., Bn, Boc, Cbz, Fmoc, trifluoroacetyl, triphenylmethyl, acetyl, or Ts). In certain embodiments, $R^A$ is a nitrogen protecting group that is not Me or Et.

Formula (I) includes substituent $R^B$. Formula (I') also includes substituent $R^B$. In certain embodiments, $R^B$ is H. In certain embodiments, $R^B$ is halogen (e.g., F, Cl, Br, or I). In certain embodiments, $R^B$ is substituted or unsubstituted alkyl (e.g., substituted or unsubstituted $C_{1-6}$ alkyl). In certain embodiments, $R^B$ is Me. In certain embodiments, $R^B$ is substituted methyl (e.g., —$CF_3$ or Bn). In certain embodiments, $R^B$ is Et, substituted ethyl (e.g., perfluoroethyl), Pr, substituted propyl (e.g., perfluoropropyl), Bu, substituted butyl (e.g., perfluorobutyl), unsubstituted pentyl, substituted pentyl (e.g., perfluoropentyl), unsubstituted hexyl, or substituted hexyl (e.g., perfluorohexyl).

Formula (I) includes substituent $R^D$. Formula (I') also includes substituent $R^D$. In certain embodiments, $R^D$ is H. In certain embodiments, $R^D$ is halogen (e.g., F, Cl, Br, or I). In certain embodiments, $R^D$ is substituted or unsubstituted alkyl (e.g., substituted or unsubstituted $C_{1-6}$ alkyl). In certain embodiments, $R^D$ is Me. In certain embodiments, $R^D$ is substituted methyl (e.g., —$CF_3$ or Bn). In certain embodiments, $R^D$ is Et, substituted ethyl (e.g., perfluoroethyl), Pr, substituted propyl (e.g., perfluoropropyl), Bu, substituted butyl (e.g., perfluorobutyl), unsubstituted pentyl, substituted pentyl (e.g., perfluoropentyl), unsubstituted hexyl, or substituted hexyl (e.g., perfluorohexyl).

In certain embodiments, each of $R^B$ and $R^D$ is H. In certain embodiments, each of $R^B$ and $R^D$ is halogen (e.g., F). In certain embodiments, each of $R^B$ and $R^D$ is independently H or halogen (e.g., F). In certain embodiments, $R^B$ is substituted or unsubstituted $C_{1-6}$ alkyl, and $R^D$ is H.

Formula (I) includes substituent $R^C$. Formula (I') also includes substituent $R^C$. In certain embodiments, $R^C$ is H. In certain embodiments, $R^C$ is substituted or unsubstituted alkyl (e.g., substituted or unsubstituted $C_{1-6}$ alkyl). In certain embodiments, $R^C$ is Me. In certain embodiments, $R^C$ is substituted methyl (e.g., —$CF_3$ or Bn). In certain embodiments, $R^C$ is Et, substituted ethyl (e.g., perfluoroethyl), Pr, substituted propyl (e.g., perfluoropropyl), Bu, substituted butyl (e.g., perfluorobutyl), unsubstituted pentyl, substituted pentyl (e.g., perfluoropentyl), unsubstituted hexyl, or substituted hexyl (e.g., perfluorohexyl). In certain embodiments, $R^C$ is an oxygen protecting group (e.g., silyl, TBDPS, TBDMS, TIPS, TES, TMS, MOM, THP, t-Bu, Bn, allyl, acetyl, pivaloyl, or benzoyl).

Formula (I) includes substituent $R^E$ on the quinolinyl ring. Formula (I') also includes substituent $R^E$ on the quinolinyl ring. In certain embodiments, $R^E$ is F. In certain embodiments, $R^E$ is Cl. In certain embodiments, $R^E$ is Br. In certain embodiments, $R^E$ is I.

Formula (I) also includes substituent $R^G$ on the quinolinyl ring. Formula (I') also includes substituent $R^G$ on the quinolinyl ring. In certain embodiments, $R^G$ is F. In certain embodiments, $R^G$ is Cl. In certain embodiments, $R^G$ is Br. In certain embodiments, $R^G$ is I.

In certain embodiments, each of $R^E$ and $R^G$ is F. In certain embodiments, $R^E$ is F; and $R^G$ is Cl. In certain embodiments, $R^E$ is F; and $R^G$ is Br. In certain embodiments, $R^E$ is F; and $R^G$ is I. In certain embodiments, $R^E$ is Cl; and $R^G$ is F. In certain embodiments, each of $R^E$ and $R^G$ is Cl. In certain embodiments, $R^E$ is Cl; and $R^G$ is Br. In certain embodiments, $R^E$ is Cl; and $R^G$ is I. In certain embodiments, $R^E$ is Br; and $R^G$ is F. In certain embodiments, $R^E$ is Br; and $R^G$ is Cl. In certain embodiments, each of $R^E$ and $R^G$ is Br. In certain embodiments, $R^E$ is Br; and $R^G$ is I. In certain embodiments, $R^E$ is I; and $R^G$ is F. In certain embodiments, $R^E$ is I; and $R^G$ is Cl. In certain embodiments, $R^E$ is I; and $R^G$ is Br. In certain embodiments, each of $R^E$ and $R^G$ is I. In certain embodiments, at least one of $R^E$ and $R^G$ is Br.

In certain embodiments, the compound of Formula (I) is of the formula:

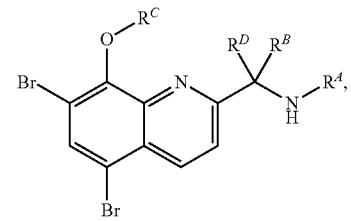

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

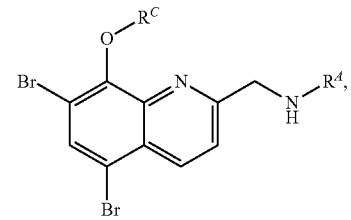

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

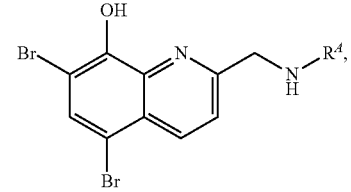

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

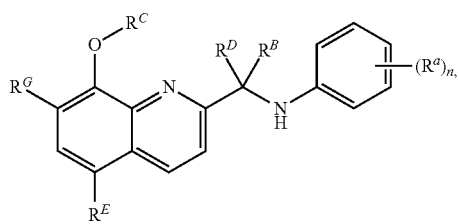

or a pharmaceutically acceptable salt, solvate, hydrate, polymorph, co-crystal, tautomer, stereoisomer, isotopically labeled derivative, or prodrug thereof, wherein $R^a$ and n are as described herein.

In certain embodiments, the compound of Formula (I) is of the formula:

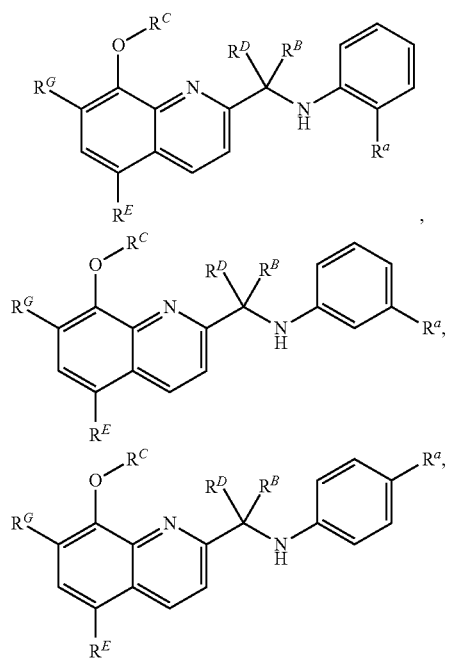

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

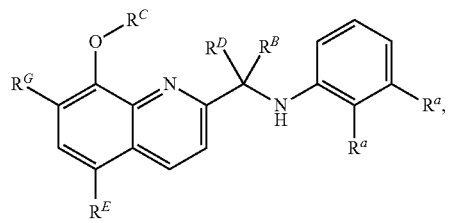

-continued

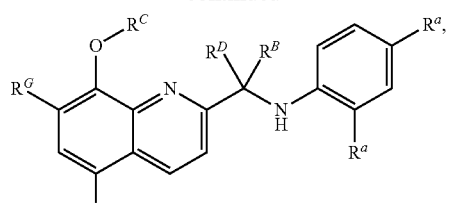

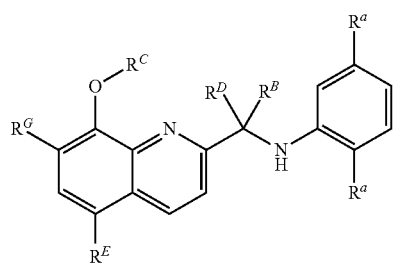

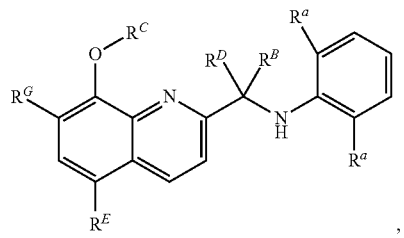

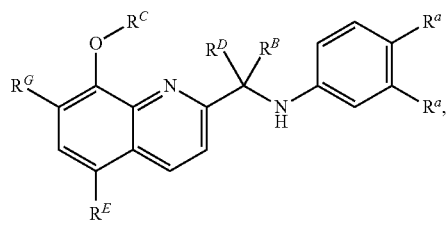

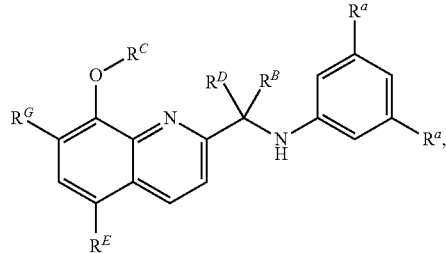

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

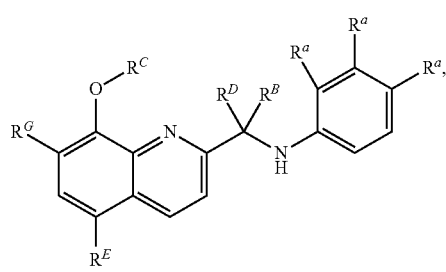

-continued

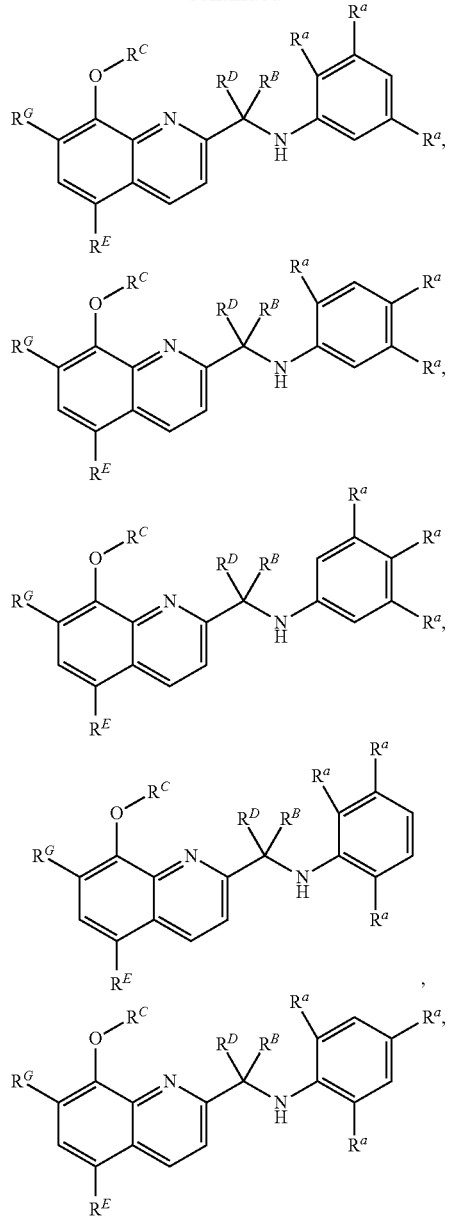

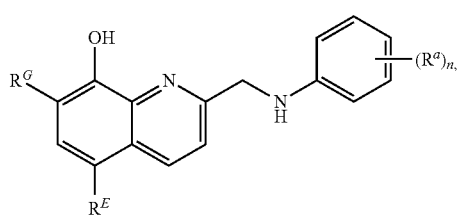

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

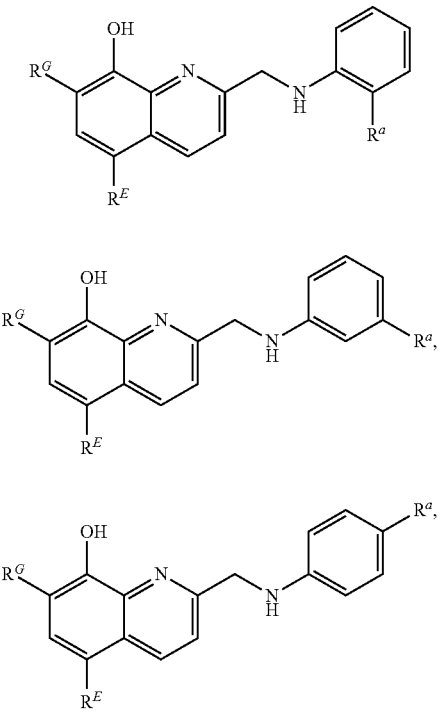

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

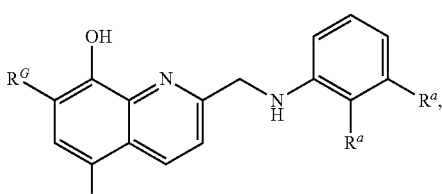

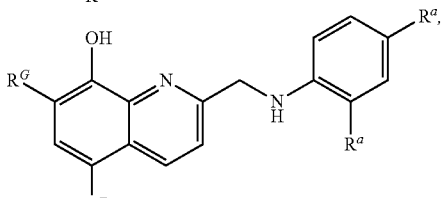

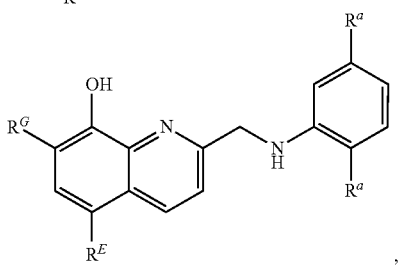

,

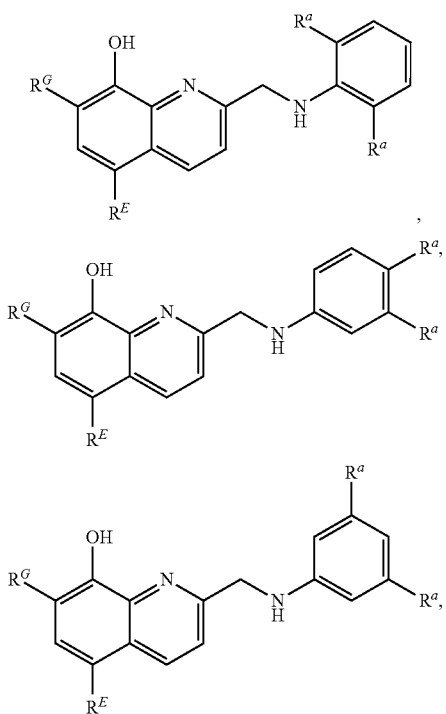

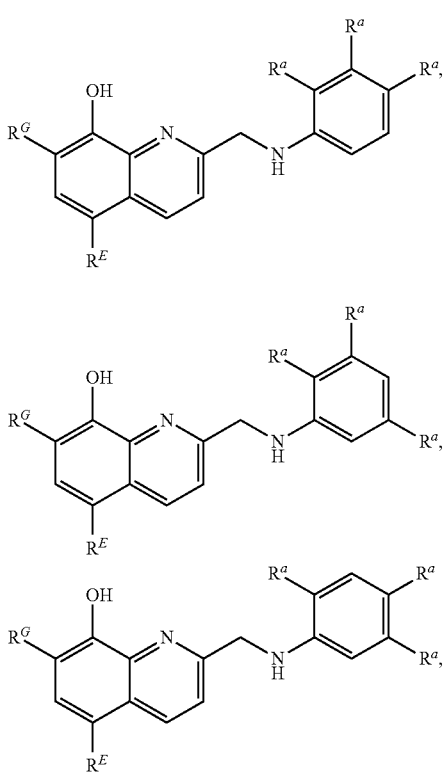

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

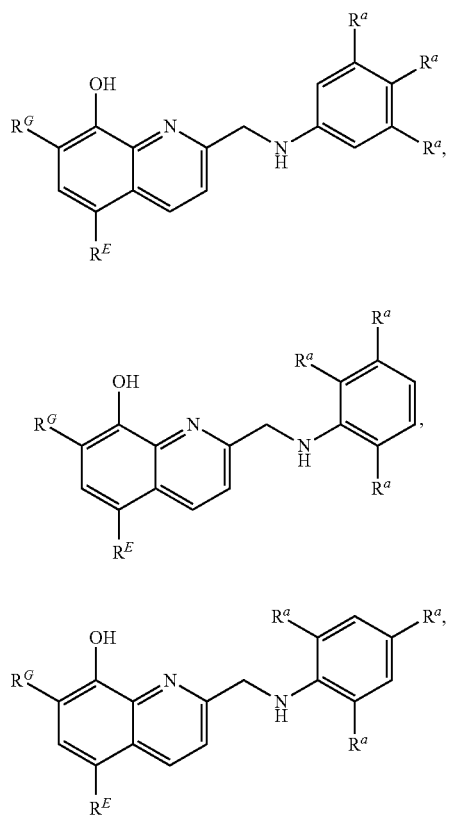

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

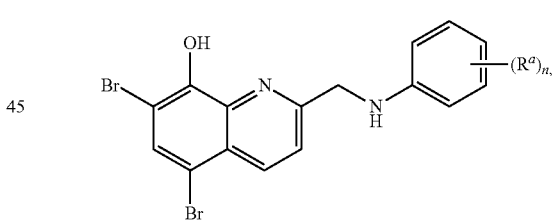

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

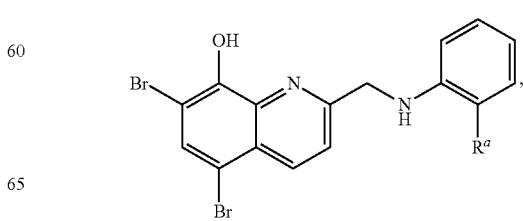

-continued

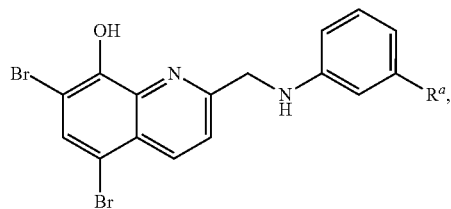

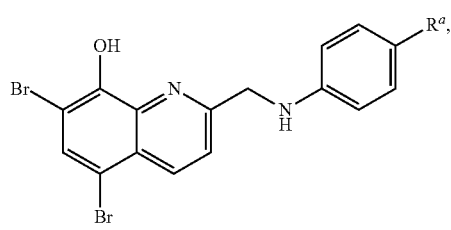

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

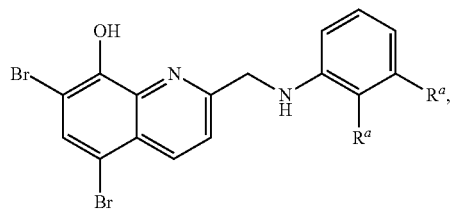

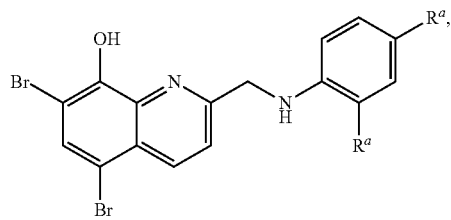

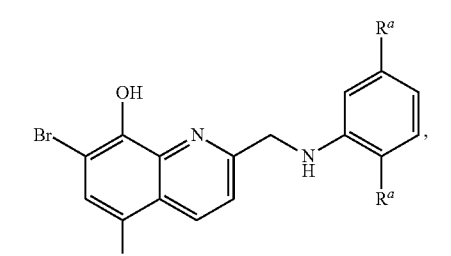

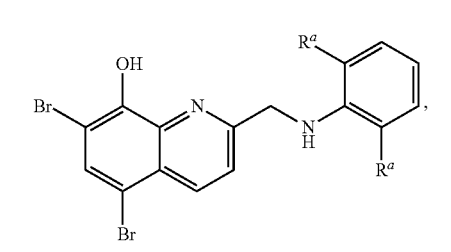

-continued

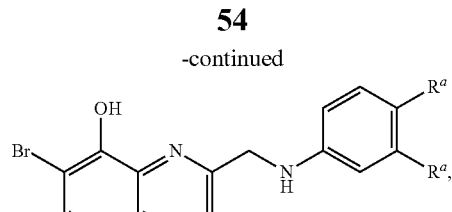

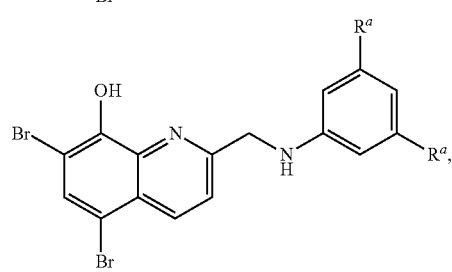

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

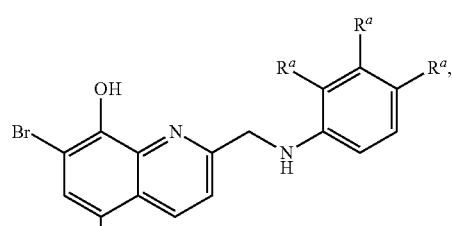

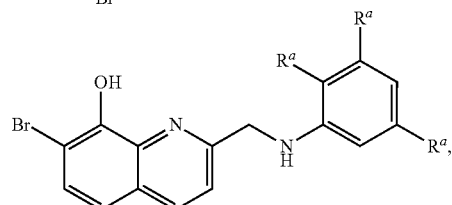

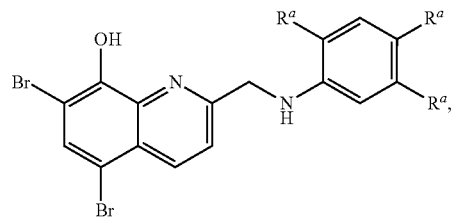

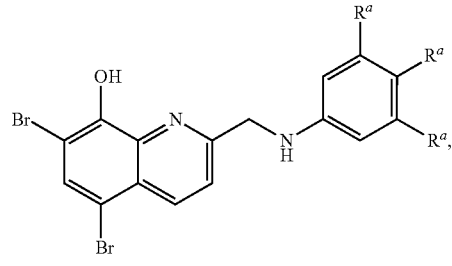

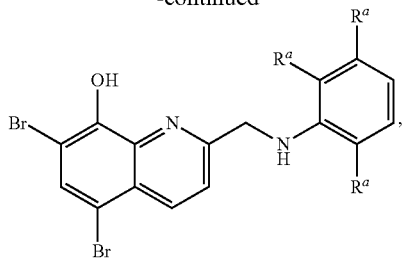

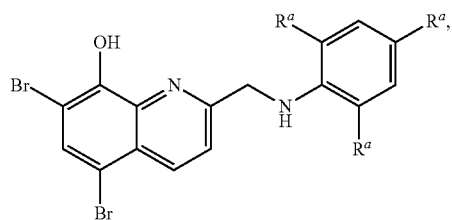

or a pharmaceutically acceptable salt, solvate, hydrate, polymorph, co-crystal, tautomer, stereoisomer, isotopically labeled derivative, or prodrug thereof.

Exemplary compounds of Formula (I) include, but are not limited to,

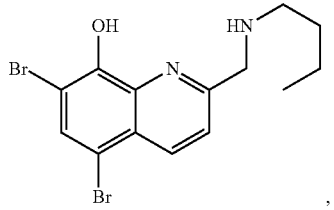
(HQ-2)

and salts, solvates, hydrates, polymorphs, co-crystals, tautomers, stereoisomers, isotopically labeled derivatives, and prodrugs thereof.

Additional exemplary compounds of Formula (I) include, but are not limited to:

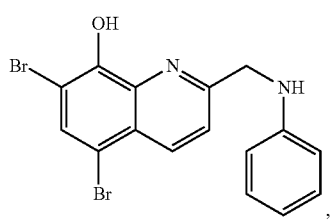
(HQ-3)

(HQ-4)

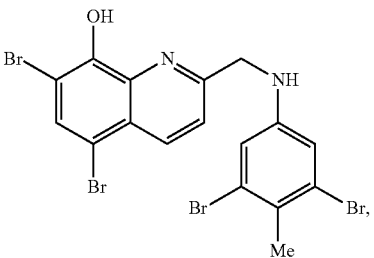
(HQ-5)

(HQ-6)

(HQ-7)

and salts, solvates, hydrates, polymorphs, co-crystals, tautomers, stereoisomers, isotopically labeled derivatives, and prodrugs thereof Additional exemplary compounds of the invention also include, but are not limited to:

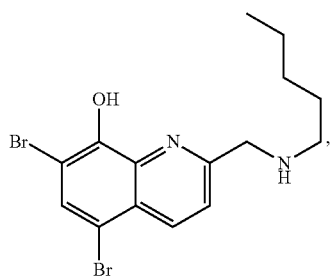

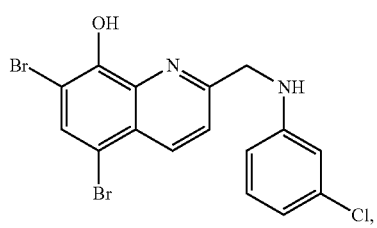

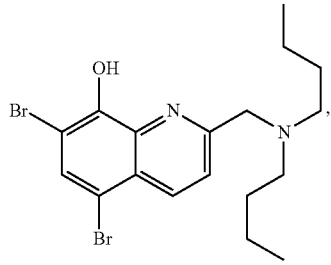

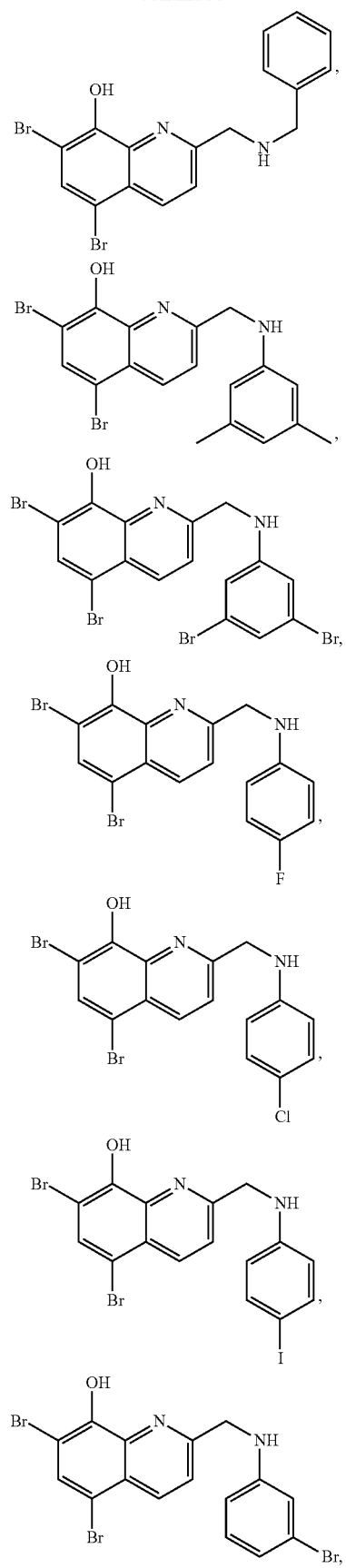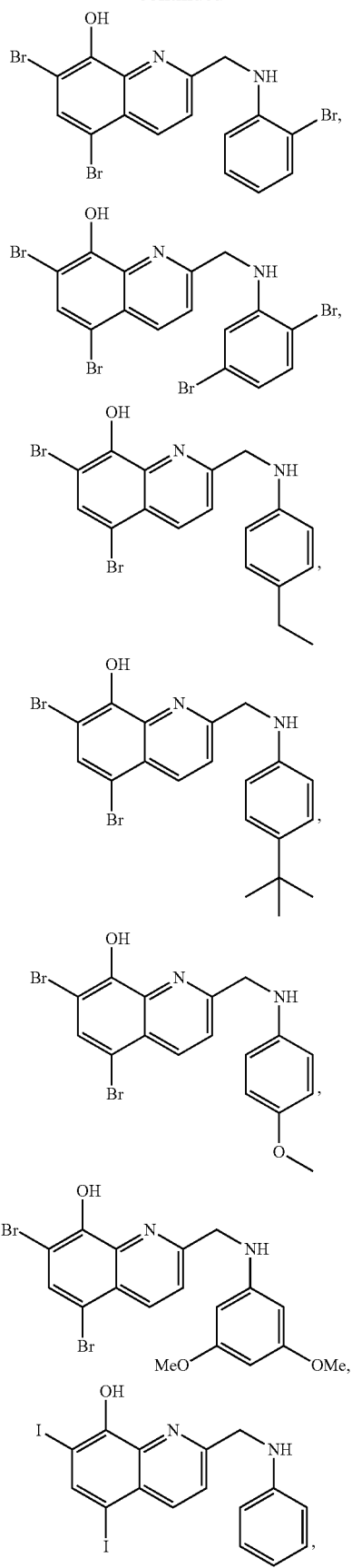

-continued

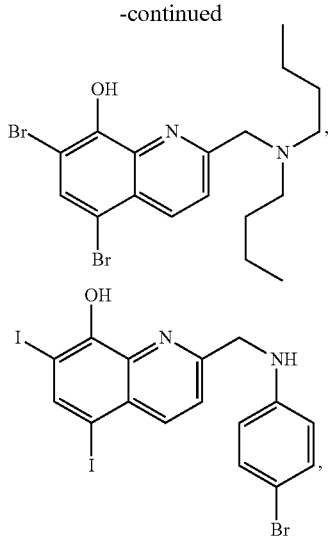

and pharmaceutically acceptable salts, solvates, hydrates, polymorphs, co-crystals, tautomers, stereoisomers, isotopically labeled derivatives, and prodrugs thereof.

In certain embodiments, the compound of Formula (I') is of the formula:

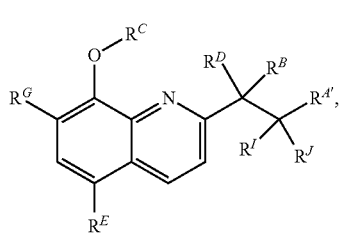

(I'-a)

or a pharmaceutically acceptable salt, solvate, hydrate, polymorph, co-crystal, tautomer, stereoisomer, isotopically labeled derivative, or prodrug thereof;

wherein $R^{A'}$ is H or $R^A$;

$R^A$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^B$ is H, halogen, or substituted or unsubstituted $C_{1-6}$ alkyl;

$R^D$ is H, halogen, or substituted or unsubstituted $C_{1-6}$ alkyl;

$R^I$ is H, halogen, or substituted or unsubstituted $C_{1-6}$ alkyl;

$R^J$ is H, halogen, or substituted or unsubstituted $C_{1-6}$ alkyl;

$R^C$ is H, substituted or unsubstituted $C_{1-6}$ alkyl, or an oxygen protecting group;

$R^E$ is halogen; and $R^G$ is halogen.

In certain embodiments, $R^{A'}$ is H, substituted or unsubstituted alkyl, or substituted or unsubstituted aryl. In certain embodiments, $R^{A'}$ is H or substituted or unsubstituted alkyl. In certain embodiments, $R^{A'}$ is H. In certain embodiments, $R^{A'}$ is substituted or unsubstituted $C_{1-6}$ alkyl (e.g., substituted or unsubstituted $C_{3-6}$ alkyl). In certain embodiments, $R^{A'}$ is Me. In certain embodiments, $R^{A'}$ is substituted methyl (e.g., —$CF_3$ or Bn). In certain embodiments, $R^{A'}$ is Et or substituted ethyl (e.g., perfluoroethyl). In certain embodiments, $R^{A'}$ is Pr or substituted propyl (e.g., perfluoropropyl). In certain embodiments, $R^{A'}$ is Bu (e.g., n-Bu, t-Bu, sec-Bu, or i-Bu) or substituted butyl (e.g., perfluorobutyl). In certain embodiments, $R^{A'}$ is unsubstituted pentyl, substituted pentyl (e.g., perfluoropentyl), unsubstituted hexyl, or substituted hexyl (e.g., perfluorohexyl).

In certain embodiments, $R^M$ is H, substituted or unsubstituted alkyl, or a nitrogen protecting group. In certain embodiments, $R^M$ is H. In certain embodiments, $R^M$ is substituted or unsubstituted $C_{1-6}$ alkyl (e.g., substituted or unsubstituted $C_{3-6}$ alkyl). In certain embodiments, $R^M$ is Me. In certain embodiments, $R^M$ is substituted methyl (e.g., —$CF_3$ or Bn). In certain embodiments, $R^M$ is Et or substituted ethyl (e.g., perfluoroethyl). In certain embodiments, $R^M$ is Pr or substituted propyl (e.g., perfluoropropyl). In certain embodiments, $R^M$ is Bu (e.g., n-Bu, t-Bu, sec-Bu, or i-Bu) or substituted butyl (e.g., perfluorobutyl). In certain embodiments, $R^M$ is unsubstituted pentyl, substituted pentyl (e.g., perfluoropentyl), unsubstituted hexyl, or substituted hexyl (e.g., perfluorohexyl).

In certain embodiments, $R^I$ is H or substituted or unsubstituted alkyl. In certain embodiments, $R^I$ is H. In certain embodiments, $R^I$ is substituted or unsubstituted $C_{1-6}$ alkyl (e.g., substituted or unsubstituted $C_{3-6}$ alkyl). In certain embodiments, $R^I$ is Me. In certain embodiments, $R^I$ is substituted methyl (e.g., —$CF_3$ or Bn). In certain embodiments, $R^I$ is Et or substituted ethyl (e.g., perfluoroethyl). In certain embodiments, $R^I$ is Pr or substituted propyl (e.g., perfluoropropyl). In certain embodiments, $R^I$ is Bu (e.g., n-Bu, t-Bu, sec-Bu, or i-Bu) or substituted butyl (e.g., perfluorobutyl). In certain embodiments, $R^I$ is unsubstituted pentyl, substituted pentyl (e.g., perfluoropentyl), unsubstituted hexyl, or substituted hexyl (e.g., perfluorohexyl).

In certain embodiments, $R^J$ is H or substituted or unsubstituted alkyl. In certain embodiments, $R^J$ is H. In certain embodiments, $R^J$ is substituted or unsubstituted $C_{1-6}$ alkyl (e.g., substituted or unsubstituted $C_{3-6}$ alkyl). In certain embodiments, $R^J$ is Me. In certain embodiments, $R^J$ is substituted methyl (e.g., —$CF_3$ or Bn). In certain embodiments, $R^J$ is Et or substituted ethyl (e.g., perfluoroethyl). In certain embodiments, $R^J$ is Pr or substituted propyl (e.g., perfluoropropyl). In certain embodiments, $R^J$ is Bu (e.g., n-Bu, t-Bu, sec-Bu, or i-Bu) or substituted butyl (e.g., perfluorobutyl). In certain embodiments, $R^J$ is unsubstituted pentyl, substituted pentyl (e.g., perfluoropentyl), unsubstituted hexyl, or substituted hexyl (e.g., perfluorohexyl).

In certain embodiments, $R^K$ is H, substituted or unsubstituted alkyl, or a nitrogen protecting group. In certain embodiments, $R^K$ is H. In certain embodiments, $R^K$ is substituted or unsubstituted $C_{1-6}$ alkyl (e.g., substituted or unsubstituted $C_{3-6}$ alkyl). In certain embodiments, $R^K$ is Me. In certain embodiments, $R^K$ is substituted methyl (e.g., —$CF_3$ or Bn). In certain embodiments, $R^K$ is Et or substituted ethyl (e.g., perfluoroethyl). In certain embodiments, $R^K$ is Pr or substituted propyl (e.g., perfluoropropyl). In certain embodiments, $R^K$ is Bu (e.g., n-Bu, t-Bu, sec-Bu, or i-Bu) or substituted butyl (e.g., perfluorobutyl). In certain embodiments, $R^K$ is n-Bu. In certain embodiments, $R^K$ is unsubstituted pentyl, substituted pentyl (e.g., perfluoropentyl), unsubstituted hexyl, or substituted hexyl (e.g., perfluorohexyl). In certain embodiments, $R^K$ is a nitrogen protecting group (e.g., Bn, Boc, Cbz, Fmoc, trifluoroacetyl, triphenylmethyl, acetyl, or Ts).

In certain embodiments, $R^K$ is H, substituted or unsubstituted alkyl, or a nitrogen protecting group. In certain embodiments, $R^{K'}$ is H. In certain embodiments, $R^{K'}$ is substituted or unsubstituted $C_{1-6}$ alkyl (e.g., substituted or unsubstituted $C_{3-6}$ alkyl). In certain embodiments, $R^{K'}$ is Me. In certain embodiments, $R^{K'}$ is substituted methyl (e.g., —$CF_3$ or Bn). In certain embodiments, $R^{K'}$ is Et or substituted ethyl (e.g., perfluoroethyl). In certain embodiments, $R^{K'}$ is Pr or substituted propyl (e.g., perfluoropropyl). In certain embodiments, $R^K$ is Bu (e.g., n-Bu, t-Bu, sec-Bu, or i-Bu) or substituted butyl (e.g., perfluorobutyl). In certain embodiments, $R^K$ is n-Bu. In certain embodiments, $R^{K'}$ is unsubstituted pentyl, substituted pentyl (e.g., perfluoropentyl), unsubstituted hexyl, or substituted hexyl (e.g., perfluorohexyl). In certain embodiments, $R^{K'}$ is a nitrogen protecting group (e.g., Bn, Boc, Cbz, Fmoc, trifluoroacetyl, triphenylmethyl, acetyl, or Ts).

In certain embodiments, the compound of Formula (I') is of the formula:

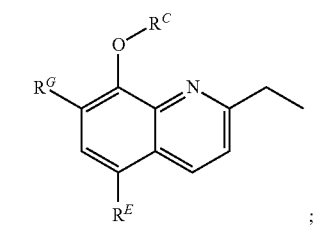

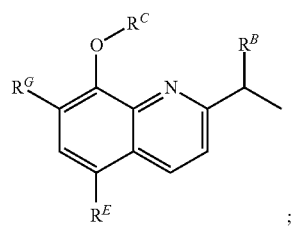

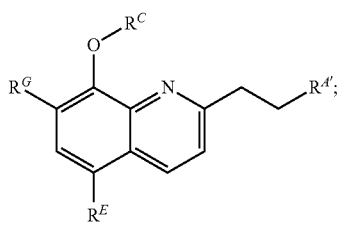

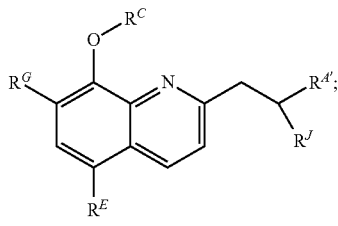

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of the formula:

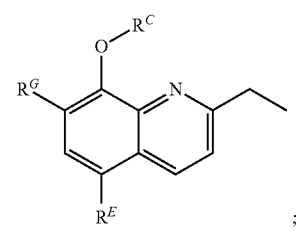

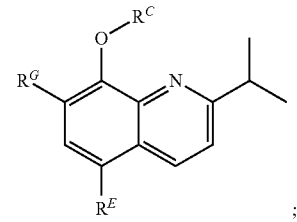

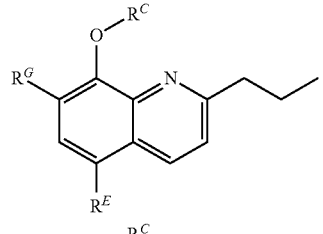

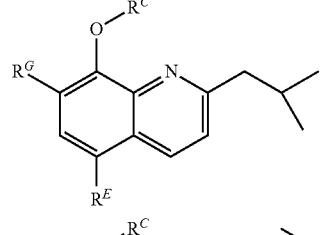

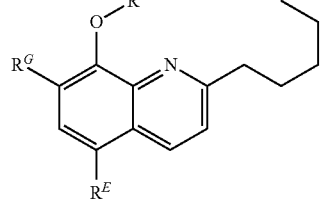

or a pharmaceutically acceptable salt, solvate, hydrate, polymorph, co-crystal, tautomer, stereoisomer, isotopically labeled derivative, or prodrug thereof.

Additional exemplary compounds of the invention also include, but are not limited to:

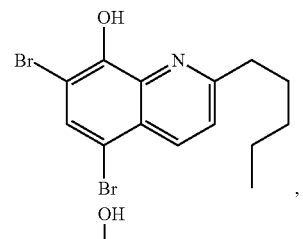

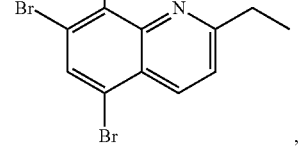

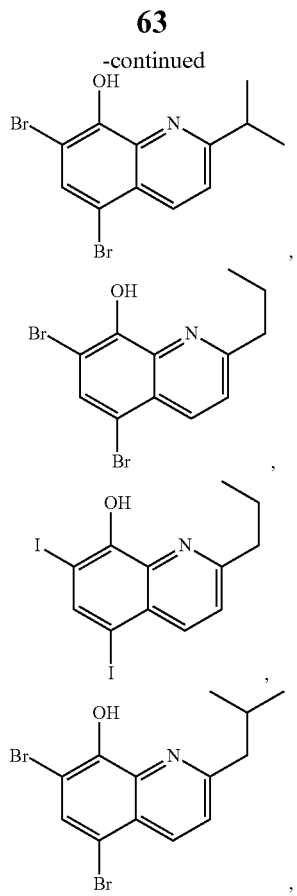

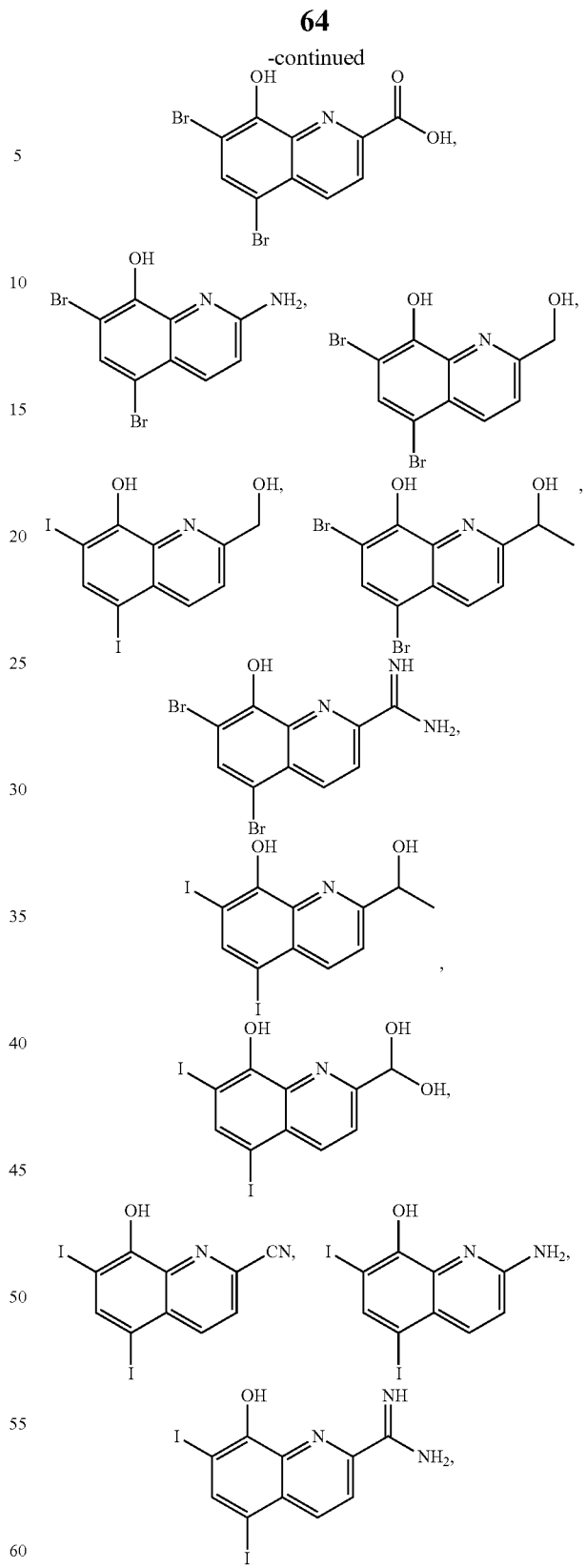

and pharmaceutically acceptable salts, solvates, hydrates, polymorphs, co-crystals, tautomers, stereoisomers, isotopically labeled derivatives, and prodrugs thereof.

Additional exemplary compounds of the invention also include, but are not limited to:

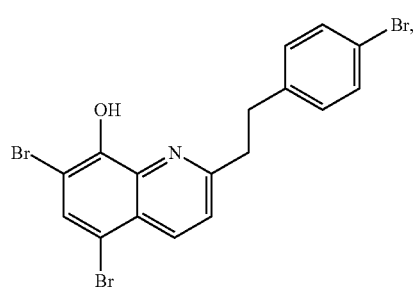 [SMILES: Oc1c(Br)cc(Br)c2ccc(CCc3ccc(Br)cc3)nc12]

and pharmaceutically acceptable salts, solvates, hydrates, polymorphs, co-crystals, tautomers, stereoisomers, isotopically labeled derivatives, and prodrugs thereof.

Additional exemplary compounds of the invention also include, but are not limited to:

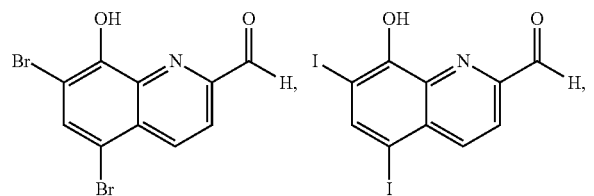

and pharmaceutically acceptable salts, solvates, hydrates, polymorphs, co-crystals, tautomers, stereoisomers, isotopically labeled derivatives, and prodrugs thereof.

In certain embodiments, the compounds of the invention are the compounds of Formula (I), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (I), and pharmaceutically acceptable salts thereof.

In certain embodiments, the compounds of the invention are the compounds of Formula (I'), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (I'), and pharmaceutically acceptable salts thereof.

In certain embodiments, the compounds of the invention are the compounds of Formula (I'-c), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (I'-c), and pharmaceutically acceptable salts thereof.

In certain embodiments, the compounds of the invention are substantially pure. In certain embodiments, a compound of the invention is at least about 90%, at least about 95%, at least about 97%, at least about 98%, at least about 99%, or at least about 99.5% free of impurities.

The compounds of the invention have been found to be antimicrobial agents (e.g., antibacterial agents). The activity of a compound of the invention against a microorganism may be measured by the minimum inhibitory concentration (MIC) of the compound in inhibiting the viability, growth, or replication of the microorganism. In certain embodiments, the MIC of a compound of the invention is an MIC in inhibiting the viability the microorganism. In certain embodiments, the MIC value of an inventive compound in inhibiting a microorganism is at most about 1 nM, at most about 3 nM, at most about 10 nM, at most about 30 nM, at most about 100 nM, at most about 300 nM, at most about 1 µM, at most about 3 µM, at most about 10 µM, at most about 30 µM, or at most about 100 µM. In certain embodiments, the MIC value of an inventive compound in inhibiting a microorganism is at least about 1 nM, at least about 3 nM, at least about 10 nM, at least about 30 nM, at least about 100 nM, at least about 300 nM, at least about 1 µM, at least about 3 µM, at least about 10 µM, or at least about 30 µM. In certain embodiments, MIC values are measured according to the guidelines of the Clinical and Laboratory Standards Institute (CLSI) (which is incorporated herein by reference) (e.g., a broth microdilution method). In certain embodiments, MIC values are measured by a method described herein.

The activity of a compound of the invention against a microorganism may also be measured by the minimum bactericidal concentration (MBC) of the compound in killing the microorganism. In certain embodiments, the MBC value of an inventive compound in killing a microorganism is at most about 3 nM, at most about 10 nM, at most about 30 nM, at most about 100 nM, at most about 300 nM, at most about 1 µM, at most about 3 µM, at most about 10 µM, at most about 30 µM, at most about 100 µM, or at most about 300 µM. In certain embodiments, the MBC value of an inventive compound in killing a microorganism is at least about 3 nM, at least about 10 nM, at least about 30 nM, at least about 100 nM, at least about 300 nM, at least about 1 µM, at least about 3 µM, at least about 10 µM, at least about 30 µM, or at least about 100 µM. In certain embodiments, the MBC values are determined by broth dilution MIC tests by subculturing to agar plates that do not contain the test compound. In certain embodiments, the MBC values are determined by a method described herein.

The activity of a compound of the invention in reducing or removing a biofilm may be measured by the minimum biofilm eradication concentration (MBEC) of the compound. In certain embodiments, the MBEC value of an inventive compound in killing a microorganism is at most about 30 nM, at most about 100 nM, at most about 300 nM, at most about 1 µM, at most about 3 µM, at most about 10 µM, at most about 30 µM, at most about 100 µM, at most about 300 µM, at most about 1 mM, or at most about 2 mM. In certain embodiments, the MBEC value of an inventive compound in killing a microorganism is at least about 30 nM, at least about 100 nM, at least about 300 nM, at least about 1 µM, at least about 3 µM, at least about 10 µM, at least about 30 µM, at least about 100 µM, or at least about 1 mM. In certain embodiments, the MBEC values are determined by a method described herein.

The compounds of the invention may selectively inhibit the growth and/or reproduction of or kill a microorganism. In certain embodiments, a compound of the invention is more active in inhibiting the growth and/or reproduction of or killing a first microorganism (e.g., a microorganism described herein) than in inhibiting the growth and/or reproduction of or killing a host cell. In certain embodiments, a compound of the invention is more active in inhibiting the growth and/or reproduction of or killing a first microorganism than in inhibiting the growth and/or reproduction of or killing a second microorganism. The selectivity of an inventive compound in inhibiting the growth and/or reproduction of or killing a first microorganism over a host cell or a second microorganism may be determined by the quotient of the MIC, MBC, or MBEC value of the inventive compound in inhibiting the growth and/or reproduction of or killing the host cell or second microorganism over the MIC, MBC, or MBEC value of the inventive compound in inhibiting the growth and/or reproduction of or killing the first microorganism. The selectivity of an inventive compound in inhibiting the growth and/or reproduction of or killing a first microorganism over a host cell or a second microorganism may also be determined by the quotient of the MIC, MBC, or MBEC value of the inventive compound in inhibiting the growth and/or reproduction of or killing the host cell or second microorganism over the MIC, MBC, or MBEC value of the inventive compound in inhibiting the growth and/or reproduction of or killing the first microorganism. In certain embodiments, the selectivity of an inventive compound in inhibiting the growth and/or reproduction of or killing a first microorganism over a host cell or a second microorganism is at least about 3-fold, at least about 10-fold, at least about 30-fold, at least about 100-fold, at least about 1,000-fold, at least about 10,000-fold, or at least about 100,000-fold.

The compounds of the invention may show low cytotoxicity toward mammalian cells (e.g., cytotoxicity $IC_{50}$ against HeLa cells being greater than 100 µM). The compounds of the invention may show low hemolysis activity (e.g., not more than 1%, not more than 2%, not more than 4%, not more than 6%, not more than 10%, or not more than 22% hemolysis of red blood cells when treated with the compound at 200 µM).

Methods of Preparing the Compounds

Compounds of the invention may be prepared using reductive amination esterification, or alkylation reactions. In another aspect, the present disclosure also provides methods of preparing the compounds of the invention. In certain embodiments, described herein are methods of preparing the compounds of Formula (I), and salts thereof (Method A), the methods including contacting a compound of Formula (B):

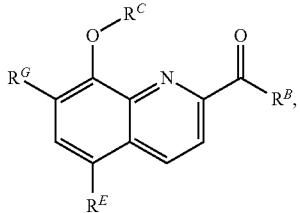
(B)

or a salt thereof, with an amine of Formula (C):

(C)

or a salt thereof, in the presence of a reductant to provide the compound of Formula (I), or salt thereof.

In certain embodiments, described herein are methods of preparing the compounds of Formula (I) (Method B), and salts thereof, the methods including contacting an imine of Formula (D):

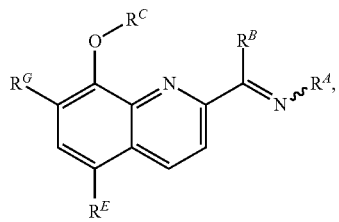
(D)

or a salt thereof, with a reductant to provide the compound of Formula (I), or salt thereof.

In certain embodiments, Method B further comprises contacting a compound of Formula (B):

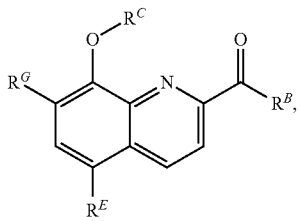
(B)

or a salt thereof, with an amine of Formula (C):

(C)

or a salt thereof, to provide the imine of Formula (D), or salt thereof.

In certain embodiments, Method A and/or Method B further comprise contacting a compound of Formula (A1):

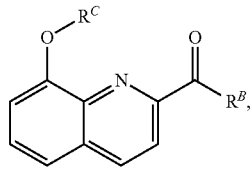
(A1)

or a salt thereof, with a halogenating agent to provide the compound of Formula (B), or salt thereof.

In certain embodiments, Method A and/or Method B further comprise contacting a compound of Formula (A2):

(A2)

or a salt thereof, with an oxidant to provide the compound of Formula (B), or salt thereof.

In another aspect, the present invention provides methods of preparing the compounds of the invention. In certain embodiments, described herein are methods of preparing the compounds of Formula (I'-b), and salts thereof (Method C):

(I'-b)

the methods including contacting a compound of Formula (B):

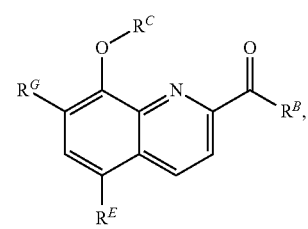
(B)

or a salt thereof, with an amine of Formula (E):

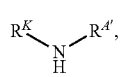
(E)

or a salt thereof, in the presence of a reductant to provide the compound of Formula (I'-b), or salt thereof.

In certain embodiments, described herein are methods of preparing the compounds of Formula (I'-b) (Method D), and salts thereof:

(I'-b)

the methods including contacting an iminium ion of Formula (F):

(F)

or a salt thereof, with a reductant to provide the compound of Formula (I'-b), or salt thereof.

In certain embodiments, Method D further comprises contacting a compound of Formula (B):

(B)

or a salt thereof, with an amine of Formula (E):

(E)

or a salt thereof, to provide the iminium ion of Formula (F), or salt thereof.

In certain embodiments, Method C and/or Method D further comprise contacting a compound of Formula (A1):

(A1)

or a salt thereof, with a halogenating agent to provide the compound of Formula (B), or salt thereof.

In certain embodiments, Method C and/or Method D further comprise contacting a compound of Formula (A2):

(A2)

or a salt thereof, with an oxidant to provide the compound of Formula (B), or salt thereof.

In another aspect, the present invention provides methods of preparing the compounds of the invention. In certain embodiments, described herein are methods of preparing the compounds of Formula (G), and salts thereof (Method E):

(G)

the methods including contacting a compound of Formula (H):

(H)

or a salt thereof, with a base and an halide of Formula (J):

(J)

or a salt thereof, to provide the compound of Formula (G), or salt thereof.

In another aspect, the present invention provides methods of preparing the compounds of the invention. In certain embodiments, described herein are methods of preparing the compounds of Formula (G), and salts thereof (Method E):

(G)

the methods including contacting a compound of Formula (H'):

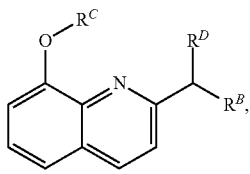

(H')

or a salt thereof, with a base and an halide of Formula (J):

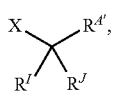

(J)

or a salt thereof, to provide the compound of Formula (G), or salt thereof.

In certain embodiments, Method E further comprises contacting a compound of Formula (G):

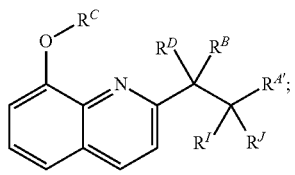

(G)

or a salt thereof, with a halogenating agent to provide the compound of Formula (I'-a):

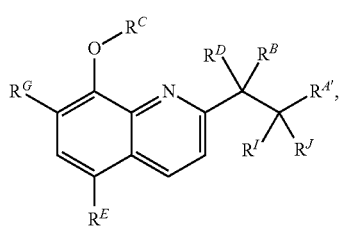

(I'-a)

or salt thereof.

In certain embodiments, the oxidant useful in a method of preparing is SeO$_2$. In certain embodiments, the oxidant useful in a method of preparing is chromium(VI) (e.g., CrO$_3$-pyridine complex; CrO$_3$ and 3,5-dimethylpyrazole; pyridinium chlorochromate (PCC); pyridinium dichromate (PDC); PDC-tert-butyl hydroperoxide; sodium chromate; sodium dichromate; pyridinium fluorochromate; 3,5-dimethylpyrazolium fluorochromate (VI); and a combination of an N-hydroxydicarboxylic acid imide with a chromium(VI)-containing oxidant), manganese dioxide, potassium permanganate, alkyl hydroperoxide (e.g., tert-butyl hydroperoxide) in the presence of a metal catalyst, oxygen in the presence of N-hydroxyphthalimide (NHPI) and a free-radical initiator, sodium chlorite in the presence of tert-butyl hydroperoxide, or sodium chlorite in the presence of N-hydroxyphthalimide. In certain embodiments, the oxidant useful in a method of preparing is commercially available.

In certain embodiments, the reductant useful in a method of preparing is a borohydride (e.g., sodium borohydride, potassium borohydride, calcium borohydride, magnesium borohydride, tetramethylammonium borohydride, tetraethylammonium borohydride, tetrabutylammonium borohydride, methyltrioctylammonium borohydride, cetyltrimethylammonium borohydride, bis(triphenylphosphine)copper(I) borohydride, potassium tri(1-pyrazolyl)borohydride, potassium tri(3,5-dimethyl-1-pyrazolyl)borohydride, sodium cyanoborohydride, sodium triacetoxyborohydride (NaBH(OAc)$_3$), or polymer-supported borohydride). In certain embodiments, the reductant useful in a method of preparing is NaBH(OAc)$_3$. In certain embodiments, the reductant useful in a method of preparing is a borane (e.g., a borane tetrahydrofuran complex, borane dimethyl sulfide complex, borane dimethylamine complex, borane pyridine complex, borane trimethylamine complex, borane triethylamine complex, borane morpholine complex, borane tert-butylamine complex, borane-ammonia complex, borane triphenylphosphine complex, borane N,N-diethylaniline complex, borane di(tert-butyl)phosphine complex, borane diphenylphosphine complex, borane 4-methylmorpholine complex, borane N,N-diisopropylethylamine complex, borane isoamylsulfide complex, borane ethylenediamine complex, acetylthiomethyl-diphenylphosphine borane complex, 2-methylpyridine borane complex, tert-butyldimethylphosphine borane, 5-ethyl-2-methylpyridine borane complex, lithium ammonia borane, (11bR)-4,5-dihydro-3H-dinaphtho[2,1-c:1',2'-e]phosphepine borane, (methoxycarbonyl)borane trimethylamine complex, dibromoborane dimethyl sulfide complex, mono-bromoborane methyl sulfide complex, dichloroborane methyl sulfide complex, 1,3-dimethylimidazol-2-ylidene borane). In certain embodiments, the reductant useful in a method of preparing is a silane. In certain embodiments, the silane is of the formula: HSi(R$^3$)$_3$, wherein each instance of R$^3$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or —OR$^{3a}$, wherein each instance of R$^{3a}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group). In certain embodiments, the silane is a monoalkylsilane (e.g., BuSiH$_3$), dialkylsilane (e.g., Et$_2$SiH$_2$), trialkylsilane (e.g., Me$_3$SiH or Et$_3$SiH). In certain embodiments, the silane is a poly(alkylhydrosiloxane) (e.g., poly(methylhydrosiloxane) (PMHS)). In certain embodiments, the reductant useful in a method of preparing is an alcohol. In certain embodiments, the alcohol is of the formula: (R$^2$)$_2$CHOH, wherein each instance of R$^2$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, the alcohol is methanol, ethanol, propanol (e.g., isopropanol), or butanol. In certain embodiments, the reductant useful in a method of preparing is H$_2$. In certain embodiments, the reductant useful in a method of preparing is commercially available.

In certain embodiments, the halogenating agent useful in a method of preparing is a fluorinating agent (e.g., antimony trifluoride, arsenic trifluoride, bromine pentafluoride, bromine trifluoride, chlorine monofluoride, chlorine pentafluoride, chlorine trifluoride, cobalt(III) fluoride, cyanuric fluoride, diethylaminosulfur trifluoride, fluorine, fluorosulfuric acid, gold(III) fluoride, iodine pentafluoride, ishikawa reagent, manganese(III) fluoride, manganese(IV) fluoride, nitrosyl fluoride, nitryl fluoride, perchloryl fluoride, platinum hexafluoride, selenium tetrafluoride, silver(II) fluoride, sulfur tetrafluoride, xenon difluoride, xenon hexafluoride), chlorinating agent (e.g., N-chlorosuccinimide (NCS), chlorine), brominating agent (e.g., N-bromosuccinimide (NBS), bromine, pyrrolidone hydrotribromide, trimethylsilyl bromide, phosphorus oxybromide, phosphorus tribromide, bromine chloride, aluminum tribromide, pyridinium tribromide), or iodinating agent (e.g., N-iodosuccinimide (NIS), iodine, 1,3-diiodo-5,5-dimethylhydantoin (DIH), N-iodosaccharin, bis(pyridine)iodonium tetrafluoroborate ($IPy_2BF_4$), benzyltrimethylammonium dichloroiodate ($BTMA\ ICl_2$), pyridinium iodo-chloride (PyICl)).

In certain embodiments, the base useful in a method of preparing is 9-azajulolidine, barium tert-butoxide, benzyltrimethylammonium hydroxide, n-butyllithium, sec-butyllithium, tert-butyllithium, butylmagnesium chloride, sec-butylmagnesium chloride, tert-butylmagnesium chloride, 2-tert-butyl-1,1,3,3-tetramethylguanidine, 2-(2-chloro-6-fluorophenyl)ethylamine hydrochloride, choline hydroxide, Dabco® 33-LV, 1,5-diazabicyclo[4.3.0]non-5-ene, 1,4-diazabicyclo[2.2.2]octane, 1,8-diazabicyclo[5.4.0]undec-7-ene, diethylamine, diisopropylamine, diisopropylmethylamine, dimethylamine, 4-(dimethylamino)pyridine, 1,1-dimethylpropylmagnesium chloride, 2,2-dimethylpropylmagnesium chloride, ethylamine, diisopropylethylamine, lithiumdiisopropylamide (LDA), 2-(ethylhexyl)lithium, ethyllithium, ethylmagnesium bromide, ethylmagnesium chloride, hexadecyltrimethylammonium hydroxide, hexamethonium hydroxide, hexyllithium, hexylmagnesium bromide, hexylmagnesium chloride, isobutyllithium, isobutylmagnesium bromide, isobutylmagnesium chloride, isopropyllithium, lithium amide, lithium tert-amoxide, lithium bis(trimethylsilyl)amide, lithium tert-butoxide, lithium dicyclohexylamide, lithium diethylamide, lithium dimethylamide, lithium ethoxide, lithium isopropoxide, lithium methoxide, lithium 2,2,6,6-tetramethylpiperidide, lithium trimethylsilanolate, 2,6-lutidine, magnesium bis(diisopropyl)amide, magnesium bis(hexamethyldisilazide), magnesium di-tert-butoxide, magnesium ethoxide, magnesium methoxide, methylamine, methyllithium, methylmagnesium bromide, methylmagnesium chloride, methylmagnesium iodide, pentylmagnesium bromide, pentylmagnesium chloride, piperazine, piperidine, potassium bis(trimethylsilyl)amide, potassium tert-butoxide, potassium ethoxide, potassium methoxide, potassium tert-pentoxide, potassium trimethylsilanolate, propylmagnesium chloride, Proton-Sponge®, pyridine, sodium bis(trimethylsilyl)amide, sodium tert-butoxide, sodium ethoxide, sodium methoxide, sodium tert-pentoxide, sodium trimethylsilanolate, tetrabutylammonium hydroxide, tetrabutylammonium methoxide, tetraethylammonium hydroxide, tetrahexylammonium hydroxide, tetrakis(decyl)ammonium hydroxide, tetramethylammonium hydroxide, 2,2,6,6-tetramethylpiperidine, tetraoctylammonium hydroxide, tetrapentylammonium hydroxide, tetrapropylammonium hydroxide, 1,5,7-triazabicyclo[4.4.0]dec-5-ene, triethylamine, triethylmethylammonium hydroxide, 2,8,9-triisobutyl-2,5,8,9-tetraaza-1-phosphabicyclo[3.3.3]undecane, 2,8,9-triisobutyl-2,5,8,9-tetraaza-1-phosphabicyclo[3.3.3] undecane, 2,8,9-triisopropyl-2,5,8,9-tetraaza-1-phosphabicyclo[3.3.3]undecane, trimethylphenylammonium hydroxide, 2,8,9-trimethyl-2,5,8,9-tetraaza-1-phosphabicyclo[3.3.3]undecane, sodium hydride, potassium hydride.

The step(s) of the methods of preparing may be performed under any suitable conditions. A suitable condition is a combination of physical and chemical parameters under which an intended product (e.g., a compound of the invention, an intermediate useful in preparing a compound of the invention) or intermediate may be formed using the methods.

A suitable condition may include the absence of a solvent (i.e., neat). A suitable condition may include a suitable solvent. In certain embodiments, the suitable solvent is an organic solvent. In certain embodiments, the suitable solvent is an aprotic organic solvent (e.g., acetonitrile, N,N-dimethylformamide (DMF), N,N-dimethylacetamide (DMA), N-methyl-2-pyrrolidone (NMP), dimethyl sulfoxide (DMSO), tetrahydrofuran (THF), 2-methly-tetrahydrofuran, tetrahydropyran, 1,4-dioxane, diethyl ether, methyl t-butyl ether (MTBE), dimethoxyethane (DME), diglyme, acetone, butanone, dichloromethane, chloroform, carbon tetrachloride, 1,2-dichloroethane, benzene, toluene, xylene). In certain embodiments, the suitable solvent is 1,2-dichloroethane. In certain embodiments, the suitable solvent is 1,4-dioxane. In certain embodiments, the suitable solvent is a protic organic solvent (e.g., an alcohol (e.g., methanol, ethanol, propanol, butanol), acetic acid). In certain embodiments, the suitable solvent is an inorganic solvent (e.g., water). In certain embodiments, the suitable solvent is a mixture of two or more solvents. In certain embodiments, the suitable solvent is commercially available.

A suitable condition may also include a suitable temperature under which a step of a method of preparing is performed. In certain embodiments, the suitable temperature is at least about 0° C., at least about 21° C., at least about 40° C., at least about 60° C., at least about 80° C., or at least about 100° C. In certain embodiments, the suitable temperature is at most about 100° C., at most about 80° C., at most about 60° C., at most about 40° C., at most about 21° C., or at most about 0° C. Combinations of the above-referenced ranges (e.g., at least about 21° C. and at most about 40° C.) are also within the scope of the disclosure. A suitable temperature may be a variable temperature (e.g., from 21° C. to about 40° C.) during a step of a method of preparing. In certain embodiments, the suitable temperature is about 21° C. (room temperature). In certain embodiments, the suitable solvent is 1,2-dichloroethane, and the suitable temperature is about 21° C. In certain embodiments, the suitable temperature is about 80° C. In certain embodiments, the suitable temperature is about 80° C., and the suitable time duration is about 8 hours.

A suitable condition may also include a suitable pressure under which a step of a method of preparing is performed. In certain embodiments, the suitable pressure is about 1 atmosphere.

A suitable condition may also include a suitable atmosphere under which a step of a method of preparing is performed. In certain embodiments, the suitable atmosphere is air. In certain embodiments, the suitable atmosphere is an inert atmosphere. In certain embodiments, the suitable atmosphere is a nitrogen or argon atmosphere.

A suitable condition may also include a suitable time duration that a step of a method of preparing lasts. In certain embodiments, the suitable time duration is in the order of minutes (e.g., about 15 minutes or about 30 minutes), hours (e.g., about 1 hour, about 2 hours, about 3 hours, about 4 hours, about 6 hours, about 8 hours, or about 12 hours), or days (e.g., about 1 day or 2 days). In certain embodiments, the suitable time duration is between 6 hours and 1 day. In certain embodiments, the suitable time duration is between 15 minutes and 1 hour. In certain embodiments, the suitable time duration is about 8 hours.

One or more intermediates resulting from a step of a method of preparing may be isolated and/or purified, and the isolated and/or purified intermediates may be reacted in a next step of the method. The isolated and/or purified intermediates may be substantially free of impurities or may contain one or more other components, such as reagents and solvents employed in the step yielding the intermediates, and byproducts. The intermediates may also be reacted in a next step without being isolated and/or purified. The intermediates and/or intended products of a method of preparing may be isolated and/or purified using methods known in the art, such as distillation, chromatography (e.g., normal phase chromatography (e.g., silica gel flash chromatography), reverse phase chromatography (e.g., high performance liquid chromatography (HPLC)), precipitation, decanting, filtration, centrifuge, trituration, crystallization, recrystallization, liquid-liquid phase separation, evaporation, and drying. In certain embodiments, an intended product described herein is substantially pure (e.g., substantially free of impurities) (e.g., at least about 90%, at least about 95%, at least about 98%, at least about 99%, at least about 99.5%, at least about 99.9%, or more pure) prior to or without purification.

Compositions, Kits, and Administration

The present invention also provides compositions (e.g., pharmaceutical compositions) comprising a compound of the invention (e.g., a compound of Formula (I), or pharmaceutically acceptable salts thereof), and optionally an excipient (e.g., pharmaceutically acceptable excipient).

The present invention also provides compositions (e.g., pharmaceutical compositions) comprising a compound of the invention (e.g., a compound of Formula (I'), or pharmaceutically acceptable salts thereof), and optionally an excipient (e.g., pharmaceutically acceptable excipient).

In certain embodiments, a composition of the invention is useful for disinfecting a surface. In certain embodiments, the compound of the invention is provided in an effective amount in the composition. In certain embodiments, the amount of the compound included in the composition is effective for killing at least 80%, at least 90%, at least 95%, at least 99%, at least 99.9%, or at least 99.99% of the microorganisms on the surface. In certain embodiments, the amount of the compound included in the composition is effective for killing at most 90%, at most 95%, at most 99%, at most 99.9%, at most 99.99%, or at most 99.999% of the microorganisms on the surface. A composition of the invention may include one or more excipients (e.g., water, detergent, bleach, surfactant) (e.g., pharmaceutically acceptable excipients).

In certain embodiments, a composition of the invention is a pharmaceutical composition comprising a compound of the invention and optionally a pharmaceutically acceptable excipient. In certain embodiments, the compound of the invention is provided in an effective amount in the pharmaceutical composition. In certain embodiments, the effective amount of the compound is a therapeutically effective amount. In certain embodiments, the effective amount of the compound is a prophylactically effective amount. The pharmaceutical compositions of the invention may be useful in the inventive methods. In certain embodiments, the pharmaceutical compositions are useful in treating a microbial infection (e.g., a bacterial infection). In certain embodiments, the pharmaceutical compositions are useful in preventing a microbial infection (e.g., a bacterial infection). In certain embodiments, the pharmaceutical compositions are useful in inhibiting the growth of a microorganism (e.g., a microorganism described herein). In certain embodiments, the pharmaceutical compositions are useful in inhibiting the reproduction of a microorganism. In certain embodiments, the pharmaceutical compositions are useful in killing a microorganism. In certain embodiments, the pharmaceutical compositions are useful in inhibiting the formation and/or growth of a biofilm. In certain embodiments, the pharmaceutical compositions are useful in reducing or removing a biofilm. In certain embodiments, the pharmaceutical compositions are useful in disinfecting a surface. In certain embodiments, the pharmaceutical compositions are useful in cleaning a surface.

Pharmaceutical compositions described herein can be prepared by any method known in the art of pharmacology. In general, such preparatory methods include the steps of bringing the compound of the invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a microbial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Jet injection devices which deliver liquid vaccines to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil-in-water and/or water-in-oil emulsions such as creams, ointments, and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets, and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is about 70 kg.

It will be also appreciated that a compound or composition, as described herein, can be administered in combination with one or more additional pharmaceutical agents. In certain embodiments, the additional pharmaceutical agent is different from a compound of the invention, or a pharmaceutically acceptable salt, solvate, hydrate, polymorph, co-crystal, tautomer, stereoisomer, isotopically labeled derivative, or prodrug thereof. The compounds or compositions can be administered in combination with additional pharmaceutical agents to improve their potency, efficacy, and/or bioavailability, reduce and/or modify their metabolism, inhibit their excretion, and/or modify their distribution within the body. It will also be appreciated that the therapy employed may achieve a desired effect for the same disorder, and/or it may achieve different effects. In certain embodiments, the combination of a compound of the invention and an additional pharmaceutical agent shows a synergistic effect.

The compound or composition can be administered concurrently with, prior to, or subsequent to, one or more additional pharmaceutical agents, which are different from the compound or composition and may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents in combination be utilized at levels that do not exceed the levels at which they are utilized individually. In some embodiments, the levels utilized in combination will be lower than those utilized individually.

Exemplary additional pharmaceutical agents include, but are not limited to, antibiotics (e.g., antibacterial agents, antiviral agents, anti-fungal agents), anti-inflammatory agents, anti-pyretic agents, and pain-relieving agents. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is an antibiotic. In certain embodiments, the additional pharmaceutical agent is an antibiotic effective against a microorganism described herein. In certain embodiments, the additional pharmaceutical agent is an antibiotic effective against a bacterium. In certain embodiments, the additional pharmaceutical agent is an antibiotic effective against a Gram-positive bacterium (e.g., a *Staphylococcus* species or *Enterococcus* species). In certain embodiments, the additional pharmaceutical agent is an antibiotic effective against a Gram-negative bacterium (e.g., an *Acinetobacter* species). In certain embodiments, the additional pharmaceutical agent is an antibiotic effective against a multidrug-resistant bacterium. In certain embodiments, the additional pharmaceutical agent is a β-lactam antibiotic. In certain embodiments, the additional pharmaceutical agent is a penicillin (i.e., a penam, such as an aminopenicillin (e.g., amoxicillin, an ampicillin (e.g., pivampicillin, hetacillin, bacampicillin, metampicillin, talampicillin), epicillin), a carboxypenicillin (e.g., a carbenicillin (e.g., carindacillin), ticarcillin, temocillin), a ureidopenicillin (e.g., azlocillin, piperacillin, mezlocillin), a mecillinam (e.g., pivmecillinam), sulbenicillin, benzylpenicillin, clometocillin, benzathine benzylpenicillin, procaine benzylpenicillin, azidocillin, penamecillin, phenoxymethylpenicillin, propicillin, benzathine phenoxymethylpenicillin, pheneticillin, a cloxacillin (e.g., dicloxacillin, flucloxacillin), oxacillin, methicillin, nafcillin), a penem (e.g., faropenem), a carbapenem (e.g., biapenem, ertapenem, an antipseudomonal (e.g., doripenem, imipenem, meropenem), panipenem), a cephalosporin (i.e., a cephem, such as cefazolin, cefacetrile, cefadroxil, cefalexin, cefaloglycin, cefalonium, cefaloridine, cefalotin, cefapirin, cefatrizine, cefazedone, cefazaflur, cefradine, cefroxadine, ceftezole, cefaclor, cefamandole, cefminox, cefonicid, ceforanide, cefotiam, cefprozil, cefbuperazone, cefuroxime, cefuzonam, a cephamycin (e.g, cefoxitin, cefotetan, cefmetazole), a carbacephem (e.g., loracarbef), cefixime, ceftriaxone, an antipseudomonal (e.g., ceftazidime, cefoperazone), cefcapene, cefdaloxime, cefdinir, cefditoren, cefetamet, cefmenoxime, cefodizime, cefotaxime, cefpimizole, cefpiramide, cefpodoxime, cefsulodin, cefteram, ceftibuten, ceftiolene, ceftizoxime, an oxacephem (e.g., flomoxef, latamoxef), cefepime, cefozopran, cefpirome, cefquinome, ceftobiprole, ceftaroline fosamil, ceftiofur, cefquinome, cefovecin), a monobactam (e.g., aztreonam, tigemonam, carumonam, nocardicin A), an aminoglycoside (e.g., amikacin, gentamicin, kanamycin, neomycin, netilmicin, tobramycin, paromomycin, spectinomycin), an ansamycin (e.g., geldanamycin, herbimycin, rifaximin), a glycopeptide (e.g., teicoplanin, vancomycin, telavancin), a lincosamide (e.g., clindamycin, lincomycin), a lipopeptide (e.g., daptomycin), a macrolide (e.g., azithromycin, clarithromycin, dirithromycin, erythromycin, roxithromycin, troleandomycin, telithromycin, spiramycin), a nitrofuran (e.g., furazolidone, nitrofurantoin), an oxazolidonone (e.g., linezolid, posizolid, radezolid, torezolid), a polypeptide (e.g., bacitracin, colistin, polymyxin B), a quinolone (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin), a sulfonamide (e.g., mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim, sulfonamidochrysoidine), a tetracycline (e.g., demeclocycline, doxycycline, minocycline, oxytetracycline, tetracycline), clofazimine, dapsone, capreomycin, cycloserine, ethambutol, ethionamide, isoniazid, pyrazinamide, rifampin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, or trimethoprim. In certain embodiments, the additional pharmaceutical agent is an antiviral agent. In certain embodiments, the additional pharmaceutical agent is (–)-Oseltamivir, B-D-ribofuranose, 1-acetate 2,3,5-tribenzoate, 1-Docosanol, 2-Amino-6-chloropurine, 5-Iodo-2'-deoxyuridine, 6-Chloropurine, Abacavir sulfate, Abacavir-epivir mixt., Acyclovir, Acyclovir sodium, Adefovir dipivoxil, Amantadine (e.g., Amantadine hydrochloride), Amantadine hydrochloride, anti-HIV agent (e.g., Abacavir, Amprenavir, Atazanavir, Azidothymidine, Bryostatin (e.g., Bryostatin 1, Bryostatin 10, Bryostatin 11, Bryostatin 12, Bryostatin 13, Bryostatin 14, Bryostatin 15, Bryostatin 16, Bryostatin 17, Bryostatin 18, Bryostatin 19, Bryostatin 2, Bryostatin 20, Bryostatin 3, Bryostatin 4, Bryostatin 5, Bryostatin 6, Bryostatin 7, Bryostatin 8, Bryostatin 9), Dideoxycytidine, Dideoxyinosine, Efavirenz, Indinavir, Lamivudine, Lopinavir, Nevirapine, Ritonavir, Saquinavir, Stavudine, Tenofovir), Azauridine, ombivir, Deoxynojirimycin, Docosanol, Fomivirsen sodium, Foscarnet, Ganciclovir, Integrase inhibitors (e.g., 5CITEP, Chloropeptin I, Complestatin, Dolutegravir, Elvitegravir, L 708906, L 731988, MK 2048, Raltegravir, Raltegravir potassium), MK 5172, MK 8742, Palivizumab, Pegylated interferon alfa-2b, Phosphonoacetic acid, Ribavirin, Simeprevir, Sofosbuvir, Tubercidin, Vidarabine, or virus entry inhibitor (e.g., Enfuvirtide, Maraviroc). In certain embodiments, the additional pharmaceutical agent is a fungicide. In certain embodiments, the additional pharmaceutical agent is (–)-Fumagillin, (–)-Metalaxyl, 1,2, 5-Fluorocytosine, Acrisorcin, Anilazine, Antifouling agent, Azoxystrobin, Benomyl, Bordeaux mixture, Captan, Carbendazim, Caspofungin acetate, Chlorothalonil, Clotrimazole, Dichlofluanid, Dinocap, Dodine, Fenhexamid, Fenpropimorph, Ferbam, Fluconazole, Fosetyl A1, Griseofulvin, Guanidine (e.g., Agmatine, Amiloride hydrochloride, Biguanide (e.g., Imidodicarbonimidic diamide, N,N-dimethyl-,hydrochloride (1:1) (e.g., Metformin hydrochloride), Metformin), Cimetidine, Guanethidine, Guanfacine, Guanidine, Guanidinium, Methylguanidine, Sulfaguanidine), Iprobenfos, Iprodione, Isoprothiolane, Itraconazole, Ketoconazole, Mancozeb, Metalaxyl, Metiram, Miconazole, Natamycin, Nystatin, Oxycarboxine, Pentachloronitrobenzene, Prochloraz, Procymidone, Propiconazole, Pyrazophos, Reduced viscotoxin A3, Salicylanilide, Tebuconazole, Terbinafine, Thiabendazole, Thiophanate, Thiophanate methyl, Triadimefon, Vinclozolin, or Voriconazole. In certain embodiments, the additional pharmaceutical agent is a protozoacide. In certain embodiments, the additional pharmaceutical agent is Amebicide, Antimalarial (e.g., Artemisinin, Chloroquine (e.g., Chloroquine phosphate), Mefloquine, Sulfadoxine), Coccidiostat, Leishmanicide, Trichomonacide, or Trypanosomicide (e.g., Eflornithine). In certain embodiments, the additional pharmaceutical agent is a parasiticide. In certain embodiments, the additional pharmaceutical agent is anti-helmintic (e.g., Abamectin, Dimethylformocarbothialdine, Niclosamide, Schistosomicide), protozoacide (e.g., Amebicide, antimalarial (e.g., Artemisinin, chloroquine (e.g., chloroquine phosphate), Mefloquine, Sulfadoxine), coccidiostat, leishmanicide, trichomonacide, or trypanosomicide (e.g., Eflornithine)). In certain embodiments, the additional pharmaceutical agent is an iron chelator (e.g., iron(II) chelator, iron(III) chelator). In certain embodiments, the additional pharmaceutical agent is 2,2'-bipyridyl, deferoxamine, deferiprone, or deferasirox. In certain embodiments, the additional pharmaceutical agent is a combination of two or more additional pharmaceutical agents described herein (e.g., a combination of an antibiotic and an iron chelator). In certain embodiments, the additional pharmaceutical agent is commercially available.

Also encompassed by the invention are kits (e.g., pharmaceutical packs). The kits provided may comprise a compound or composition (e.g., pharmaceutical composition) of the invention and a container (e.g., a vial, ampule, bottle, syringe, dispenser package, tube, inhaler, and/or other suitable container). In some embodiments, a kit of the invention further includes a second container comprising an excipient (e.g., pharmaceutically acceptable excipient) for dilution or suspension of an inventive compound or composition. In some embodiments, the compound or composition of the invention provided in a first container and a second container are combined to form one unit dosage form.

In one aspect, the present invention provides kits including a first container comprising a compound or composition of the invention. In certain embodiments, a kit of the invention includes a first container comprising a compound of Formula (I), or a pharmaceutically acceptable salt thereof, or a composition thereof. In certain embodiments, a kit of the invention includes a first container comprising a compound of Formula (I'), or a pharmaceutically acceptable salt thereof, or a composition thereof.

In certain embodiments, the kits are useful in treating a microbial infection in a subject in need thereof. In certain embodiments, the kits are useful in preventing a microbial infection in a subject in need thereof. In certain embodiments, the microbial infection is a bacterial infection. In certain embodiments, the bacterial infection is an infection caused by a Gram-positive bacterium. In certain embodiments, the bacterial infection is an infection caused by a Gram-negative bacterium. In certain embodiments, the kits are useful in inhibiting the growth of a microorganism. In certain embodiments, the kits are useful in inhibiting the reproduction of a microorganism. In certain embodiments, the kits are useful in killing a microorganism. In certain embodiments, the kits are useful in inhibiting the formation and/or growth of a biofilm. In certain embodiments, the kits are useful in reducing or removing a biofilm. In certain embodiments, the kits are useful in disinfecting a surface. In certain embodiments, the kits are useful for screening a library of compounds to identify a compound that is useful in the methods of the invention. In certain embodiments, the kit further includes instructions for using the compound or pharmaceutical composition included in the kit (e.g., for administering to a subject in need of treatment of a microbial infection a compound or pharmaceutical composition of the invention, for contacting a microorganism with a compound or pharmaceutical composition of the invention, or for contacting a biofilm with a compound or pharmaceutical composition of the invention). The kits may also include information as required by a regulatory agency such as the U.S. Food and Drug Administration (FDA). In certain embodiments, the information included in the kits is prescribing information. In certain embodiments, the kits and instructions provide for treating a microbial infection in a subject in need thereof. In certain embodiments, the kits and instructions provide for preventing a microbial infection in a subject in need thereof. In certain embodiments, the kits and instructions provide for inhibiting the growth of a microorganism. In certain embodiments, the kits and instructions provide for inhibiting the reproduction of a microorganism. In certain embodiments, the kits and instructions provide for killing a microorganism. In certain embodiments, the kits and instructions provide for inhibiting the formation and/or growth of a biofilm. In certain embodiments, the kits and instructions provide for reducing or removing a biofilm. In certain embodiments, the kits and instructions provide for disinfecting a surface. In certain embodiments, the kits and instructions provide for screening a library of compounds to identify a compound that is useful in the methods of the invention. The kit of the invention may include one or more additional agents described herein (e.g., additional pharmaceutical agents) as a separate composition.

Methods of Treatment and Uses

The present invention also provides methods for treating a microbial infection (e.g., bacterial infection) in a subject in need thereof. In certain embodiments, the microbial infection is treated by the inventive methods. In certain embodiments, the present invention further provides methods for preventing a microbial infection (e.g., bacterial infection) in a subject in need thereof. In certain embodiments, the microbial infection is prevented by the inventive methods.

In certain embodiments, the subject described herein is an animal. In certain embodiments, the subject is a non-human animal. In certain embodiments, the subject is a mammal. In certain embodiments, the subject is a human. In certain embodiments, the subject is a human with cystic fibrosis. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent, dog, or non-human primate. In certain embodiments, the subject is a non-human transgenic animal, such as a transgenic mouse or transgenic pig.

In certain embodiments, the methods of the invention include administering to a subject in need thereof an effective amount of a compound or pharmaceutical composition of the invention. In certain embodiments, the methods of the invention include administering to a subject in need thereof an effective amount of a compound of Formula (I), or a pharmaceutically acceptable salt thereof, or a pharmaceutical composition thereof. In certain embodiments, the methods of the invention include administering to a subject in need thereof an effective amount of a compound of Formula (I'), or a pharmaceutically acceptable salt thereof, or a pharmaceutical composition thereof. In certain embodiments, the methods of the invention include administering to a subject in need thereof a therapeutically effective amount of a compound of the invention, or a pharmaceutical composition thereof. In certain embodiments, the methods of the invention include administering to a subject in need thereof a prophylactically effective amount of a compound of the invention, or a pharmaceutical composition thereof.

In certain embodiments, the microbial infection that is treated and/or prevented by the inventive methods or using the inventive compounds or pharmaceutical compositions thereof is caused by a multidrug-resistant microorganism and/or a microorganism resistant to methicillin, penicillin, ciprofloxacin, rifampin, vancomycin, daptomycin, linezolid, an antibiotic described herein, or a combination thereof. In certain embodiments, the microbial infection is a microbial respiratory tract infection. In certain embodiments, the microbial infection is microbial pneumonia. In certain embodiments, the microbial infection is microbial sinusitis. In certain embodiments, the microbial infection is tuberculosis (TB). In certain embodiments, the microbial infection is microbial Crohn's disease, paratuberculosis, Buruli ulcer, leprosy, or aquarium granuloma. In certain embodiments, the microbial infection is a microbial gastrointestinal tract infection. In certain embodiments, the microbial infection is microbial diarrhea. In certain embodiments, the microbial infection is a microbial urogenital tract infection. In certain embodiments, the microbial infection is a microbial bloodstream infection. In certain embodiments, the microbial infection is microbial hemolytic uremic syndrome. In certain embodiments, the microbial infection is microbial endocarditis. In certain embodiments, the microbial infection is a microbial ear infection. In certain embodiments, the microbial infection is a microbial skin infection (e.g., microbial acne vulgaris). In certain embodiments, the microbial infection is a microbial oral infection. In certain embodiments, the microbial infection is a microbial dental infection. In certain embodiments, the microbial infection is gingivitis. In certain embodiments, the microbial infection is dental plaque caused by a microorganism. In certain embodiments, the microbial infection is microbial meningitis. In certain embodiments, the microbial infection is a microbial wound or surgical site infection. In certain embodiments, the microbial infection is a microbial burn wound infection. In certain embodiments, the microbial infection is a microbial infection associated with cystic fibrosis. In certain embodiments, the microbial infection is a microbial infection associated with an implanted device. In certain embodiments, the microbial infection is a microbial infection associated with a dental implant. In certain embodiments, the microbial infection is a microbial infection associated with a catheter. In certain embodiments, the microbial infection is a microbial infection associated with a heart valve. In certain embodiments, the microbial infection is a microbial infection associated with an intrauterine device. In certain embodiments, the microbial infection is a microbial infection associated with a joint prosthesis. In certain embodiments, the microbial infection is a bacterial infection. In certain embodiments, the bacterial infection is caused by a Gram-positive bacterium (e.g., a Gram-positive bacterium described herein). In certain embodiments, the bacterial infection is caused by a Gram-negative bacterium (e.g., a Gram-negative bacterium described herein). In certain embodiments, the bacterial infection is caused by a multidrug-resistant bacterium. In certain embodiments, the bacterial infection is caused by a strain of *Staphylococcus aureus*. In certain embodiments, the bacterial infection is a methicillin-resistant *Staphylococcus aureus* (MRSA)-related infection. In certain embodiments, the bacterial infection is caused by a strain of *Staphylococcus epidermidis*. In certain embodiments, the bacterial infection is caused by a strain of *Enterococcus faecium*. In certain embodiments, the bacterial infection is caused by *Acinetobacter baumannii*. In certain embodiments, the microbial infection is caused by a *mycobacterium* (e.g., a strain of *Mycobacterium tuberculosis*). In certain embodiments, the microbial infection is caused by an archaeon. In certain embodiments, the microbial infection is caused by a protist. In certain embodiments, the microbial infection is caused by a protozoon. In certain embodiments, the microbial infection is caused by an alga. In certain embodiments, the microbial infection is caused by a fungus. In certain embodiments, the microbial infection is caused by yeast. In certain embodiments, the microbial infection is caused by a mold. In certain embodiments, the microbial infection is caused by a parasite. In certain embodiments, the microbial infection is a microbial infection associated with a biofilm.

Another aspect of the present invention relates to methods of inhibiting the growth of a microorganism using a compound of the invention, or a pharmaceutical composition thereof. In certain embodiments, an inventive method selectively inhibits the growth of a first microorganism (e.g., a microorganism described herein), compared to the inhibition of the growth of a host cell or a second microorganism. In certain embodiments, the growth of a microorganism is inhibited by the inventive methods. In certain embodiments, the growth of a first microorganism is selectively inhibited by the inventive methods, compared to the inhibition of the growth of a host cell or a second microorganism.

Another aspect of the present invention relates to methods of inhibiting the reproduction of a microorganism using a compound of the invention, or a pharmaceutical composition thereof. In certain embodiments, an inventive method selectively inhibits the reproduction of a first microorganism (e.g., a microorganism described herein), compared to the inhibition of the reproduction of a host cell or a second microorganism. In certain embodiments, the reproduction of a microorganism is inhibited by the inventive methods. In certain embodiments, the reproduction of a first microorganism is selectively inhibited by the inventive methods, compared to the inhibition of the reproduction of a host cell or a second microorganism.

Another aspect of the present invention relates to methods of inhibiting the viability of a microorganism using a compound of the invention, or a pharmaceutical composition thereof. In certain embodiments, an inventive method selectively inhibits the viability of a first microorganism (e.g., a microorganism described herein), compared to the inhibition of the viability of a host cell or a second microorganism. In certain embodiments, the viability of a microorganism is inhibited by the inventive methods. In certain embodiments, the viability of a first microorganism is selectively inhibited by the inventive methods, compared to the inhibition of the viability of a host cell or a second microorganism.

Another aspect of the present invention relates to methods of killing a microorganism using a compound of the invention, or a pharmaceutical composition thereof. In certain embodiments, an inventive method selectively kills a first microorganism (e.g., a microorganism described herein), compared to the killing of a host cell or a second microorganism. In certain embodiments, a microorganism is killed by the inventive methods. In certain embodiments, a first microorganism is selectively killed by the inventive methods, compared to the killing of a host cell or a second microorganism.

In certain embodiments, the methods of the invention include contacting a microorganism with an effective amount of a compound or pharmaceutical composition of the invention. In certain embodiments, the methods of the invention include contacting a microorganism with an effective amount of a compound of Formula (I), or a pharmaceutically acceptable salt thereof, or a pharmaceutical composition thereof. In certain embodiments, the methods of the invention include contacting a microorganism with an effective amount of a compound of Formula (I'), or a pharmaceutically acceptable salt thereof, or a pharmaceutical composition thereof. In certain embodiments, the methods of the invention include contacting a microorganism with a therapeutically effective amount of a compound of the invention, or a pharmaceutical composition thereof. In certain embodiments, the methods of the invention include contacting a microorganism with a prophylactically effective amount of a compound of the invention, or a pharmaceutical composition thereof.

In a growth process of a microorganism (e.g., a bacterium), the microorganism may secrete viscous substances to form a biofilm. A biofilm is typically formed on a living or non-living, solid or liquid surface. In certain embodiments, a biofilm is formed on the surface of a biological sample (e.g., a tooth, oral soft tissue, middle ear, gastrointestinal tract, urogenital tract, respiratory tract, or eye). In certain embodiments, a biofilm is formed on the surface of an implanted device (e.g., a dental implant, catheter, heart valve, intrauterine device, or joint prosthesis). In certain embodiments, the biofilm is in vitro. In certain embodiments, the biofilm is in vivo. In certain embodiments, the biofilm described herein comprises a microorganism. In certain embodiments, the biofilm comprises a microorganism (e.g., bacterium). In certain embodiments, the biofilm comprises a strain of *Staphylococcus aureus* (e.g., a methicillin-resistant strain of *Staphylococcus aureus*). In certain embodiments, the biofilm comprises a strain of *Staphylococcus epidermidis* (e.g., a methicillin-resistant strain of *Staphylococcus epidermidis*). In certain embodiments, the biofilm comprises a strain of *Enterococcus faecium* (e.g., a vancomycin-resistant strain of *Enterococcus faecium*). Free-floating microorganisms may accumulate on a surface, and the resulting biofilm may grow. In a biofilm, the concentration of microorganisms may be high and/or the resistance of the microorganisms in the biofilm to antimicrobial agents may be high. Antimicrobials may be inactivated or fail to penetrate into the biofilm. Therefore, microbial infections associated with a biofilm (e.g., microbial infections caused by a biofilm) are typically more difficult to treat than microbial infections not associated with a biofilm.

Another aspect of the present invention relates to methods of inhibiting the formation of a biofilm using a compound of the invention, or a pharmaceutical composition thereof. In certain embodiments, the formation of a biofilm is inhibited by the inventive methods.

Another aspect of the present invention relates to methods of inhibiting the growth of a biofilm using a compound of the invention, or a pharmaceutical composition thereof. In certain embodiments, the growth of a biofilm is inhibited by the inventive methods.

Another aspect of the present invention relates to methods of reducing a biofilm using a compound of the invention, or a pharmaceutical composition thereof. In certain embodiments, a biofilm is reduced by the inventive methods, e.g., reduced by at least 10%, at least 20%, at least 30%, at least 50%, at least 70%, at least 90%, at least 99%, at least 99.9%, or at least 99.99%, in terms of the volume of the biofilm. In certain embodiments, a biofilm is reduced by the inventive methods by not more than 10%, not more than 20%, not more than 30%, not more than 50%, not more than 70%, not more than 90%, not more than 99%, not more than 99.9%, or not more than 99.99%, in terms of the volume of the biofilm. In certain embodiments, a biofilm is reduced by the inventive methods by at least 10%, at least 20%, at least 30%, at least 50%, at least 70%, at least 90%, at least 99%, at least 99.9%, or at least 99.99%, in terms of the number of microorganisms (e.g., bacteria) in the biofilm. In certain embodiments, a biofilm is reduced by the inventive methods by not more than 10%, not more than 20%, not more than 30%, not more than 50%, not more than 70%, not more than 90%, not more than 99%, not more than 99.9%, or not more than 99.99%, in terms of the number of microorganisms (e.g., bacteria) in the biofilm.

Another aspect of the present invention relates to methods of removing a biofilm (e.g., eradicating a biofilm (e.g., reducing the volume of the biofilm by at least 99% and/or killing essentially all (e.g., at least 99%) of the microorganisms (e.g., bacteria) in the biofilm)) using a compound of the invention, or a pharmaceutical composition thereof. In certain embodiments, a biofilm is removed by the inventive methods. In certain embodiments, a biofilm reduced or removed by a method of the invention does not regrow one day, two days, four days, one week, two weeks, three weeks, or one month subsequent to the biofilm being subject to the method.

In certain embodiments, the methods of the invention include contacting a biofilm with an effective amount of a compound or pharmaceutical composition of the invention. In certain embodiments, the methods of the invention include contacting a biofilm with an effective amount of a compound of Formula (I), or a pharmaceutically acceptable salt thereof, or a pharmaceutical composition thereof. In certain embodiments, the methods of the invention include contacting a biofilm with an effective amount of a compound of Formula (I'), or a pharmaceutically acceptable salt thereof, or a pharmaceutical composition thereof. In certain embodiments, the methods of the invention include contacting a biofilm with a therapeutically effective amount of a compound of the invention, or a pharmaceutical composition thereof. In certain embodiments, the methods of the invention include contacting a biofilm with a prophylactically effective amount of a compound of the invention, or a pharmaceutical composition thereof.

Another aspect of the present invention relates to methods of disinfecting a surface, the methods including contacting the surface with an effective amount of a compound or composition (e.g., pharmaceutical composition) of the invention. In certain embodiments, the number of viable microorganisms on the surface is reduced after the surface is contacted with the compound or composition. In certain embodiments, the surface is a biological surface, such as skin (e.g., skin of: the hands, feet, arms, legs, face, neck, torso, or cavity (e.g., oral cavity)) of a subject. In certain embodiments, the surface is a non-biological surface (e.g., a surface in a household, industrial, or medical setting, such as a surface of: a kitchen, bathroom, table top, floor, wall, window, utensil, cutlery, crockery, or medical device). A non-biological surface may be a surface of a solid material, such as plastic, wood, bamboo, metal, ceramic, glass, concrete, stone, paper, fabric, or a combination thereof. A non-biological surface may be painted or non-painted, or coated or non-coated. In certain embodiments, the amount of the compound or composition is effective for killing at least 80%, at least 90%, at least 95%, at least 99%, at least 99.9%, or at least 99.99% of the microorganisms on the surface.

In certain embodiments, the microorganism described herein is a bacterium. In certain embodiments, the microorganism is multidrug-resistant. In certain embodiments, the microorganism is resistant to methicillin, penicillin, ciprofloxacin, rifampin, vancomycin, daptomycin, linezolid, or a combination thereof. In certain embodiments, the microorganism is associated with a biofilm (e.g., present in and/or on a biofilm, able to form a biofilm, and/or able to increase the size of a biofilm). In certain embodiments, the bacterium is a Gram-positive bacterium. In certain embodiments, the bacterium is a multidrug-resistant bacterium. In certain embodiments, the bacterium is a *Staphylococcus* species. In certain embodiments, the bacterium is a *Staphylococcus aureus* (*S. aureus*) strain (e.g., ATCC 25923). In certain embodiments, the bacterium is methicillin-resistant *Staphylococcus aureus* (MRSA). In certain embodiments, the bacterium is the methicillin-resistant *Staphylococcus aureus* clinical isolate (MRSA-2, a clinical isolate from a patient treated at Shands Hospital; obtained from the Emerging Pathogens Institute at the University of Florida), such as the methicillin-resistant *Staphylococcus aureus* clinical isolate reported in Abouelhassan et al., *Bioorg. Med. Chem. Lett.*, 2014, 24, 5076. In certain embodiments, the bacterium is a *Staphylococcus epidermidis* (*S. epidermidis*) strain (e.g., ATCC 12228 or ATCC 35984). In certain embodiments, the bacterium is a *Staphylococcus auricularis, Staphylococcus carnosus, Staphylococcus condimenti, Staphylococcus massiliensis, Staphylococcus piscifermentans, Staphylococcus simulans, Staphylococcus capitis, Staphylococcus caprae, Staphylococcus saccharolyticus, Staphylococcus devriesei, Staphylococcus haemolyticus, Staphylococcus hominis, Staphylococcus chromogenes, Staphylococcus felis, Staphylococcus delphini, Staphylococcus hyicus, Staphylococcus intermedius, Staphylococcus lutrae, Staphylococcus microti, Staphylococcus muscae, Staphylococcus pseudintermedius, Staphylococcus rostri, Staphylococcus schleiferi, Staphylococcus lugdunensis, Staphylococcus arlettae, Staphylococcus cohnii, Staphylococcus equorum, Staphylococcus gallinarum, Staphylococcus kloosii, Staphylococcus leei, Staphylococcus nepalensis, Staphylococcus saprophyticus, Staphylococcus succinus, Staphylococcus xylosus, Staphylococcus fleurettii, Staphylococcus lentus, Staphylococcus sciuri, Staphylococcus stepanovicii, Staphylococcus vitulinus, Staphylococcus simulans, Staphylococcus pasteuri*, or *Staphylococcus warneri* strain. In certain embodiments, the bacterium is a *Streptococcus* species. In certain embodiments, the bacterium is a *Streptococcus agalactiae, Streptococcus anginosus, Streptococcus bovis, Streptococcus canis, Streptococcus constellatus, Streptococcus dysgalactiae, Streptococcus equinus, Streptococcus iniae, Streptococcus intermedius, Streptococcus mitis, Streptococcus mutans, Streptococcus oralis, Streptococcus parasanguinis, Streptococcus peroris, Streptococcus pneumoniae, Streptococcus pseudopneumoniae, Streptococcus pyogenes, Streptococcus ratti, Streptococcus salivarius, Streptococcus tigurinus, Streptococcus thermophilus, Streptococcus sanguinis, Streptococcus sobrinus, Streptococcus suis, Streptococcus uberis, Streptococcus vestibularis, Streptococcus viridans,* or *Streptococcus zooepidemicus* strain. In certain embodiments, the bacterium is an *Enterococcus* species. In certain embodiments, the bacterium is an *Enterococcus avium, Enterococcus durans, Enterococcus faecalis, Enterococcus faecium, Enterococcus gallinarum, Enterococcus hirae,* or *Enterococcus solitarius* strain. In certain embodiments, the bacterium is an *Enterococcus faecium* strain (e.g., a vancomycin-resistant strain of *Enterococcus faecium* (VRE); ATCC 700221). In certain embodiments, the bacterium is a *Listeria* species. In certain embodiments, the bacterium is a *Listeria fleischmannii, Listeria grayi, Listeria innocua, Listeria ivanovii, Listeria marthii, Listeria monocytogenes, Listeria rocourtiae, Listeria seeligeri, Listeria weihenstephanensis,* or *Listeria welshimeri* strain. In certain embodiments, the bacterium is a *Clostridium* species. In certain embodiments, the bacterium is a *Clostridium acetobutylicum, Clostridium argentinense, Clostridium aerotolerans, Clostridium baratii, Clostridium beijerinckii, Clostridium bifermentans, Clostridium botulinum, Clostridium butyricum, Clostridium cadaveris, Clostridium cellulolyticum, Clostridium chauvoei, Clostridium clostridioforme, Clostridium colicanis, Clostridium difficile, Clostridium estertheticum, Clostridium fallax, Clostridium feseri, Clostridium formicaceticum, Clostridium histolyticum, Clostridium innocuum, Clostridium kluyveri, Clostridium ljungdahlii, Clostridium lavalense, Clostridium leptum, Clostridium novyi, Clostridium oedematiens, Clostridium paraputrificum, Clostridium perfringens* (Alias: *Clostridium welchii*), *Clostridium phytofermentans, Clostridium piliforme, Clostridium ragsdalei, Clostridium ramosum, Clostridium scatologenes, Clostridium septicum, Clostridium sordellii, Clostridium sporogenes, Clostridium sticklandii, Clostridium tertium, Clostridium tetani, Clostridium thermocellum, Clostridium thermosaccharolyticum,* or *Clostridium tyrobutyricum* strain. In certain embodiments, the bacterium is a Gram-negative bacterium. In certain embodiments, the Gram-negative bacterium is an *Escherichia* species. In certain embodiments, the Gram-negative bacterium is an *Escherichia coli* (*E. coli*) strain (e.g., ATCC 33475, K-12, CFT073, ATCC 43895). In certain embodiments, the Gram-negative bacterium is an *Escherichia albertii* strain, *Escherichia blattae* strain, *Escherichia fergusonii* strain, *Escherichia hermannii* strain, or *Escherichia vulneris* strain. In certain embodiments, the Gram-negative bacterium is a *Pseudomonas* species. In certain embodiments, the Gram-negative bacterium is a *Pseudomonas aeruginosa* strain. In certain embodiments, the Gram-negative bacterium is a *Pseudomonas alcaligenes* strain, *Pseudomonas anguilliseptica* strain, *Pseudomonas argentinensis* strain, *Pseudomonas borbori* strain, *Pseudomonas citronellolis* strain, *Pseudomonas flavescens* strain, *Pseudomonas mendocina* strain, *Pseudomonas nitroreducens* strain, *Pseudomonas oleovorans* strain, *Pseudomonas pseudoalcaligenes* strain, *Pseudomonas resinovorans* strain, *Pseudomonas straminea* strain, *Pseudomonas chlororaphis* strain, *Pseudomonas fluorescens* strain, *Pseudomonas pertucinogena* strain, *Pseudomonas putida* strain, *Pseudomonas stutzeri* strain, or *Pseudomonas syringae* strain. In certain embodiments, the Gram-negative bacterium is a *Klebsiella* species. In certain embodiments, the Gram-negative bacterium is a *Klebsiella granulomatis* strain, *Klebsiella oxytoca* strain, *Klebsiella pneumoniae* strain, *Klebsiella terrigena* strain, or *Klebsiella planticola* strain. In certain embodiments, the Gram-negative bacterium is a *Salmonella* species. In certain embodiments, the Gram-negative bacterium is a *Salmonella bongori* strain or *Salmonella enterica* strain, e.g., *Salmonella typhi*. In certain embodiments, the Gram-negative bacterium is an *Acinetobacter* species. In certain embodiments, the Gram-negative bacterium is an *Acinetobacter baumannii* strain. In certain embodiments, the Gram-negative bacterium is an *Acinetobacter baylyi* strain, *Acinetobacter bouvetii* strain, *Acinetobacter calcoaceticus* strain, *Acinetobacter gerneri* strain, *Acinetobacter grimontii* strain, *Acinetobacter haemolyticus* strain, *Acinetobacter johnsonii* strain, *Acinetobacter junii* strain, *Acinetobacter lwoffii* strain, *Acinetobacter parvus* strain, *Acinetobacter pittii* strain, *Acinetobacter radioresistens* strain, *Acinetobacter schindleri* strain, *Acinetobacter tandoii* strain, *Acinetobacter tjernbergiae* strain, *Acinetobacter towneri* strain, *Acinetobacter ursingii* strain, or *Acinetobacter gyllenbergii* strain. In certain embodiments, the microorganism is a *mycobacterium*. In certain embodiments, the microorganism is a strain of *Mycobacterium tuberculosis*. In certain embodiments, the microorganism is a strain of: *Mycobacterium bovis, Mycobacterium bovis* BCG, *Mycobacterium africanum, Mycobacterium canetti, Mycobacterium caprae, Mycobacterium microti, Mycobacterium Pin-*

*nipedii, Mycobacterium avium, Mycobacterium avium paratuberculosis, Mycobacterium avium silvaticum, Mycobacterium avium hominissuis, Mycobacterium colombiense, Mycobacterium indicus pranii, Mycobacterium gastri, Mycobacterium kansasii, Mycobacterium hiberniae, Mycobacterium nonchromogenicum, Mycobacterium terrae, Mycobacterium triviale, Mycobacterium ulcerans, Mycobacterium pseudoshottsii, Mycobacterium shottsii, Mycobacterium triplex, Mycobacterium genavense, Mycobacterium florentinum, Mycobacterium lentiflavum, Mycobacterium palustre, Mycobacterium kubicae, Mycobacterium parascrofulaceum, Mycobacterium heidelbergense, Mycobacterium interjectum, Mycobacterium simiae, Mycobacterium bohemicum, Mycobacterium botniense, Mycobacterium branderi, Mycobacterium celatum, Mycobacterium chimaera, Mycobacterium conspicuum, Mycobacterium cookii, Mycobacterium doricum, Mycobacterium farcinogenes, Mycobacterium haemophilum, Mycobacterium heckeshornense, Mycobacterium intracellulare, Mycobacterium lacus, Mycobacterium leprae, Mycobacterium lepraemurium, Mycobacterium lepromatosis, Mycobacterium malmoense, Mycobacterium marinum, Mycobacterium monacense, Mycobacterium montefiorense, Mycobacterium murale, Mycobacterium nebraskense, Mycobacterium saskatchewanense, Mycobacterium scrofulaceum, Mycobacterium shimoidei, Mycobacterium szulgai, Mycobacterium tusciae, Mycobacterium xenopi, Mycobacterium yongonense, Mycobacterium intermedium, Mycobacterium abscessus, Mycobacterium chelonae, Mycobacterium bolletii, Mycobacterium fortuitum, Mycobacterium fortuitum* subsp. *acetamidolyticum, Mycobacterium boenickei, Mycobacterium peregrinum, Mycobacterium porcinum, Mycobacterium senegalense, Mycobacterium septicum, Mycobacterium neworleansense, Mycobacterium houstonense, Mycobacterium mucogenicum, Mycobacterium mageritense, Mycobacterium brisbanense, Mycobacterium cosmeticum, Mycobacterium parafortuitum, Mycobacterium austroafricanum, Mycobacterium diernhoferi, Mycobacterium hodleri, Mycobacterium neoaurum, Mycobacterium frederiksbergense, Mycobacterium aurum, Mycobacterium vaccae, Mycobacterium chitae, Mycobacterium fallax, Mycobacterium confluentis, Mycobacterium flavescens, Mycobacterium madagascariense, Mycobacterium phlei, Mycobacterium smegmatis Mycobacterium goodii, Mycobacterium wolinskyi, Mycobacterium thermoresistibile, Mycobacterium gadium, Mycobacterium komossense, Mycobacterium obuense, Mycobacterium sphagni, Mycobacterium agri, Mycobacterium aichiense, Mycobacterium alvei, Mycobacterium arupense, Mycobacterium brumae, Mycobacterium canariasense, Mycobacterium chubuense, Mycobacterium conceptionense, Mycobacterium duvalii, Mycobacterium elephantis, Mycobacterium gilvum, Mycobacterium hassiacum, Mycobacterium holsaticum, Mycobacterium immunogenum, Mycobacterium massiliense, Mycobacterium moriokaense, Mycobacterium psychrotolerans, Mycobacterium pyrenivorans, Mycobacterium vanbaalenii, Mycobacterium pulveris, Mycobacterium arosiense, Mycobacterium aubagnense, Mycobacterium caprae, Mycobacterium chlorophenolicum, Mycobacterium fluoroanthenivorans, Mycobacterium kumamotonense, Mycobacterium novocastrense, Mycobacterium parmense, Mycobacterium phocaicum, Mycobacterium poriferae, Mycobacterium rhodesiae, Mycobacterium seoulense,* or *Mycobacterium tokaiense.*

In certain embodiments, the microorganism described herein is an archaeon. In certain embodiments, the microorganism is a protist. In certain embodiments, the microorganism is a protozoon. In certain embodiments, the microorganism is an alga. In certain embodiments, the microorganism is a fungus. In certain embodiments, the microorganism is yeast. In certain embodiments, the microorganism is a mold. In certain embodiments, the microorganism is a parasite.

In certain embodiments, the microorganism described herein is in vitro. In certain embodiments, the microorganism is in vivo.

In certain embodiments, a method of the invention is an in vitro method. In certain embodiments, a method of the invention is an in vivo method.

In another aspect, the present invention provides uses of the compounds, compositions, and pharmaceutical compositions of the invention for manufacturing a medicament for treating a microbial infection (e.g., bacterial infection).

In another aspect, the present invention provides uses of the compounds, compositions, and pharmaceutical compositions of the invention for manufacturing a medicament for preventing a microbial infection (e.g., bacterial infection).

In another aspect, the present invention provides the compounds, compositions, and pharmaceutical compositions of the invention for use in treating a microbial infection (e.g., bacterial infection).

In another aspect, the present invention provides the compounds, compositions, and pharmaceutical compositions of the invention for use in preventing a microbial infection (e.g., bacterial infection).

EXAMPLES

These and other aspects of the present invention will be further appreciated upon consideration of the following Examples, which are intended to illustrate certain particular embodiments of the invention but are not intended to limit its scope, as defined by the claims.

Preparation of Exemplary Compounds

Materials and Methods

All reactions were carried out under an atmosphere of argon using anhydrous solvents unless otherwise specified. All chemical reagents for synthesis were used without further purification. Analytical thin layer chromatography (TLC) was performed using 250 μm Silica Gel 60 F254 pre-coated plates (EMD Chemicals Inc.). Flash column chromatography was performed using 230-400 Mesh 60 Å Silica Gel from Sorbent Technologies.

NMR experiments were recorded using broadband probes on a Varian Mercury-Plus-400 spectrometer via VNMR-J software (400 MHz for 1H and 100 MHz for 13C). All spectra are presented using MestReNova (Mnova) software and 1H NMR are typically displayed from 10.7 to −0.7 ppm without the use of the signal suppression function. Spectra were obtained in the following solvents (reference peaks also included for 1H and 13C NMRs): CDCl3 (1H NMR: 7.26 ppm; 13C NMR: 77.23 ppm), d6-DMSO (1H NMR: 2.50 ppm; 13C NMR: 39.52 ppm). All NMR experiments were performed at room temperature. Chemical shift values (δ) are reported in parts per million (ppm) for all 1H NMR and 13C NMR spectra. 1H NMR multiplicities are reported as: br.=broad, s=singlet, d=doublet, t=triplet, p=pentet, m=multiplet. High-resolution mass spectra were obtained for all new compounds from the Chemistry Department at the University of Florida.

DMSO stocks of quinoline compounds tested were stored at room temperature in the absence of light for several months at a time without observing a loss in biological activity. The DMSO stock solutions were not subjected to DMSO stocks of test compounds to freeze-thaw cycles to ensure the compound integrity.

General Halogenation Procedure Using Commercially Available 8-hydroxyquinolines (2, 3, and HQ-8 to HQ-19)

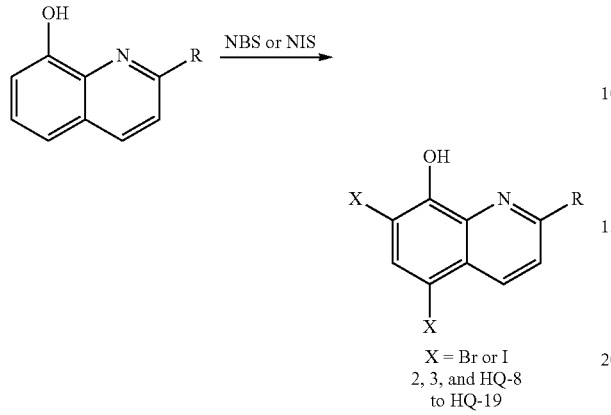

X = Br or I
2, 3, and HQ-8 to HQ-19

5,7-dibromo-8-hydroxyquinoline-2-carbonitrile (HQ-8)

To a stirring solution of 8-hydroxyquinoline-2-carbonitrile (50 mg, 0.29 mmol) in 15 mL toluene at room temperature, N-iodosuccinimide (NIS, 115 mg, 0.65 mmol) was added and the reaction mixture was stirred for 10 hours. The completion of the reaction was confirmed via TLC before being concentrated in vacuo. The crude material was then adsorbed onto silica using dichloromethane and concentrated in vacuo before being applied to a column. The crude products were then purified via flash column chromatography using methylene chloride to elute pure 5,7-dibromo-8-hydroxyquinoline-2-carbonitrile HQ-8 as a pale yellow solid (56 mg, 58%).

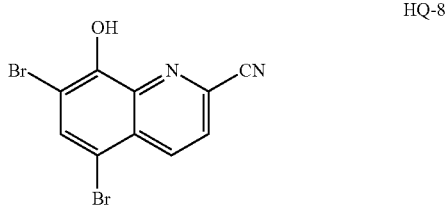

HQ-8

Yield: 58% yield; 56 mg of HQ-8 was isolated as a pale yellow solid.

$^1$H NMR (400 MHz, $d_6$-DMSO): 8.64 (d, J=8.7 Hz, 1H), 8.27 (s, 1H), 8.19 (d, J=8.7 Hz, 1H).

$^{13}$C NMR (100 MHz, $d_6$-DMSO): 151.4, 139.2, 137.7, 136.4, 132.1, 127.4, 126.0, 117.1, 108.7, 107.6.

HRMS (DART): calcd for $C_{10}H_5Br_2N_2O$ $[M+H]^+$: 326.8763, found: 326.8759.

MP: 172-174° C. 5,7-dibromo-8-hydroxyquinoline-2-carbaldehyde (2)

To a stirring solution of 8-hydroxyquinoline-2-carbaldehyde (100 mg, 0.58 mmol) in 15 mL toluene at room temperature, N-bromosuccinimide (226 mg, 1.27 mmol) was added and the reaction mixture was stirred for 8 hours. The completion of the reaction was confirmed via TLC before being concentrated in vacuo. The crude material was then adsorbed onto silica using dichloromethane and concentrated in vacuo before being applied to a column. The crude product was then purified via flash column chromatography using hexanes:methylene chloride (2:1 to 1:1) to elute pure quinoline derivative 2 as a yellow solid (140 mg, 73%).

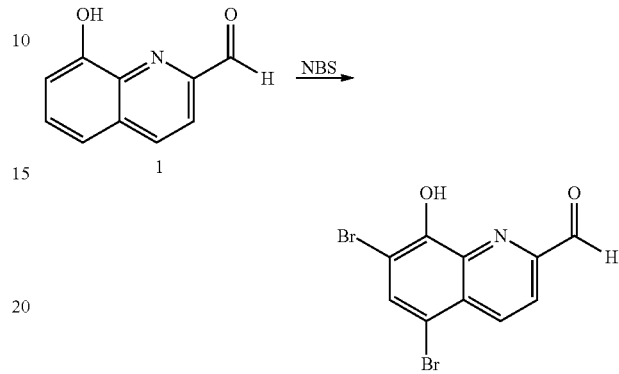

$^1$H NMR (400 MHz, $d_6$-DMSO): 11.34 (br. s, 1H), 10.20 (s, 1H), 8.64 (d, J=8.7 Hz, 1H), 8.26 (s, 1H), 8.15 (d, J=8.7 Hz, 1H).

$^{13}$C NMR (100 MHz, $d_6$-DMSO): 192.5, 151.8, 151.3, 138.7, 137.4, 136.0, 128.2, 119.2, 109.0, 106.6.

HRMS (DART): calcd for $C_{10}H_6Br_2NO_2$ $[M+H]^+$: 329.8760, found: 329.8764.

MP: 154-156° C.

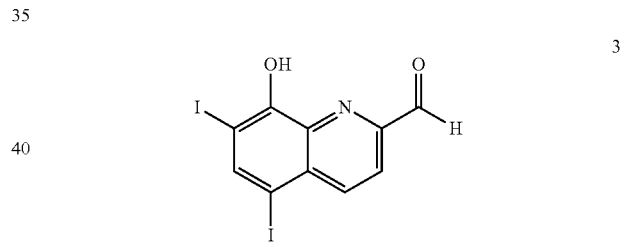

Yield: 67% yield; 70 mg of 3 was isolated as a light yellow solid.

$^1$H NMR (400 MHz, $d_6$-DMSO): 10.20 (s, 1H), 8.50 (s, 1H), 8.48 (d, J=9.2 Hz, 1H), 8.10 (d, J=8.7 Hz, 1H).

$^{13}$C NMR (100 MHz, $d_6$-DMSO): 192.4, 155.5, 151.1, 147.3, 141.9, 137.5, 131.4, 119.6, 85.4, 82.7.

HRMS (ESI): calcd for $C_{10}H_6I_2NO_2$ $[M+H]^+$: 447.8302, found: 447.8284.

MP: 146-148° C.

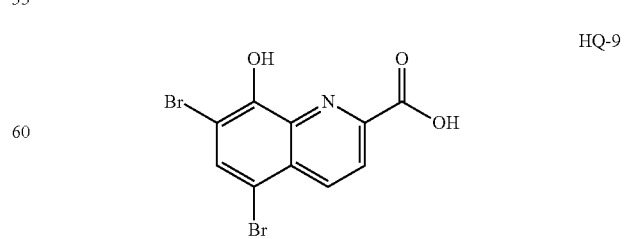

Yield: 52% yield; 48 mg of HQ-9 was isolated as a yellow solid.

$^1$H NMR (400 MHz, d$_6$-DMSO): 13.09 (br. s, 1H), 11.16 (s, 1H), 8.65 (d, J=8.7 Hz, 1H), 8.31 (d, J=8.7 Hz, 1H), 8.24 (s, 1H).

$^{13}$C NMR (100 MHz, d$_6$-DMSO): 164.4, 151.4, 145.9, 137.9, 137.1, 135.7, 127.7, 121.9, 108.9, 105.7.

HRMS (ESI): calcd for C$_{10}$H$_5$Br$_2$NO$_3$Na [M+Na]$^+$: 367.8528, found: 367.8516. MP: >225° C.

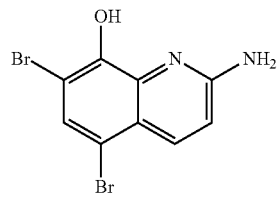

Yield: 60% yield; 42 mg of HQ-10 was isolated as a brown solid.

$^1$H NMR (400 MHz, d$_6$-DMSO): 8.00 (d, J=9.0 Hz, 1H), 7.53 (s, 1H), 6.95 (d, J=9.1 Hz, 1H), 6.82 (br. s, 2H).

$^{13}$C NMR (100 MHz, d$_6$-DMSO): 157.8, 147.6, 136.2, 126.9, 120.2, 115.6, 114.5, 109.3, 104.5.

HRMS (ESI): calcd for C$_9$H$_7$Br$_2$N$_2$O [M+H]$^+$: 316.8920, found: 316.8893.

MP: 170-172° C.

5,7-dibromo-2-(hydroxymethyl)quinolin-8-ol (HQ-11)

To a stirring solution of 2 (50 mg, 0.15 mmol) in 20 mL methanol, sodium borohydride (12 mg, 0.30 mmol) was added. The reaction mixture was stirred at room temperature for 1 hour and then concentrated in vacuo before stirring in 10% sodium hydroxide solution for 30 minutes. The solution was neutralized using 1N hydrochloric acid solution and extracted with dichloromethane 3×20 mL. The combined organic layers were dried with sodium sulfate, filtered, and adsorbed on silica before being applied to a column. The respective crude products were then purified via flash column chromatography using ethyl acetate to elute pure HQ-11 as a yellow solid (35 mg, 70%).

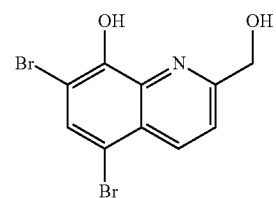

Yield: 70% yield; 35 mg of HQ-11 was isolated as a yellow solid.

$^1$H NMR (400 MHz, d$_6$-DMSO): 8.41 (d, J=8.7 Hz, 1H), 8.00 (s, 1H), 7.77 (d, J=8.8 Hz, 1H), 4.85 (s, 2H).

$^{13}$C NMR (100 MHz, d$_6$-DMSO): 161.7, 150.5, 137.7, 135.7, 132.5, 125.5, 121.1, 108.9, 104.9, 64.0.

HRMS (ESI): calcd for C$_{10}$H$_7$Br$_2$NO$_2$Na [M+Na]$^+$: 353.8736, found: 353.8730.

MP: 131-133° C.

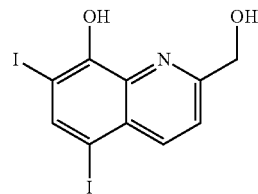

Yield: 80% yield; 40 mg of HQ-12 was isolated as a brown solid.

$^1$H NMR (400 MHz, d$_6$-DMSO): 8.18 (s, 1H), 8.17 (d, J=7.2 Hz, 1H), 7.63 (d, J=8.7 Hz, 1H), 4.80 (s, 2H).

$^{13}$C NMR (100 MHz, d$_6$-DMSO): 161.2, 154.7, 143.8, 140.3, 136.9, 128.7, 121.5, 84.6, 80.8, 63.9.

HRMS (ESI): calcd for C$_{10}$H$_7$I$_2$NO$_2$Na [M+Na]$^+$: 449.8458, found: 449.8441.

MP: 145-147° C.

5,7-dibromo-2-(1-hydroxyethyl)-8-hydroxyquinoline (HQ-13)

To a stirring solution of 2 (50 mg, 0.15 mmol) in 5 mL anhydrous tetrahydrofuran at −78° C. temperature, methyl lithium (0.28 mL, 1.6M solution in toluene, 0.45 mmol) was added under argon via syringe and stirred at −78° C. temperature for 1 hour. Completion of the reaction was checked via TLC and reaction was quenched using saturated ammonium chloride solution. The solution was neutralized using 1N hydrochloric acid solution and extracted with 3×20 mL ethyl acetate. The combined organic layers were washed with brine, dried with sodium sulfate, filtered, and adsorbed on silica before being applied to a column. The crude product was then purified via flash column chromatography using ethyl acetate to elute pure 5,7-dibromo-2-(1-hydroxyethyl)-8-hydroxyquinoline HQ-13 as a pale yellow solid (24 mg, 46%).

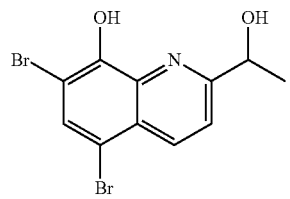

$^1$H NMR (400 MHz, d$_6$-DMSO): 8.42 (d, J=8.8 Hz, 1H), 8.02 (s, 1H), 7.83 (d, J=8.8 Hz, 1H), 5.73 (d, J=5.2 Hz, 1H), 5.00 (p, J=6.4 Hz, 1H), 1.47 (d, J=6.6 Hz, 3H).

$^{13}$C NMR (100 MHz, d$_6$-DMSO): 165.3, 150.5, 137.5, 136.0, 132.6, 125.4, 120.6, 108.9, 104.9, 69.1, 24.4.

HRMS (ESI): calcd for C$_{11}$H$_9$Br$_2$NO$_2$Na [M+Na]$^+$: 367.8892, found: 367.8878.

MP: 114-116° C.

5,7-dibromo-8-hydroxyquinoline-2-carboximidamide (HQ-14)

Compound HQ-8 (50 mg, 0.15 mmol) was dissolved in 2 mL concentrated ammonia and ammonium chloride (16 mg, 0.03 mmol) was added. The mixture was heated in a sealed glass tube at 150° C. for 8 hours. The solution was cooled to room temperature and neutralized using 1N hydrochloric acid solution and extracted with 3×20 mL ethyl acetate. The combined organic layers were washed with brine, dried with sodium sulfate, filtered, and recrystallized from hot ethanol to obtain pure 5,7-dibromo-8-hydroxyquinoline-2-carboximidamide HQ-14 as a brownish yellow solid (28 mg, 53%).

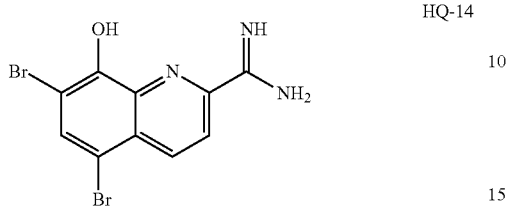

HQ-14

¹H NMR (400 MHz, d₆-DMSO): 11.55 (s, 1H), 8.66 (d, J=8.7 Hz, 1H), 8.29 (s, 1H), 8.21 (d, J=8.7 Hz, 1H), 7.33 (s, 1H), 7.20 (s, 1H), 7.07 (s, 1H).

¹³C NMR (100 MHz, d₆-DMSO): 151.3, 139.2, 137.8, 136.4, 132.2, 127.4, 126.0, 117.1, 108.9, 107.6.

HRMS (ESI): calcd for $C_{10}H_8Br_2N_3O$ [M+H]⁺: 343.9029, found: 343.9040.

MP: 172-174° C.

Compounds HQ-15 to HQ-19 were prepared using methods similar to the methods described herein:

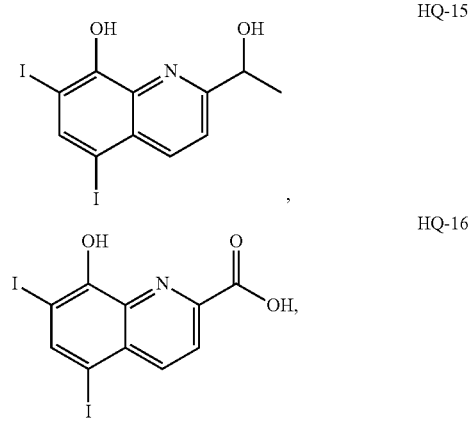

HQ-15

HQ-16

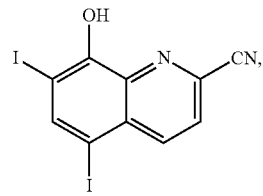

HQ-17

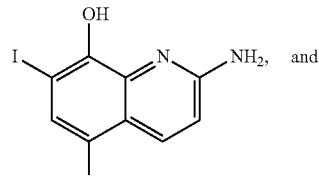

HQ-18

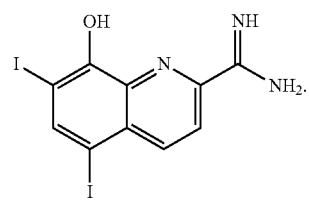 [SMILES: N=C(N)c1ccc2c(I)cc(I)c(O)c2n1]

HQ-19

General Reductive Amination Procedure (HQ-2 to HQ-7, and RA-HQ-2 to RA-HQ-23)

To a stirring solution of 2 (100 mg, 0.3 mmol) in 1,2-dichloroethane (10 mL) at room temperature, aliphatic amine or aniline (0.45 mmol) was added and the resulting reaction mixture was continued to stir (for 15 minutes with aliphatic amines and 1 hour with anilines) until the 2 was consumed via TLC. Then sodium triacetoxyborohydride (77 mg, 0.45 mmol) was added to the reaction mixture which was allowed to stir at room temperature for an additional 12 hours. After that time, the reaction was concentrated in vacuo and then stirred in 10 mL saturated sodium bicarbonate solution for 30 minutes. The crude product was extracted with dichloromethane (2×30 mL) and the combined organic layer was washed with brine, dried with anhydrous sodium sulfate, filtered and adsorbed on silica before being applied to a column. The crude products were then purified via flash column chromatography using hexanes:ethyl acetate (5:1 to 3:1) to elute pure quinolines HQ-2 to HQ-7, and RA-HQ-2 to RA-HQ-23.

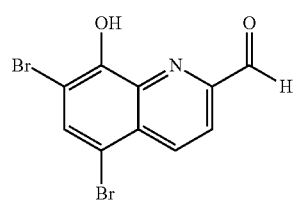

2 or

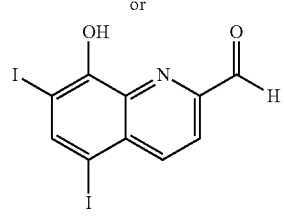

2

R—NH₂; then NaBH(OAc)₃ →

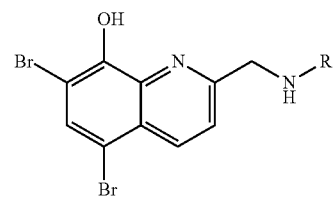

HQ-2 to HQ-7 and
RA-HQ-2 to RA-HQ-21

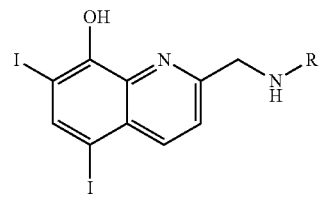

RA-HQ-22 to RA-HQ-23

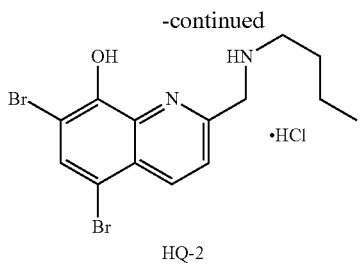

HQ-2

Yield: 68% yield; 120 mg of HQ-2, also referred to as RA-HQ-1, was isolated as a yellow solid.

$^1$H NMR (400 MHz, d$_6$-DMSO): 9.59 (br. s, 2H), 8.40 (d, J=8.7 Hz, 1H), 7.96 (s, 1H), 7.72 (d, J=8.7 Hz, 1H), 4.55 (s, 2H), 3.05-2.90 (m, 2H), 1.72 (p, J=7.7 Hz, 2H), 1.30 (sextet, J=7.6 Hz, 2H), 0.82 (t, J=7.5 Hz, 3H).

$^{13}$C NMR (100 MHz, d$_6$-DMSO): 153.0, 151.0, 137.8, 137.0, 133.8, 126.2, 122.8, 109.3, 105.6, 50.5, 47.4, 27.6, 19.7, 13.8.

HRMS (ESI): calcd for C$_{14}$H$_{16}$Br$_2$N$_2$ONa [M+Na]$^+$: 408.9522, found: 408.9518.

MP: 184-186° C.

Note: The free base of HQ-2 was used in biological experiments; however, the HCl salt of HQ-2 was made for characterization purposes.

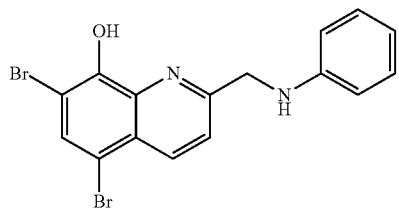

HQ-3

Yield: 44% yield; 35 mg of HQ-3, also referred to as RA-HQ-5, was isolated as a white solid.

$^1$H NMR (400 MHz, CDCl$_3$): 8.38 (d, J=8.7 Hz, 1H), 7.87 (s, 1H), 7.64 (d, J=8.7 Hz, 1H), 7.18 (dd, J=8.5, 7.3 Hz, 2H), 6.75 (t, J=7.3 Hz, 1H), 6.67 (dd, J=8.6, 1.2 Hz, 2H), 4.70 (s, 2H).

$^{13}$C NMR (100 MHz, CDCl$_3$): 160.0, 149.4, 147.6, 138.1, 137.1, 133.5, 129.6, 126.0, 121.7, 118.5, 113.3, 110.4, 104.4, 49.8.

HRMS (ESI): calcd for C$_{16}$H$_{12}$Br$_2$N$_2$ONa [M+Na]$^+$: 428.9209, found: 428.9202.

MP: 181-183° C.

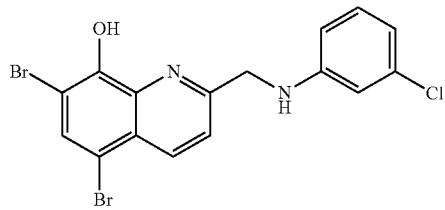

HQ-4

Yield: 65% yield; 60 mg of HQ-4, also referred to as RA-HQ-7, was isolated as a light yellow solid.

$^1$H NMR (400 MHz, CDCl$_3$): δ 8.41 (d, J=8.7 Hz, 1H), 7.88 (s, 1H), 7.61 (d, J=8.7 Hz, 1H), 7.08 (t, J=8.0 Hz, 1H), 6.71 (dd, J=7.8, 1.8 Hz, 1H), 6.66 (t, J=2.2 Hz, 1H), 6.53 (dd, J=8.2, 2.3 Hz, 1H), 4.73 (s, 1H), 4.68 (s, 2H).

$^{13}$C NMR (100 MHz, CDCl$_3$): 159.1, 149.4, 148.7, 138.1, 137.3, 135.4, 133.7, 130.6, 126.0, 121.6, 118.4, 113.0, 111.5, 110.4, 104.6, 49.4.

HRMS (ESI): calcd for C$_{16}$H$_{11}$Br$_2$ClN$_2$ONa [M+Na]$^+$: 462.8798, found: 462.8782.

MP: 175-177° C.

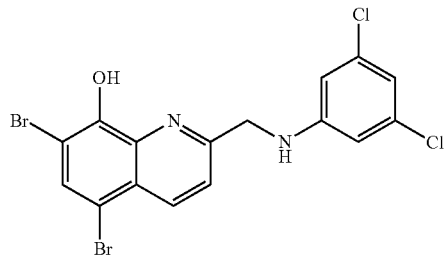

HQ-5

Yield: 60% yield; 45 mg of HQ-5, also referred to as RA-HQ-9, was isolated as a white solid.

$^1$H NMR (400 MHz, CDCl$_3$): 8.41 (d, J=8.7 Hz, 1H), 7.88 (s, 1H), 7.55 (d, J=8.7 Hz, 1H), 6.71 (m, 1H), 6.56 (d, J=1.8 Hz, 2H), 4.95 (br. s, 1H), 4.64 (s, 2H).

$^{13}$C NMR (100 MHz, CDCl$_3$): 158.1, 149.4, 149.2, 138.0, 137.4, 135.9, 133.8, 126.1, 121.5, 118.1, 111.4, 110.4, 104.9, 49.1.

HRMS (ESI): calcd for C$_{16}$H$_{10}$Br$_2$Cl$_2$N$_2$ONa [M+Na]$^+$: 496.8429, found: 496.8399.

MP: 164-166° C.

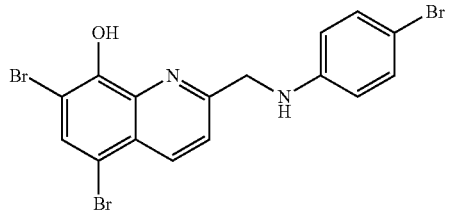

HQ-6

Yield: 60% yield; 42 mg of HQ-6, also referred to as RA-HQ-8, was isolated as a light yellow solid.

$^1$H NMR (400 MHz, CDCl$_3$): 8.38 (d, J=8.6 Hz, 1H), 7.87 (s, 1H), 7.58 (d, J=8.6 Hz, 1H), 7.25 (d, J=8.1 Hz, 2H), 6.54 (d, J=8.2 Hz, 2H), 4.65 (s, 2H).

$^{13}$C NMR (100 MHz, CDCl$_3$): 159.3, 149.3, 146.5, 138.1, 137.2, 133.6, 132.3, 126.0, 121.6, 114.8, 110.4, 110.1, 104.5, 49.6.

HRMS (DART): calcd for C$_{16}$H$_{12}$Br$_3$N$_2$O [M+H]$^+$: 484.8494, found: 484.8492.

MP: 161-163° C.

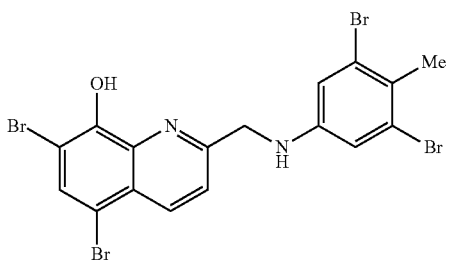

HQ-7

Yield: 45% yield; 55 mg of HQ-7, also referred to as RA-HQ-11, was isolated as a light yellow solid.

$^1$H NMR (400 MHz, CDCl$_3$): 8.42 (d, J=8.7 Hz, 1H), 7.89 (s, 1H), 7.57 (d, J=8.7 Hz, 1H), 6.87 (s, 2H), 4.63 (s, 2H), 2.43 (s, 3H).

$^1$H NMR (400 MHz, d$_6$-DMSO): 10.76 (s, 1H), 8.41 (d, J=8.7 Hz, 1H), 8.04 (s, 1H), 7.70 (d, J=8.7 Hz, 1H), 7.06 (s, 2H), 7.01 (t, J=4.9 Hz, 1H), 4.63 (d, J=4.8 Hz, 2H), 2.35 (s, 3H).

$^{13}$C NMR (100 MHz, CDCl$_3$): 158.6, 149.5, 146.9, 138.2, 137.4, 133.9, 126.5, 126.1, 125.9, 121.6, 116.6, 110.5, 104.8, 49.4, 22.6.

$^{13}$C NMR (100 MHz, d$_6$-DMSO): 157.8, 150.4, 148.1, 137.6, 135.9, 132.8, 125.5, 124.9, 122.3, 122.3, 115.5, 109.0, 105.1, 47.7, 22.0.

HRMS (ESI): calcd for C$_{17}$H$_{12}$Br$_4$N$_2$ONa [M+Na]$^+$: 598.7575, found: 598.7564.

MP: 144-146° C.

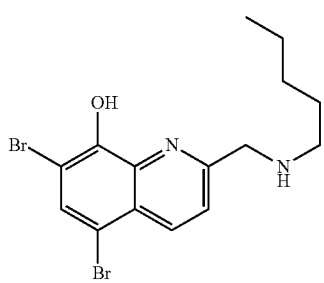

RA-HQ-2

Yield: 70% yield; 85 mg of RA-HQ-2 was isolated as a yellow solid.

$^1$H NMR (400 MHz, d$_6$-DMSO): 8.36 (d, J=8.6 Hz, 1H), 7.96 (s, 1H), 7.75 (d, J=8.7 Hz, 1H), 4.06 (s, 2H), 2.57 (t, J=7.1 Hz, 2H), 1.48 (p, J=7.7 Hz, 2H), 1.36-1.23 (m, 4H), 0.97-0.78 (m, 3H).

$^{13}$C NMR (100 MHz, d$_6$-DMSO): 153.0, 150.9, 137.7, 136.8, 133.7, 126.0, 122.7, 109.1, 105.4, 50.3, 47.4, 28.3, 25.1, 21.8, 13.9. HRMS (ESI): calcd for C$_{15}$H$_{18}$Br$_2$N$_2$ONa [M+Na]$^+$: 422.9678, found: 422.9663.

MP: 170-172° C.

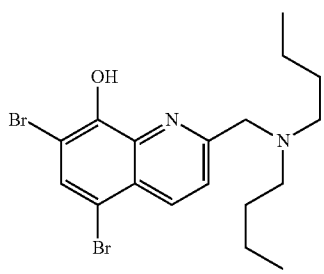

RA-HQ-3

Yield: 85% yield; 115 mg of RA-HQ-3 was isolated as a brown semisolid.

$^1$H NMR (400 MHz, CDCl$_3$): 8.35 (d, J=8.7 Hz, 1H), 7.82 (s, 1H), 7.79 (d, J=8.7 Hz, 1H), 3.87 (s, 2H), 2.53-2.43 (m, 4H), 1.53-1.40 (m, 4H), 1.37-1.18 (m, 4H), 0.88 (t, J=7.3 Hz, 6H).

$^{13}$C NMR (100 MHz, CDCl$_3$): 161.9, 149.6, 137.9, 136.2, 133.1, 125.8, 123.3, 110.2, 103.8, 60.7, 54.5, 29.6, 20.8, 14.3.

HRMS (ESI): calcd for C$_{18}$H$_{24}$Br$_2$N$_2$ONa [M+Na]$^+$: 465.0127, found: 465.0127.

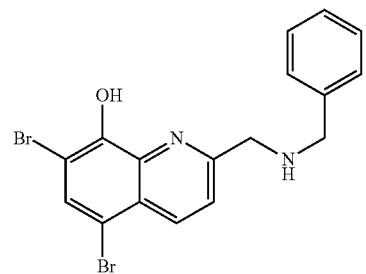

RA-HQ-4

Yield: 45% yield; 40 mg of RA-HQ-4 was isolated as a yellow solid.

$^1$H NMR (400 MHz, d$_6$-DMSO): 8.36 (d, J=8.7 Hz, 1H), 7.98 (s, 1H), 7.76 (d, J=8.7 Hz, 1H), 7.42-7.37 (m, 2H), 7.32 (dd, J=8.4, 6.7 Hz, 2H), 7.26-7.19 (m, 1H), 4.04 (s, 2H), 3.79 (s, 2H).

$^{13}$C NMR (100 MHz, d$_6$-DMSO): 160.8, 150.6, 140.7, 138.1, 135.4, 132.4, 128.1, 128.0, 126.6, 125.4, 122.8, 108.7, 104.7, 53.6, 52.6.

HRMS (ESI): calcd for C$_{16}$H$_{13}$Br$_2$N$_2$ONa [M+Na]$^+$: 442.9365, found: 442.9370. MP: 184-186° C.

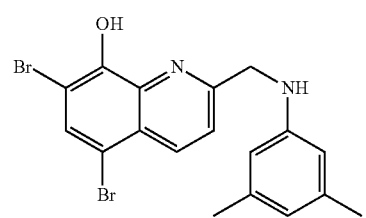

RA-HQ-6

Yield: 65% yield; 80 mg of RA-HQ-6 was isolated as a light yellow solid.

$^1$H NMR (400 MHz, CDCl$_3$): 8.34 (d, J=8.6 Hz, 1H), 7.84 (s, 1H), 7.61 (d, J=8.7 Hz, 1H), 6.42 (s, 1H), 6.31 (s, 2H), 4.66 (s, 2H), 2.23 (s, 6H).

$^{13}$C NMR (100 MHz, CDCl$_3$): 160.1, 149.3, 147.6, 139.3, 138.0, 136.9, 133.3, 125.8, 121.7, 120.5, 111.2, 110.3, 104.3, 49.7, 21.7.

HRMS (ESI): calcd for C$_{18}$H$_{16}$Br$_2$N$_2$ONa [M+Na]$^+$: 456.9522, found: 456.9488.

MP: 151-153° C.

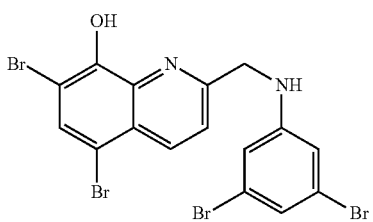

RA-HQ-10

Yield: 40% yield; 55 mg of RA-HQ-10 was isolated as a white solid.

$^1$H NMR (400 MHz, CDCl$_3$): 8.42 (d, J=8.7 Hz, 1H), 7.89 (s, 1H), 7.56 (d, J=8.7 Hz, 1H), 7.01 (dd, J=1.5, 1.5 Hz, 1H), 6.74 (d, J=1.7 Hz, 2H), 4.83 (br. s, 1H), 4.64 (d, J=2.8 Hz, 2H).

$^{13}$C NMR (100 MHz, CDCl$_3$): 8.42 (d, J=8.7 Hz, 1H), 7.89 (s, 1H), 7.56 (d, J=8.7 Hz, 1H), 7.01 (dd, J=1.5, 1.5 Hz, 1H), 6.74 (d, J=1.7 Hz, 2H), 4.83 (br. s, 1H), 4.64 (d, J=2.8 Hz, 2H).

HRMS (ESI): calcd for C$_{16}$H$_{11}$Br$_4$N$_2$O [M+H]$^+$: 562.7599, found: 562.7572.

MP: 149-151° C.

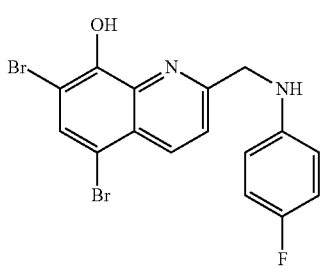

RA-HQ-12

Yield: 73% yield; 94 mg of RA-HQ-12 was isolated as a white solid.

$^1$H NMR (400 MHz, CDCl$_3$): 8.38 (d, J=8.7 Hz, 1H), 7.86 (s, 1H), 7.61 (d, J=8.7 Hz, 1H), 6.88 (t, J=8.7 Hz, 2H), 6.59 (dd, J=9.0, 4.3 Hz, 2H), 4.65 (s, 2H).

$^{13}$C NMR (100 MHz, CDCl$_3$): 159.7, 156.5 (d, J=236.2 Hz), 149.4, 143.9, 138.1, 137.1, 133.6, 126.0, 121.7, 116.1 (d, J=22.4 Hz), 114.2 (d, J=7.4 Hz), 110.4, 104.5, 50.3.

HRMS (ESI): calcd for C$_{16}$H$_{12}$Br$_2$FN$_2$O [M+H]$^+$: 426.9275, found: 426.9265.

MP: 148-150° C.

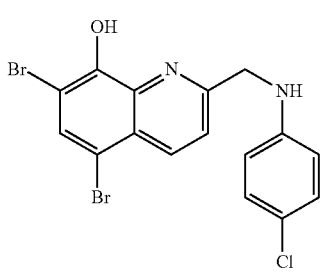

RA-HQ-13

Yield: 54% yield; 72 mg of RA-HQ-13 was isolated as a yellow solid.

$^1$H NMR (400 MHz, CDCl$_3$): 8.39 (d, J=8.7 Hz, 1H), 7.87 (s, 1H), 7.60 (d, J=8.7 Hz, 1H), 7.12 (d, J=8.7 Hz, 2H), 6.58 (d, J=8.7 Hz, 2H), 4.67 (s, 2H).

$^{13}$C NMR (100 MHz, CDCl$_3$): 159.4, 149.4, 146.1, 138.1, 137.2, 133.7, 129.5, 126.0, 123.2, 121.6, 114.4, 110.4, 104.6, 49.8.

HRMS (ESI): calcd for C$_{16}$H$_{12}$Br$_2$ClN$_2$O [M+H]$^+$: 442.8978, found: 442.8975.

MP: 141-143° C.

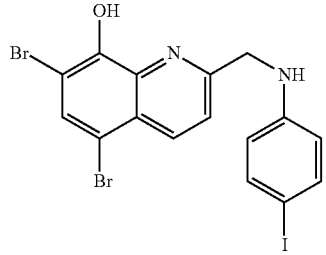

RA-HQ-14

Yield: 47% yield; 76 mg of RA-HQ-14 was isolated as a pale white solid.

$^1$H NMR (400 MHz, CDCl$_3$): 8.39 (d, J=8.7 Hz, 1H), 7.87 (s, 1H), 7.59 (d, J=8.7 Hz, 1H), 7.42 (d, J=8.8 Hz, 2H), 6.44 (d, J=8.9 Hz, 2H), 4.66 (s, 2H).

$^{13}$C NMR (100 MHz, CDCl$_3$): 159.3, 149.4, 147.1, 138.2, 138.1, 137.3, 133.7, 126.0, 121.6, 115.5, 110.4, 104.6, 79.3, 49.5.

HRMS (ESI): calcd for C$_{16}$H$_{12}$Br$_2$IN$_2$O [M+H]$^+$: 534.8336, found: 534.8337.

MP: 137-139° C.

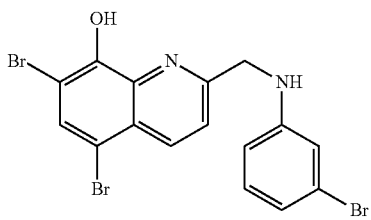

RA-HQ-15

Yield: 66% yield; 90 mg of RA-HQ-15 was isolated as a yellow solid.

$^1$H NMR (400 MHz, CDCl$_3$): 8.39 (d, J=8.7 Hz, 1H), 7.87 (s, 1H), 7.58 (d, J=8.7 Hz, 1H), 7.02 (t, J=8.0 Hz, 1H), 6.86 (d, J=7.8 Hz, 1H), 6.82 (t, J=2.1 Hz, 1H), 6.57 (dd, J=8.2, 1.6, 1H), 4.66 (s, 2H).

$^{13}$C NMR (100 MHz, CDCl$_3$): 159.0, 149.4, 148.9, 138.1, 137.3, 133.7, 130.9, 126.0, 123.6, 121.6, 121.3, 116.0, 112.0, 110.4, 104.6, 49.4.

HRMS (ESI): calcd for C$_{16}$H$_{12}$Br$_3$N$_2$O [M+H]$^+$: 486.8474, found: 486.8470.

MP: 141-143° C.

RA-HQ-16

Yield: 42% yield; 48 mg of RA-HQ-16 was isolated as a yellow solid.

¹H NMR (400 MHz, CDCl₃): 8.40 (d, J=8.7 Hz, 1H), 7.88 (s, 1H), 7.59 (d, J=8.7 Hz, 1H), 7.48 (dd, J=7.9, 1.5 Hz, 1H), 7.12 (ddd, J=8.1, 7.4, 1.5 Hz, 1H), 6.67-6.55 (m, 2H), 5.52 (s, 1H), 4.75 (d, J=4.6 Hz, 2H).

¹³C NMR (100 MHz, CDCl₃): 158.7, 149.4, 144.5, 138.0, 137.3, 133.7, 132.8, 128.8, 126.1, 121.5, 118.9, 112.0, 110.4, 110.4, 104.7, 49.4.

HRMS (ESI): calcd for $C_{16}H_{11}Br_3N_2ONa$ [M+Na]⁺: 508.8294, found: 508.8296.

MP: 151-153° C.

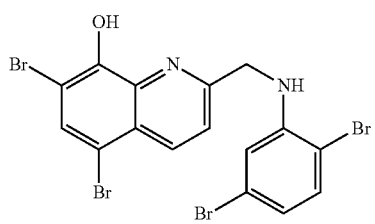

RA-HQ-17

Yield: 73% yield; 94 mg of RA-HQ-17 was isolated as a white solid.

¹H NMR (400 MHz, CDCl₃): 8.44 (d, J=8.7 Hz, 1H), 7.90 (s, 1H), 7.56 (d, J=8.7 Hz, 1H), 7.32 (d, J=8.1 Hz, 1H), 6.79-6.68 (m, 2H), 5.68 (t, J=5.5 Hz, 1H), 4.72 (d, J=5.4 Hz, 2H).

¹³C NMR (100 MHz, CDCl₃): 157.5, 149.4, 145.6, 137.9, 137.5, 133.9, 133.7, 126.2, 122.7, 121.6, 121.5, 114.7, 110.5, 108.9, 105.0, 48.9.

HRMS (ESI): calcd for $C_{16}H_{10}Br_4N_2ONa$ [M+H]⁺: 588.7379, found: 588.7353.

MP: 142-144° C.

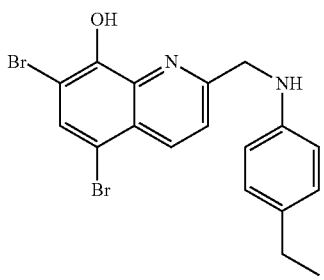

RA-HQ-18

Yield: 59% yield; 45 mg of RA-HQ-18 was isolated as a light yellow solid.

¹H NMR (400 MHz, CDCl₃): 8.34 (d, J=8.7 Hz, 1H), 7.84 (s, 1H), 7.63 (d, J=8.7 Hz, 1H), 7.02 (d, J=8.6 Hz, 2H), 6.61 (d, J=8.5 Hz, 2H), 4.66 (d, J=1.2 Hz, 2H), 2.54 (q, J=7.6 Hz, 2H), 1.18 (t, J=7.6 Hz, 3H).

¹³C NMR (100 MHz, CDCl₃): 160.3, 149.4, 145.5, 138.1, 137.0, 134.3, 133.4, 128.9, 125.9, 121.8, 113.4, 110.4, 104.3, 50.1, 28.1, 16.1.

HRMS (ESI): calcd for $C_{18}H_{17}Br_2N_2O$ [M+H]⁺: 436.9633, found: 436.9630.

MP: 138-140° C.

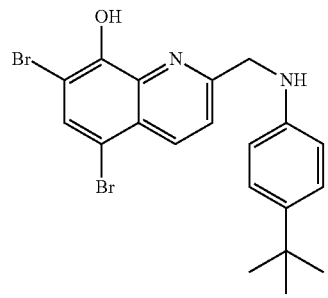

RA-HQ-19

Yield: 53% yield; 75 mg of RA-HQ-19 was isolated as a white solid.

¹H NMR (400 MHz, CDCl₃): 8.36 (d, J=8.7 Hz, 1H), 7.85 (s, 1H), 7.65 (d, J=8.7 Hz, 2H), 7.21 (d, J=8.7 Hz, 2H), 6.62 (d, J=8.7 Hz, 2H), 4.67 (s, 2H), 1.27 (s, 9H).

¹³C NMR (100 MHz, CDCl₃): 160.3, 149.4, 145.2, 141.3, 138.1, 137.0, 133.5, 126.4, 126.0, 121.8, 113.1, 110.4, 104.3, 50.2, 34.1, 31.7.

HRMS (ESI): calcd for $C_{20}H_{21}Br_2N_2O$ [M+H]⁺: 464.9996, found: 464.9995.

MP: 125-127° C.

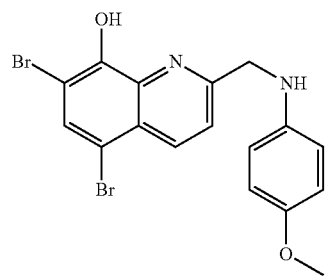

RA-HQ-20

Yield: 60% yield; 80 mg of RA-HQ-20 was isolated as a white solid.

¹H NMR (400 MHz, CDCl₃): 8.37 (d, J=8.7 Hz, 1H), 7.86 (s, 1H), 7.64 (d, J=8.7 Hz, 1H), 6.77 (d, J=9.0 Hz, 2H), 6.62 (d, J=8.7 Hz, 2H), 4.65 (s, 2H), 3.73 (s, 3H).

¹³C NMR (100 MHz, CDCl₃): 160.3, 152.9, 149.4, 141.8, 138.2, 137.0, 133.5, 126.0, 121.8, 115.3, 114.6, 110.4, 104.3, 56.0, 50.7.

HRMS (ESI): calcd for $C_{17}H_{14}Br_2N_2O_2Na$ [M+Na]⁺: 460.9295, found: 460.9282.

MP: 135-137° C.

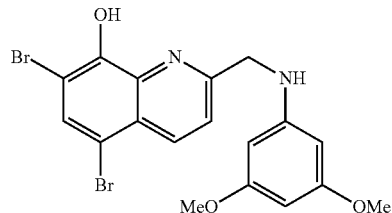

RA-HQ-21

Yield: 48% yield; 68 mg of RA-HQ-21 was isolated as a yellow semisolid.

¹H NMR (400 MHz, CDCl₃): 8.39 (d, J=8.7 Hz, 1H), 7.87 (s, 1H), 7.63 (d, J=8.7 Hz, 1H), 5.91 (t, J=2.1 Hz, 1H), 5.85 (d, J=2.1 Hz, 2H), 4.66 (s, 2H), 3.73 (s, 6H).

¹³C NMR (100 MHz, CDCl₃): 162.0, 159.7, 149.5, 149.3, 138.0, 137.0, 133.5, 125.9, 121.7, 110.4, 104.4, 92.2, 90.5, 55.4, 49.7.

HRMS (ESI): calcd for C₁₈H₁₆Br₂N₂O₃Na [M+Na]⁺: 488.9420, found: 488.9400.

RA-HQ-22

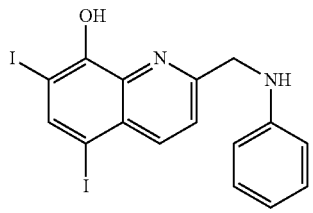

Yield: 55% yield; 26 mg of RA-HQ-22 was isolated as a white solid.

¹H NMR (400 MHz, CDCl₃): 8.26 (s, 1H), 8.20 (d, J=8.6 Hz, 1H), 7.57 (d, J=8.7 Hz, 1H), 7.18 (dd, J=8.3, 7.3 Hz, 2H), 6.75 (t, J=7.4 Hz, 1H), 6.67 (d, J=8.4 Hz, 2H), 4.68 (s, 2H).

¹³C NMR (100 MHz, CDCl₃): 159.9, 153.7, 147.7, 144.9, 141.5, 137.2, 129.6, 129.1, 122.4, 118.6, 113.4, 84.8, 77.7, 49.7.

HRMS (DART): calcd for C₁₆H₁₃I₂N₂O [M+H]⁺: 502.9112, found: 502.9111.

MP: 155-157° C.

RA-HQ-23

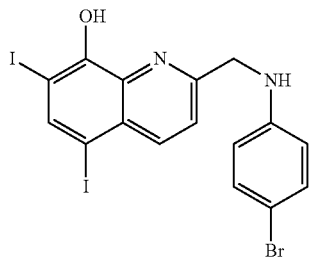

Yield: 35% yield; 30 mg of RA-HQ-23 was isolated as a light yellow solid.

¹H NMR (400 MHz, CDCl₃): 8.29 (s, 1H), 8.25 (dd, J=8.6, 1.5 Hz, 1H), 7.57 (dd, J=8.6, 1.6 Hz, 1H), 7.25 (d, J=8.0 Hz, 2H), 6.54 (dd, J=8.9, 2.1 Hz, 2H), 4.67 (s, 2H).

¹³C NMR (100 MHz, CDCl₃): 159.2, 153.6, 146.5, 145.0, 141.7, 137.1, 132.3, 129.1, 122.3, 114.8, 110.2, 84.9, 77.4, 49.5.

HRMS (DART): calcd for C₁₆H₁₂BrI₂N₂O [M+H]⁺: 580.8217, found: 580.8222.

MP: 144-146° C.

General Alkylation Procedure (A-HQ-1 to A-HQ-7)

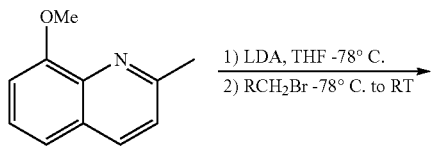

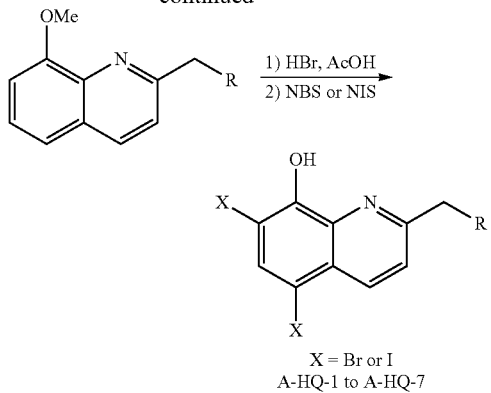

X = Br or I
A-HQ-1 to A-HQ-7

5,7-dibromo-2-pentylquinolin-8-ol (A-HQ-6)

To a stirring solution of 8-methoxyquinaldine (200 mg, 1.15 mmol) in 5 mL anhydrous tetrahydrofuran at −78° C., 1.3 molar solution of lithium diisopropylamide (1.3 mL, 1.5 mmol) was added via syringe under argon. The solution was allowed to stir for one hour and then 1-bromobutane (0.16 mL, 1.5 mmol) was added via syringe. The reaction was then allowed to warm to room temperature and stirred for an additional 24 hours. The reaction mixture was quenched using an aqueous solution of ammonium chloride, transferred to a separatory funnel and crude product was extracted using ethyl acetate (2×30 mL). The combined organic layer was sequentially washed with sodium bicarbonate and brine before the organic layer was collected and dried with anhydrous sodium sulfate, filtered, and concentrated in vacuo. The crude product was then purified via flash column chromatography using hexanes:ethyl acetate (8:2 to 7:3) to elute pure 8-methoxy-2-pentylquinoline as a clear oil (105 mg, 40%).

¹H NMR (400 MHz, CDCl₃): 7.99 (d, J=8.5 Hz, 1H), 7.35 (m, 1H), 7.31 (dd, J=8.2, 1.5 Hz, 1H), 7.30 (d, J=8.5 Hz, 1H), 6.99 (dd, J=7.5, 1.5 Hz, 1H), 4.04 (s, 3H), 3.01 (t, J=8.0 Hz, 2H), 1.96-1.70 (m, 2H), 1.48-1.21 (m, 4H), 0.88 (t, J=7.0 Hz, 3H).

¹³C NMR (100 MHz, CDCl₃): 162.3, 155.1, 139.8, 136.2, 127.9, 125.7, 121.8, 119.5, 107.7, 56.1, 39.7, 32.0, 30.0, 22.7, 14.2.

HRMS (DART): calcd for C₁₅H₂₀NO [M+H]⁺: 230.1539, found: 230.1532.

To a stirring solution of 8-methoxy-2-pentylquinoline (105 mg, 0.46 mmol) in 5 mL glacial acetic acid at room temperature, 5 mL hydrobromic acid was added and the mixture was refluxed for 48 hours. The solution was then then allowed to cool down and neutralized with a saturated aqueous solution of sodium bicarbonate. The crude product was extracted with dichloromethane (3×20 mL) and combined organic layers was washed with brine, dried with anhydrous sodium sulfate, filtered, and concentrated in vacuo. The crude material was subjected to column chromatography eluting with hexanes:ethyl acetate (5:1 to 4:1) to obtain pure 2-pentylquinolin-8-ol as clear oil (90 mg, 91%).

¹H NMR (400 MHz, CDCl₃): 8.04 (d, J=8.4 Hz, 1H), 7.37 (dd, J=8.2, 7.6 Hz, 1H), 7.33-7.24 (m, 2H), 7.14 (dd, J=7.5, 1.3 Hz, 1H), 3.17-2.76 (m, 2H), 1.89-1.75 (m, 2H), 1.41-1.31 (m, 4H), 0.96-0.85 (m, 3H).

¹³C NMR (100 MHz, CDCl₃): 161.1, 152.0, 137.9, 136.3, 127.0, 126.8, 122.5, 117.7, 109.8, 38.7, 31.8, 29.3, 22.8, 14.3.

HRMS (DART): calcd for $C_{14}H_{18}NO$ [M+H]$^+$: 216.1383, found: 216.1382.

To a stirring solution of 2-pentylquinolin-8-ol (151 mg, 0.70 mmol) in 10 mL toluene at room temperature, N-bromosuccinimide (272 mg, 1.54 mmol) was added and the reaction mixture was stirred for 2 hours. After completion of the reaction, the solution was concentrated in vacuo, then adsorbed onto silica using dichloromethane and concentrated in vacuo before being applied to a column. The crude product was then purified via flash column chromatography using hexanes:ethyl acetate (5:1 to 3:1) to elute pure 5,7-dibromo-2-pentylquinolin-8-ol A-HQ-6 as light green semisolid (105 mg, 40%).

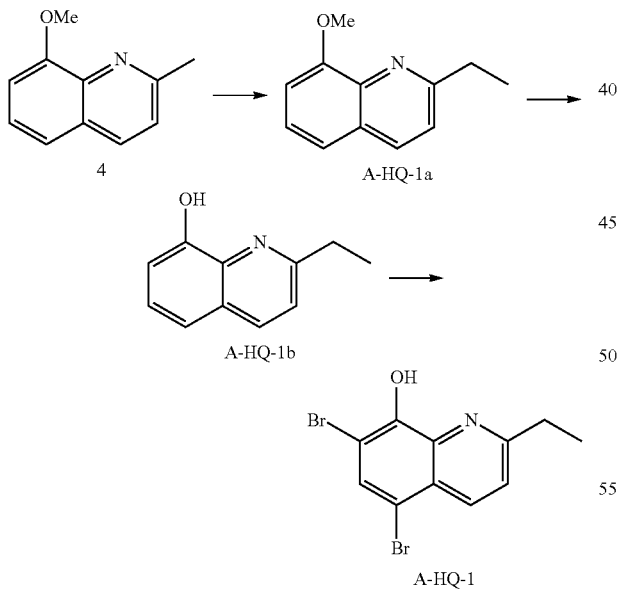

Yield: 40% yield; 105 mg of A-HQ-6 was isolated as a clear oil.
$^1$H NMR (400 MHz, CDCl$_3$): 8.26 (d, J=8.6 Hz, 1H), 7.77 (s, 1H), 7.39 (d, J=8.6 Hz, 1H), 2.97 (t, J=7.8 Hz, 2H), 1.89-1.72 (m, 2H), 1.44-1.31 (m, 4H), 0.98-0.85 (m, 3H).
$^{13}$C NMR (100 MHz, CDCl$_3$): 162.9, 149.3, 138.1, 136.2, 132.8, 125.1, 123.6, 110.1, 103.7, 38.4, 31.7, 29.2, 22.7, 14.2.
HRMS (DART): calcd for $C_{14}H_{16}Br_2NO$ [M+H]$^+$: 371.9593, found: 371.9576.

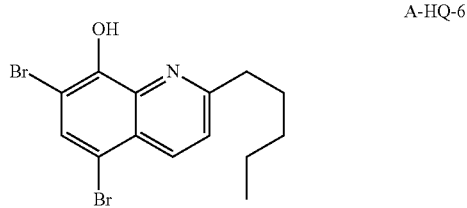 [SMILES: CCCCCc1ccc2c(Br)cc(Br)c(O)c2n1]

Yield of A-HQ-1a: 44% yield; 190 mg of A-HQ-1a was isolated as a light yellow solid.
$^1$H NMR (400 MHz, CDCl$_3$): 7.97 (dd, J=8.3, 1.2 Hz, 1H), 7.39-7.24 (m, 3H), 6.96 (dt, J=7.5, 1.2 Hz, 1H), 4.02 (s, 3H), 3.03 (q, J=7.6 Hz, 2H), 1.35 (td, J=7.7, 0.9 Hz, 3H).
$^{13}$C NMR (100 MHz, CDCl$_3$): 163.3, 155.1, 139.7, 136.4, 127.9, 125.8, 121.3, 119.5, 107.7, 56.2, 32.7, 14.4.

MP: 68-70° C., lit 70-71° C.
Yield of A-HQ-1b: 80% yield; 65 mg of A-HQ-1b was isolated as a light yellow solid.
$^1$H NMR (400 MHz, CDCl$_3$): 8.04 (d, J=8.5 Hz, 1H), 7.39 (t, J=7.9 Hz, 1H), 7.33-7.24 (m, 2H), 7.16 (dd, J=7.5, 1.3 Hz, 1H), 3.00 (q, J=7.6 Hz, 2H), 1.41 (t, J=7.6 Hz, 3H).
$^{13}$C NMR (100 MHz, CDCl$_3$): 161.8, 151.9, 137.7, 136.4, 126.9, 126.8, 122.0, 117.7, 109.9, 31.7, 13.6.
MP: 81-83° C.
Yield of A-HQ-1: 51% yield; 35 mg of A-HQ-1 was isolated as a light yellow solid.
$^1$H NMR (400 MHz, CDCl$_3$): 8.31 (d, J=8.7 Hz, 1H), 7.81 (s, 1H), 7.43 (d, J=8.7 Hz, 1H), 3.03 (q, J=7.6 Hz, 2H), 1.40 (t, J=7.6 Hz, 3H).
$^{13}$C NMR (100 MHz, CDCl$_3$): 163.7, 149.4, 138.2, 136.3, 132.8, 125.2, 123.2, 110.2, 103.7, 31.5, 13.4.
HRMS (DART): calcd for $C_{11}H_{10}Br_2NO$ [M+H]$^+$: 329.9124, found: 329.9114.
MP: 91-93° C.

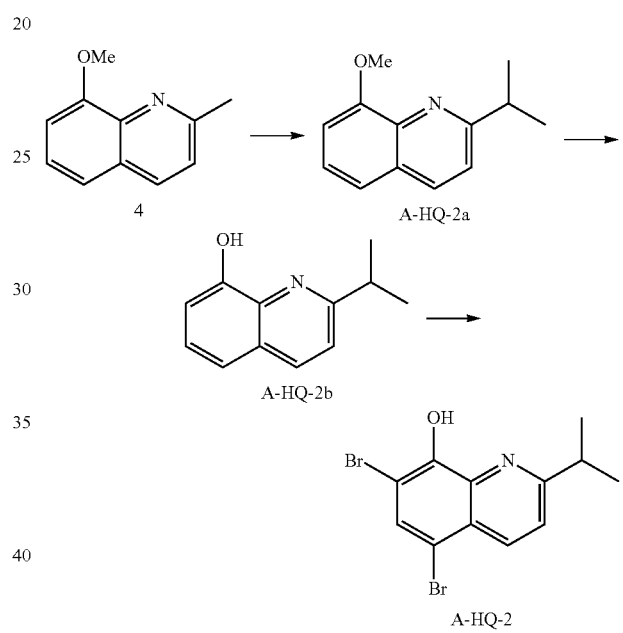

Yield of A-HQ-2a: 20% yield, 65 mg A-HQ-2a, a side product of AH-Q-la; was isolated as a clear oil.
$^1$H NMR (400 MHz, CDCl$_3$): 8.04 (d, J=8.5 Hz, 1H), 7.42-7.29 (m, 3H), 7.01 (dd, J=7.5, 1.6 Hz, 1H), 4.06 (s, 3H), 3.47-3.31 (m, 1H), 1.38 (dd, J=7.0, 1.8 Hz, 6H).
$^{13}$C NMR (100 MHz, CDCl$_3$): 167.1, 155.2, 139.5, 136.6, 128.2, 125.8, 119.6, 119.2, 107.9, 56.3, 37.8, 23.0.
Yield of A-HQ-2b: 90% yield; 95 mg of A-HQ-2b was isolated as a white solid.
$^1$H NMR (400 MHz, CDCl$_3$): 8.06 (d, J=8.5 Hz, 1H), 7.39 (dd, J=8.3, 7.5 Hz, 1H), 7.35 (d, J=8.5 Hz, 1H), 7.29 (dd, J=8.2, 1.3 Hz, 1H), 7.16 (dd, J=7.6, 1.3 Hz, 1H), 3.24 (p, J=6.9 Hz, 1H), 1.40 (d, J=6.9 Hz, 6H).
$^{13}$C NMR (100 MHz, CDCl$_3$): 165.5, 152.0, 137.6, 136.5, 127.1, 126.9, 120.9, 117.7, 109.8, 36.7, 22.6.
HRMS (DART): calcd for $C_{12}H_{14}NO$ [M+H]$^+$: 188.1070, found: 188.1063.
MP: 108-110° C.
Yield of A-HQ-2: 56% yield; 35 mg of A-HQ-2 was isolated as a light yellow solid.
$^1$H NMR (400 MHz, CDCl$_3$): 8.34 (d, J=8.7 Hz, 1H), 7.82 (s, 1H), 7.47 (d, J=8.7 Hz, 1H), 3.28 (septet, J=6.9 Hz, 1H), 1.40 (d, J=6.9 Hz, 6H).

$^{13}$C NMR (100 MHz, CDCl$_3$): 167.4, 149.5, 138.1, 136.5, 132.9, 125.4, 122.2, 110.2, 103.6, 36.6, 22.5.

HRMS (ESI): calcd for C$_{12}$H$_{12}$Br$_2$NO [M+H]$^+$: 343.9280, found: 343.9261.

MP: 84-86° C.

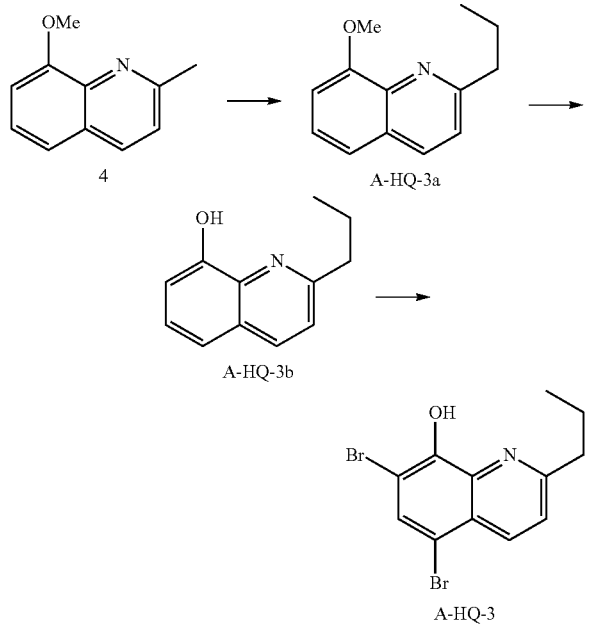

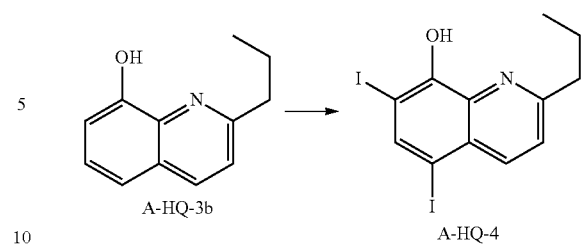

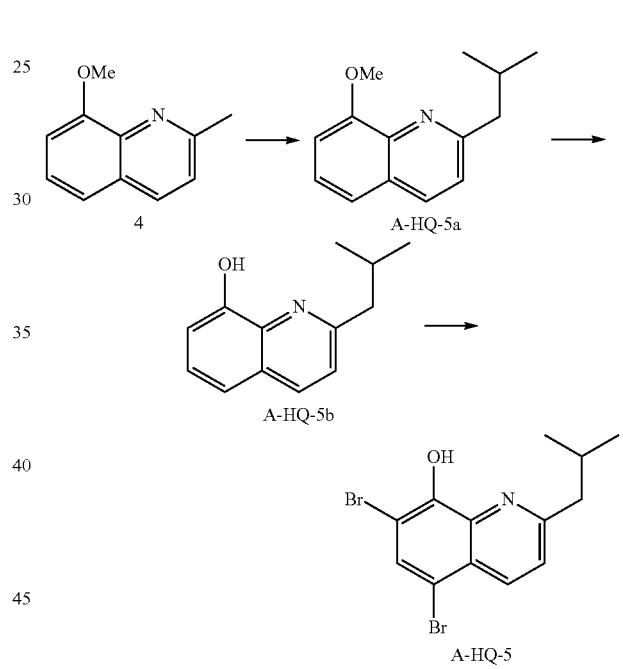

Yield of A-HQ-3a: 35% yield; 160 mg of A-HQ-3a was isolated as a yellow oil.

$^1$H NMR (400 MHz, CDCl$_3$): 7.97 (d, J=8.4 Hz, 1H), 7.34 (t, J=7.8 Hz, 1H), 7.31-7.25 (m, 2H), 6.97 (d, J=7.4 Hz, 1H), 4.02 (s, 3H), 2.98 (dd, J=9.2, 6.7 Hz, 2H), 1.81 (sextet, J=7.7 Hz, 2H), 0.99 (t, J=7.3 Hz, 3H).

$^{13}$C NMR (100 MHz, CDCl$_3$): 162.0, 155.0, 139.7, 136.1, 127.9, 125.7, 121.8, 119.4, 107.6, 56.1, 41.5, 23.5, 14.2.

HRMS (DART): calcd for C$_{13}$H$_{16}$NO [M+H]$^+$: 202.1226, found: 202.1230.

Yield of A-HQ-3b: 65% yield; 160 mg of A-HQ-3b was isolated as a light yellow oil.

$^1$H NMR (400 MHz, CDCl$_3$): 8.04 (d, J=8.5 Hz, 1H), 7.38 (t, J=7.9 Hz, 1H), 7.32-7.25 (m, 2H), 7.15 (dd, J=7.5, 1.2 Hz, 1H), 2.94 (m, 2H), 1.87 (sext, J=7.4 Hz, 2H), 1.02 (t, J=7.4 Hz, 3H).

$^{13}$C NMR (100 MHz, CDCl$_3$): 160.8, 152.0, 137.8, 136.3, 127.0, 126.8, 122.5, 117.7, 109.8, 40.7, 22.9, 14.1.

HRMS (DART): calcd for C$_{12}$H$_{14}$NO [M+H]$^+$: 188.1070, found: 188.1079.

Yield of A-HQ-3: 40% yield; 26 mg of A-HQ-3 was isolated as a light yellow solid.

$^1$H NMR (400 MHz, CDCl$_3$): 8.29 (d, J=8.6 Hz, 1H), 7.80 (s, 1H), 7.41 (d, J=8.6 Hz, 1H), 2.96 (dd, J=8.4, 6.9 Hz, 2H), 1.86 (sextet, J=7.4 Hz, 2H), 1.00 (t, J=7.4 Hz, 3H).

$^{13}$C NMR (100 MHz, CDCl$_3$): 162.7, 149.4, 138.2, 136.2, 132.8, 125.2, 123.7, 110.2, 103.6, 40.4, 22.8, 14.1.

HRMS (ESI): calcd for C$_{12}$H$_{12}$Br$_2$NO [M+H]$^+$: 343.9280, found: 343.9260.

MP: 74-75° C.

Yield of A-HQ-4: 70% yield; 60 mg of A-HQ-4 was isolated as a light yellow solid.

$^1$H NMR (400 MHz, CDCl$_3$): 8.22 (s, 1H), 8.16 (d, J=8.6 Hz, 1H), 7.39 (d, J=8.6 Hz, 1H), 2.97 (dd, J=8.3, 6.8 Hz, 2H), 1.85 (sextet, J=7.4 Hz, 2H), 1.00 (t, J=7.3 Hz, 3H).

$^{13}$C NMR (100 MHz, CDCl$_3$): 162.6, 153.6, 144.0, 140.6, 137.2, 128.3, 124.4, 84.7, 77.4, 40.2, 22.7, 14.0.

HRMS (DART): calcd for C$_{12}$H$_{12}$I$_2$NO [M+H]$^+$: 439.9003, found: 439.9003.

MP: 94-95° C.

Yield of A-HQ-5a: 35% yield; 160 mg of A-HQ-5a was isolated as a yellow oil.

$^1$H NMR (400 MHz, CDCl$_3$): 7.99 (d, J=8.4 Hz, 1H), 7.39-7.30 (m, 2H), 7.27 (d, J=8.4 Hz, 1H), 7.00 (dd, J=7.4, 1.5 Hz, 1H), 4.04 (s, 3H), 2.91 (d, J=7.5 Hz, 2H), 2.22 (m, 1H), 0.95 (d, J=6.6 Hz, 6H).

$^{13}$C NMR (100 MHz, CDCl$_3$): 161.4, 155.2, 140.0, 135.9, 127.9, 125.7, 122.6, 119.5, 107.8, 56.2, 48.4, 29.4, 22.7.

HRMS (DART): calcd for C$_{14}$H$_{18}$NO [M+H]$^+$: 216.1383, found: 216.1388.

Yield of A-HQ-5b: 84% yield; 55 mg of A-HQ-5b was isolated as a yellow oil.

$^1$H NMR (400 MHz, CDCl$_3$): 8.04 (d, J=8.4 Hz, 1H), 7.39 (dd, J=8.3, 7.5 Hz, 1H), 7.32-7.22 (m, 2H), 7.16 (dd, J=7.6, 1.3 Hz, 1H), 2.83 (d, J=7.2 Hz, 2H), 2.24 (m, 1H), 0.98 (d, J=6.6 Hz, 6H).

$^{13}$C NMR (100 MHz, CDCl$_3$): 160.2, 152.0, 137.9, 136.1, 127.0, 126.8, 123.0, 117.7, 109.8, 47.9, 29.3, 22.7.

HRMS (DART): calcd for $C_{13}H_{16}NO$ [M+H]$^+$: 202.1226, found: 202.1220.

Yield of A-HQ-5: 75% yield; 55 mg of A-HQ-5 was isolated as a light green semisolid.

$^1$H NMR (400 MHz, CDCl$_3$): 8.30 (d, J=8.6 Hz, 1H), 7.80 (s, 1H), 7.39 (d, J=8.6 Hz, 1H), 2.86 (d, J=7.2 Hz, 2H), 2.21 (m, 1H), 0.96 (d, J=6.6 Hz, 6H).

$^{13}$C NMR (100 MHz, CDCl$_3$): 162.1, 149.4, 138.1, 136.2, 132.9, 125.2, 124.2, 110.2, 103.9, 47.5, 29.4, 22.7.

HRMS (DART): calcd for $C_{13}H_{14}Br_2NO$ [M+H]$^+$: 357.9437, found: 357.9435.

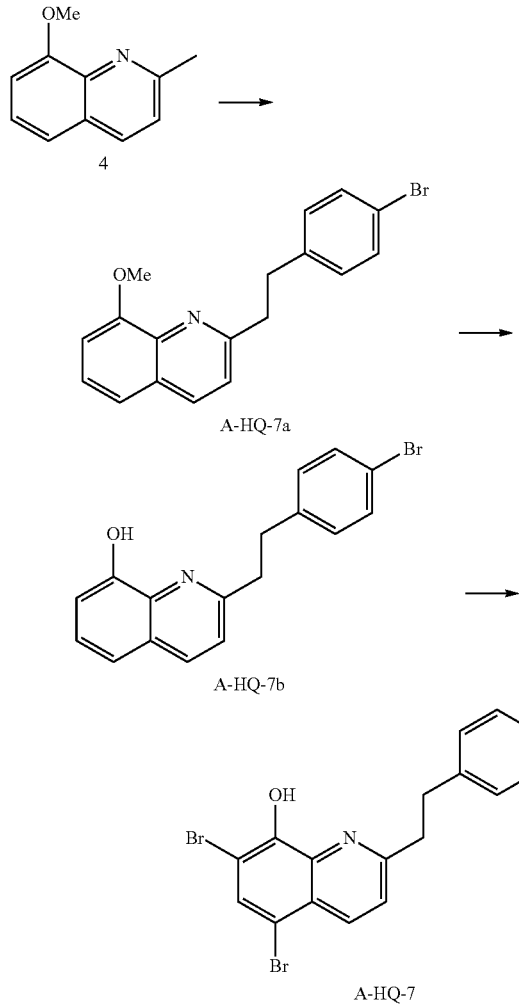

Yield of A-HQ-7a: 45% yield; 230 mg of A-HQ-7a was isolated as a yellow oil.

$^1$H NMR (400 MHz, CDCl$_3$): 8.02 (d, J=8.4 Hz, 1H), 7.51-7.32 (m, 4H), 7.24 (d, J=8.4 Hz, 1H), 7.12 (d, J=8.3 Hz, 2H), 7.06 (dd, J=7.6, 1.3 Hz, 1H), 4.09 (s, 3H), 3.37-3.28 (m, 2H), 3.12 (dd, J=9.7, 6.5 Hz, 2H).

$^{13}$C NMR (100 MHz, CDCl$_3$): 160.4, 155.0, 140.5, 139.8, 136.3, 131.4, 130.3, 127.9, 126.0, 121.9, 119.7, 119.5, 107.8, 56.1, 40.7, 35.4.

HRMS (ESI): calcd for $C_{18}H_{16}BrNONa$ [M+Na]$^+$: 364.0307, found: 364.0296.

Yield of A-HQ-7b: 84% yield; 55 mg of A-HQ-7b was isolated as a yellow oil.

$^1$H NMR (400 MHz, CDCl$_3$): 8.04 (d, J=8.4 Hz, 1H), 7.39 (dd, J=8.3, 7.5 Hz, 1H), 7.32-7.22 (m, 2H), 7.16 (dd, J=7.6, 1.3 Hz, 1H), 2.83 (d, J=7.2 Hz, 2H), 2.24 (m, 1H), 0.98 (d, J=6.6 Hz, 6H).

$^{13}$C NMR (100 MHz, CDCl$_3$): 160.2, 152.0, 137.9, 136.1, 127.0, 126.8, 123.0, 117.7, 109.8, 47.9, 29.3, 22.7.

HRMS (DART): calcd for $C_{13}H_{16}NO$ [M+H]$^+$: 202.1226, found: 202.1220.

Yield of A-HQ-7: 75% yield; 55 mg of A-HQ-7 was isolated as a light green semisolid.

$^1$H NMR (400 MHz, CDCl$_3$): 8.30 (d, J=8.6 Hz, 1H), 7.80 (s, 1H), 7.39 (d, J=8.6 Hz, 1H), 2.86 (d, J=7.2 Hz, 2H), 2.21 (m, 1H), 0.96 (d, J=6.6 Hz, 6H).

$^{13}$C NMR (100 MHz, CDCl$_3$): 162.1, 149.4, 138.1, 136.2, 132.9, 125.2, 124.2, 110.2, 103.9, 47.5, 29.4, 22.7.

HRMS (DART): calcd for $C_{13}H_{14}Br_2NO$ [M+H]$^+$: 357.9437, found: 357.9435.

Biological Assays

Minimum Inhibitory Concentration (MIC) Susceptibility Assay (in 96-Well Plate)

The minimum inhibitory concentration (MIC) for each compound was determined by the broth microdilution method as recommended by the Clinical and Laboratory Standards Institute (CLSI). In a 96-well plate, eleven two-fold serial dilutions of each compound were made in a final volume of 100 μL Luria Broth. Each well was inoculated with ~10$^5$ bacterial cells at the initial time of incubation, prepared from a fresh log phase culture (OD$_{600}$ of 0.5 to 1.0 depending on bacterial strain). The MIC was defined as the lowest concentration of test compound that prevented bacterial growth after incubating 16 to 18 hours at 37° C. The concentration range tested for each compound during this study was 0.10 to 100 μM. DMSO served as the vehicle and negative control in each microdilution MIC assay. DMSO was serially diluted with a top concentration of 1% v/v. Bacterial strains used: methicillin-resistant *Staphylococcus aureus*-2 (MRSA-2; clinical isolate from Shands Hospital in Gainesville, Fla.), methicillin-resistant *Staphylococcus epidermidis* (MRSE; ATCC 35984), vancomycin-resistant *Enterococcus faecium* (VRE, ATCC 700221).

Mechanistic Investigations with Metal(II)-Cations

Figure 8:
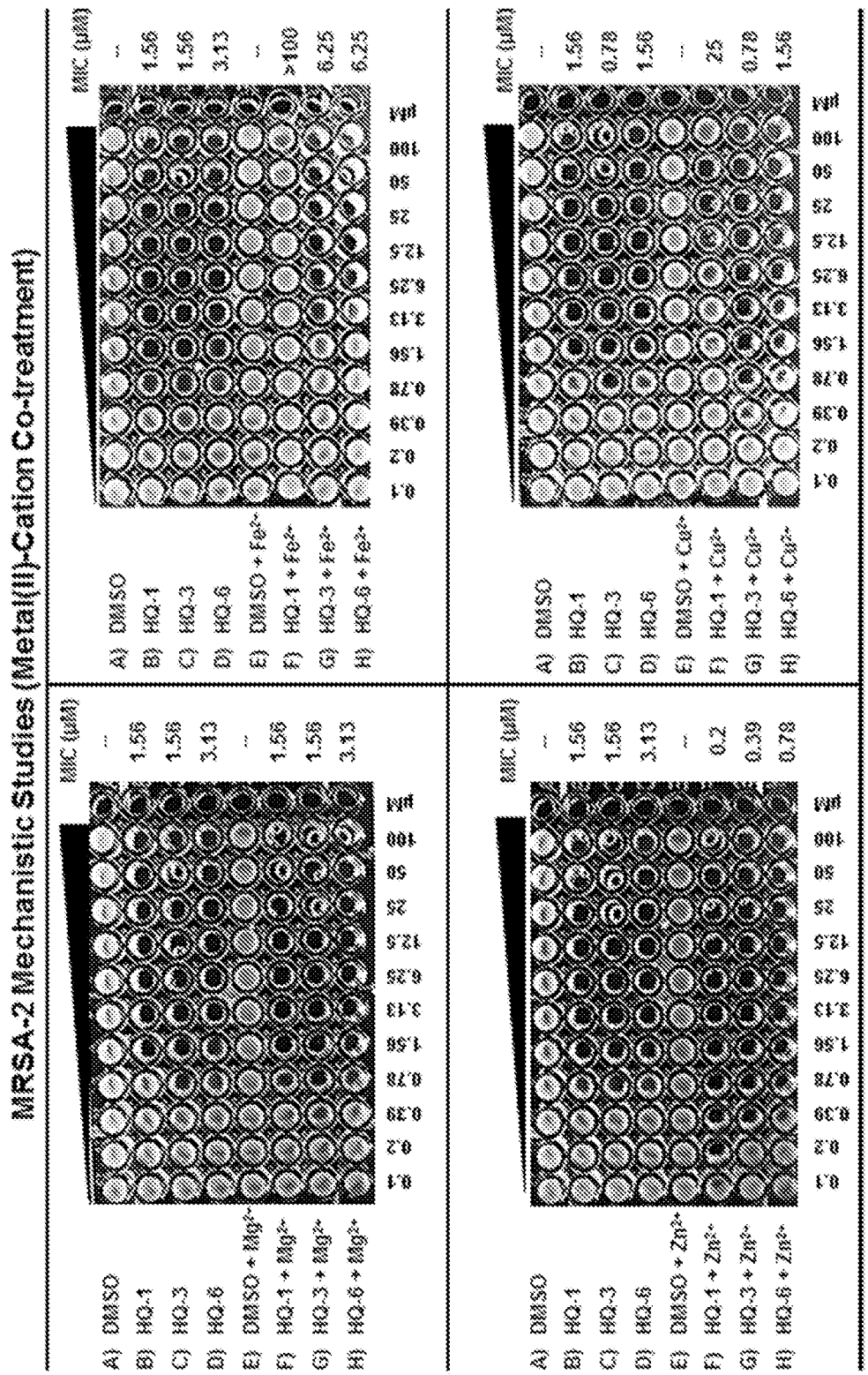
FIG. 8 shows exemplary results of MRSA-2 mechanistic studies. MRSA-2 was treated with certain compounds in the presence or absence of certain metal ions ($Mg^{2+}$ (top left panel); $Fe^{2+}$ (top right panel); $Zn^{2+}$ (bottom left panel); $Cu^{2+}$ (bottom right panel)).

Mechanistic investigations with metal(II)-cation were performed similar to standard MIC assays, with the addition of 200 μM of the metal salt (copper (II) sulfate, magnesium (II) sulfate, ammonium iron (II) sulfate hexahydrate and zinc (II) chloride). See Table 1 and FIG. 8 for "loss of antibacterial activity" results with MRSA-2.

TABLE 1

Mechanistic investigations of select HQ compounds against MRSA-2. All concentrations are in μM.

| | | | MRSA-2 | | | | | |
|---|---|---|---|---|---|---|---|---|
| Compound | MIC | MIC w/Fe$^{2+}$ | Fold Δ | MIC w/Cu$^{2+}$ | Fold Δ | MIC w/Mg$^{2+}$ | Fold Δ | MIC w/Zn$^{2+}$ | Fold Δ |
| HQ-1 | 1.13$^{a,b}$ | >100$^b$ | +88$^b$ | 25$^b$ | +22$^b$ | 1.56 | n.a. | 0.15$^{a,b}$ | −8$^b$ |
| | 0.78$^{a,c}$ | >100$^c$ | +88$^c$ | 25$^c$ | +32$^c$ | | | 0.1$^{a,c}$ | −8$^c$ |
| HQ-3 | 1.13$^a$ | 6.2$^a$ | +6 | 0.78 | n.a. | 1.56 | n.a. | 0.39 | −3 |
| HQ-6 | 4.69$^a$ | 9.38$^a$ | +2 | 1.13$^a$ | −4 | 3.13 | n.a. | 0.78 | −6 |

TABLE 1-continued

Mechanistic investigations of select HQ compounds against MRSA-2. All concentrations are in µM.

| | MRSA-2 | | | | | | | |
|---|---|---|---|---|---|---|---|---|
| Compound | MIC | MIC w/Fe$^{2+}$ | Fold Δ | MIC w/Cu$^{2+}$ | Fold Δ | MIC w/Mg$^{2+}$ | Fold Δ | MIC w/Zn$^{2+}$ | Fold Δ |
| A-HQ-4 | 1.56 | >100 | +64 | 12.5 | +8 | n.a. | n.a. | 0.2 | −8 |
| A-HQ-7 | 9.38$^a$ | >100 | +11 | >100 | +11 | n.a. | n.a. | 1.17$^a$ | −8 |
| RA-HQ-1 | 3.13 | 3.13 | n.a. | 3.13 | n.a. | n.a. | n.a. | 1.17$^a$ | −3 |
| RA-HQ-2 | 3.13 | 3.13 | n.a. | 2.35$^a$ | n.a. | n.a. | n.a. | 1.17$^a$ | −3 |
| RA-HQ-11 | >100 | >100 | n.a. | >100 | n.a. | >100 | n.a. | >100 | n.a. |

$^a$Corresponds to the midpoint value of a 2-fold range (in MIC) of a two independent experiments.
$^b$First batch.
$^c$Second batch.
"Fold Δ" denotes the change in antibacterial activity according to MIC values.
"+" denotes increase in MIC value/loss of antibacterial activity.
"−" denotes decrease in MIC value/increase of antibacterial activity.
"n.a." denotes insignificant changes in MIC values.

Figure 9:
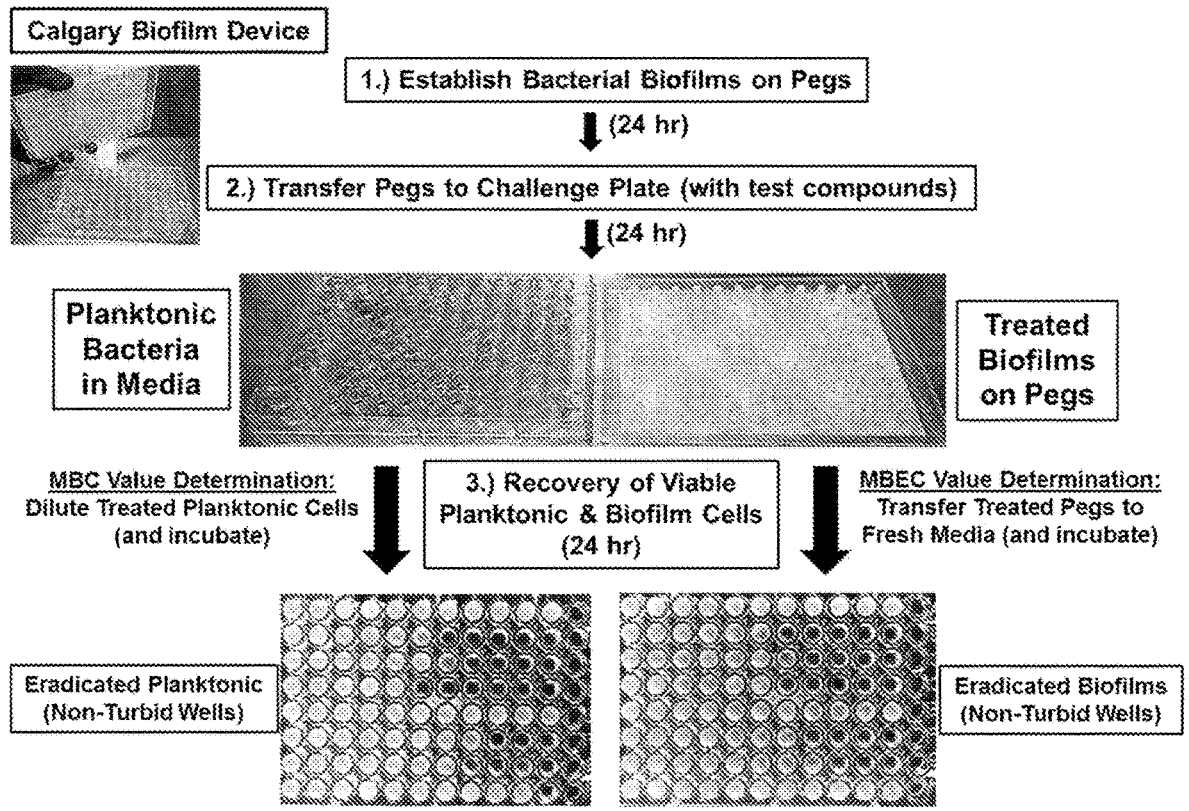
FIG. 9 shows a flow chart of the determination of minimum bactericidal concentrations (MBCs) and minimum biofilm eradication concentrations (MBECs) using the Calgary Biofilm Device. The bottom panel shows viable biofilm cells determined from a CBD assay (from treated and untreated pegs).

Calgary Biofilm Device (CBD) Experiments: Determination of Minimum Bactericidal Concentrations (MBC) and Minimum Biofilm Eradication Concentrations (MBEC) Using the Calgary Biofilm Device Biofilm eradication experiments were performed using the Calgary Biofilm Device to determine MBC/MBEC values for various compounds of interest (Innovotech, product code: 19111). The Calgary device (96-well plate with lid containing 96 total pegs to establish biofilms; 1 peg/well) was inoculated with 125 µL of a mid-log phase culture diluted 1,000-fold in tryptic soy broth with 0.5% glucose (TSBG) to establish bacterial biofilms after incubation at 37° C. for 24 hours. The lid of the Calgary device was then removed, washed and transferred to another 96-well plate containing 2-fold serial dilutions of the test compounds (the "challenge plate"). The total volume of media with compound in each well in the challenge plate was 150 µL. The Calgary device was then incubated at 37° C. for 24 hours. The lid was then removed from the challenge plate and MBC/MBEC values were determined using different final assays. To determine MBC values, 20 µL of the challenge plate was transferred into a fresh 96-well plate containing 180 µL TSBG and incubated overnight at 37° C. The MBC values were determined as the concentration giving a lack of visible bacterial growth (e.g., turbidity). For determination of MBEC values, the Calgary device lid (with attached pegs/treated biofilms) was transferred to a new 96-well plate containing 150 µL of fresh TSBG media in each well and incubated for 24 hours at 37° C. to allow viable biofilms to grow and disperse resulting in turbidity after the incubation period. MBEC values were determined as the lowest test concentration that resulted in eradicated biofilm (e.g., wells that had no turbidity after final incubation period). In select experiments, treated pegs from the Calgary device were removed from lead biofilm eradicators after final incubation, sonicated for 30 minutes in PBS and plated out to determine biofilm cell killing (e.g., colony forming unit per milliliter, CFU/mL). (FIG. 9 shows a flow chart of the determination of minimum bactericidal concentrations (MBC) and minimum biofilm eradication concentrations (MBEC) using the Calgary Biofilm Device)

Figure 7:
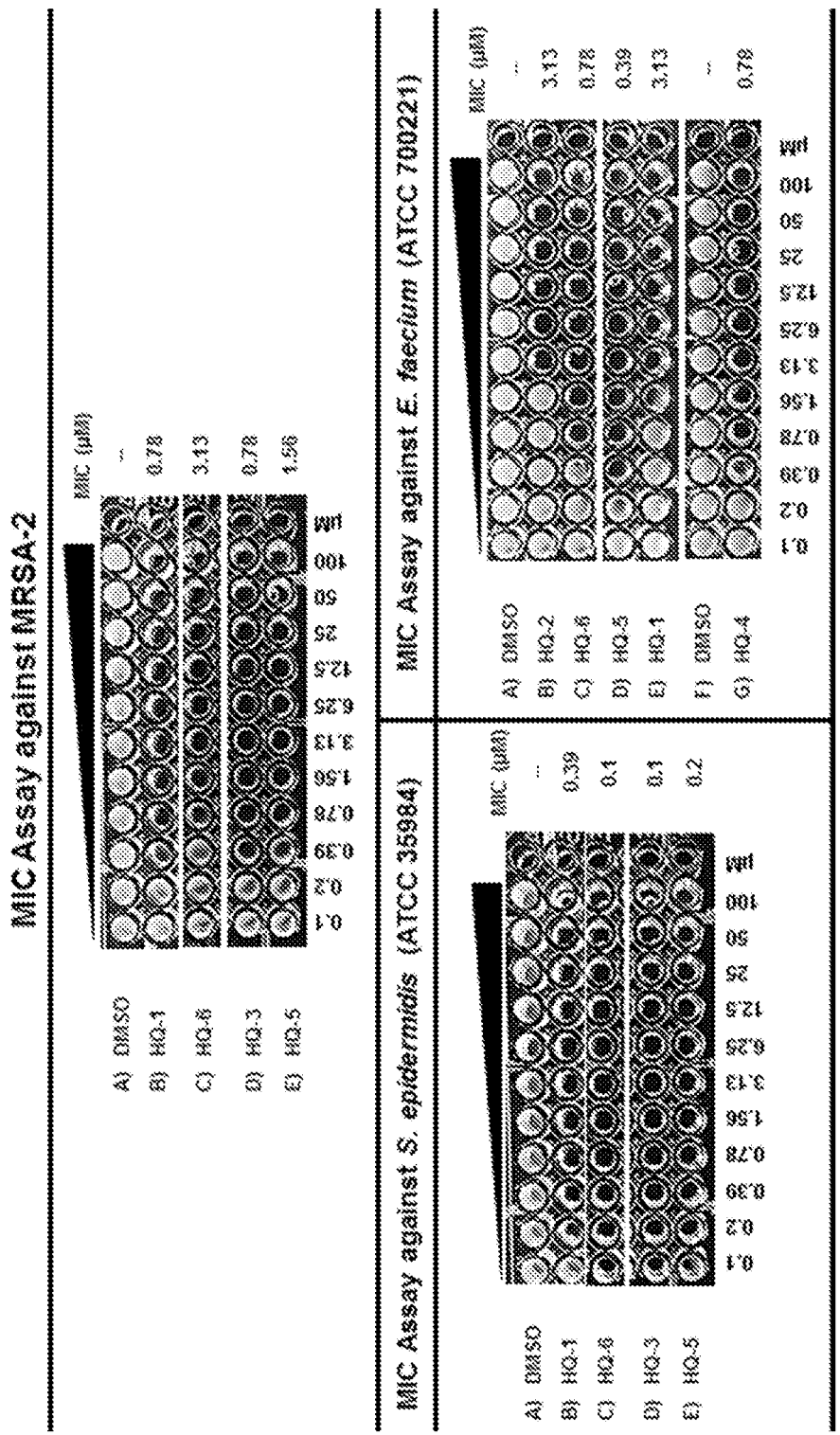
FIG. 7 shows exemplary results of MIC assays against MRSA-2 (top panel), *Staphylococcus epidermidis* (ATCC 35984) (bottom left panel), and *Enterococcus faecium* (ATCC 700221) (bottom right panel).

Note: MRSA-2, S. epidermidis (ATCC 35984) and VRE (ATCC 700221) were tested using these assay parameters (FIG. 7).

Hemolysis Assay

Freshly drawn human red blood cells (hRBC with ethylenediaminetetraacetic acid (EDTA) as an anticoagulant) were washed with Tris-buffered saline (0.01M Tris-base, 0.155M sodium chloride (NaCl), pH 7.2) and centrifuged for 5 minutes at 3500 rpm. The washing was repeated three times with the buffer. In 96-well plate, the test compounds were added to the buffer. Then 50 µL of 2% of hRBCs in the buffer were added to the test plate to make the final concentration to be 200 µM of each compound. The plate was then incubated for 1 hour at 37° C. After incubation, the plate is centrifuged for 5 minutes at 3500 rpm. Then 80 µL of the supernatant were transferred to another 96-well plate and the Optical Density (OD) was read at 405 nm. DMSO served as the negative control (0% hemolysis) and Triton X served as the positive control (100% hemolysis). The percent of hemolysis was calculated as ($OD_{405}$ of the compound-$OD_{405}$ DMSO)/($OD_{405}$ Triton X-$OD_{405}$ buffer).

Results and Discussion

Recently halogenated quinoline-1 (HQ-1; FIG. 1) has been identified as a small molecule capable of eradicating methicillin-resistant Staphylococcus aureus biofilms with a minimum biofilm eradication concentration (MBEC) of 250 µM (79 µg/mL).[22] Halogenated quinolines elicit their antibacterial activities through a metal(II)-dependent mechanism;[22,23] however, HQs are >100-fold more potent as antibacterial agents than general metal-binding compounds (e.g., EDTA, TPEN)[22] suggesting general sequestration of metal(II) cations is not the mode of action.

The 2-position of the HQ scaffold plays an important role in the antibacterial profile (e.g., spectrum of activity, potency), which is illustrated in FIG. 2A with broxyquinoline and HQ-1. Broxyquinoline is unsubstituted at the 2-position and demonstrates moderate potency of broad-spectrum antibacterial activity with MIC values of 12.5 µM (4 µg/mL) against S. epidermidis, S. aureus and A. baumannii. HQ-1 has a methyl group in the 2-position of the HQ scaffold and demonstrates a 16-fold increase in potency against the gram-positive pathogens S. aureus and S. epidermidis (MIC=0.78 µM; 0.25 µg/mL) while demonstrating an 8-fold loss in antibacterial activity against gram-negative A. baumannii (MIC=100 µM; 32 µg/mL) compared to broxyquinoline. However, there is no teaching or suggestion in the art on how to modify the 2-position of the HQ scaffold for the purpose of obtaining improved antimicrobials.

The goals were to investigate further structural modifications at the 2-position of the HQ scaffold and evaluate the new compounds for biofilm eradication against new bacterial pathogens (S. epidermidis and E. faecium). During the course of these investigations, a series of potent analogues that resulted from a reductive amination reaction between 2 and a collection of amines/anilines were discovered (FIG. 2B). 2-Quinolinecarboxyaldehyde 1 was brominated using 2.2 equivalents of N-bromosuccinimide in toluene at room temperature to afford key aldehyde 2 in 73% yield (FIG. 2B). This mild bromination reaction could be carried out on gram scale, which is critical for structural diversification during analogue synthesis. Direct oxidization of HQ-1 using selenium dioxide ($SeO_2$) in dioxane gave incomplete conversion to 2 (~50%) despite elevated temperatures (100° C.) and extended reaction times (>36 h). Interestingly, $SeO_2$ converts 2-methyl-8-hydroxyquinoline to 1 in 75% yield using moderate reaction conditions (dioxane, 80° C., 8 h), thus the bromine atoms in HQ-1 electronically suppress benzylic oxidation.

Initial attempts to carry out the key reductive amination reaction yielded no desired products despite extensive scouting (solvents: methanol, toluene, acetonitrile; temperatures: room temperature, reflux; reaction times up to two days; with or without catalytic acetic acid). Upon close examination of these reaction conditions, it was determined that initial reductive amination protocols failed due to a lack of initial imine formation. However, it was found that by using 1,2-dichloroethane as the solvent the reductive amination reaction to proceed smoothly at room temperature. Aldehyde 2 was condensed with a collection of diverse amines/anilines for 15 minutes to 1 hour, before the direct addition of sodium triacetoxyborohydride ($NaBH(OAc)_3$) provided reductive amination products HQ-2 through HQ-7 in 44-68% yield (57% average yield; FIG. 2C).

Following chemical synthesis, HQ analogues were initially evaluated in MIC assays to identify potent antibacterial agents against methicillin-resistant S. aureus (MRSA-2), methicillin-resistant S. epidermidis (MRSE, ATCC 35984) and E. faecium (ATCC 700221, VRE). Against clinical isolate MRSA-2 (Shands Hospital; Gainesville, Fla.) reductive amination HQ analogues demonstrated equipotent or slightly reduced antibacterial activities (Table 2). Against MRSE 35984, HQ-1 was found to possess potent antibacterial activities (MIC=0.39 µM) while reductive amination products HQ-3 through HQ-6 demonstrated enhanced antibacterial potencies (MIC=0.15-0.30 µM) compared to HQ-1. HQ-3 (aniline derived) and HQ-6 (4-bromoaniline derived) proved to be the most potent analogues against MRSE, demonstrating 5-fold more potent antibacterial activities than vancomycin (MIC=0.78 µM) when tested in the same assays. HQ-1 demonstrated potent antibacterial activities against VRE 700221 (MIC=2.35 µM); however, HQ-3 through HQ-6 proved to be 3- to 6-fold more potent (MIC=0.39-0.78 µM) against VRE. HQ-7 (3,5-dibromo-4-methylaniline derived), a structurally similar analogue to the highly potent HQ analogues in this series, demonstrated significantly reduced antibacterial activities (MIC=9.38-75 µM) against these drug-resistant pathogens.

Figure 3:
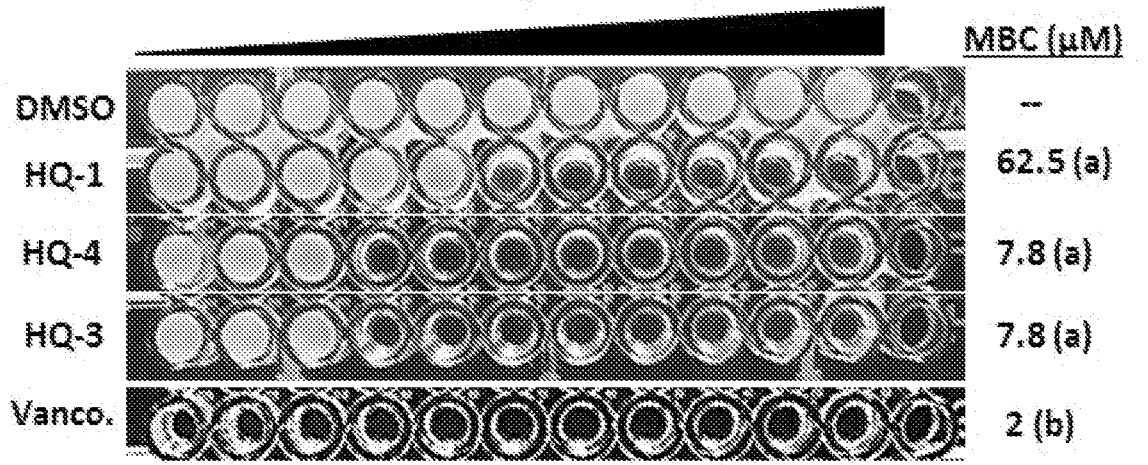
FIG. 3 shows exemplary methicillin-resistant strain of *Staphylococcus epidermidis* (MRSE) planktonic killing activities of certain compounds (top panel), and exemplary biofilm eradication activities of certain compounds (bottom panel). A Calgary Biofilm Device (CBD) was used to quantify planktonic killing activities and biofilm eradication activities in a single assay. "Vanco.": vancomycin.
Figure 3:
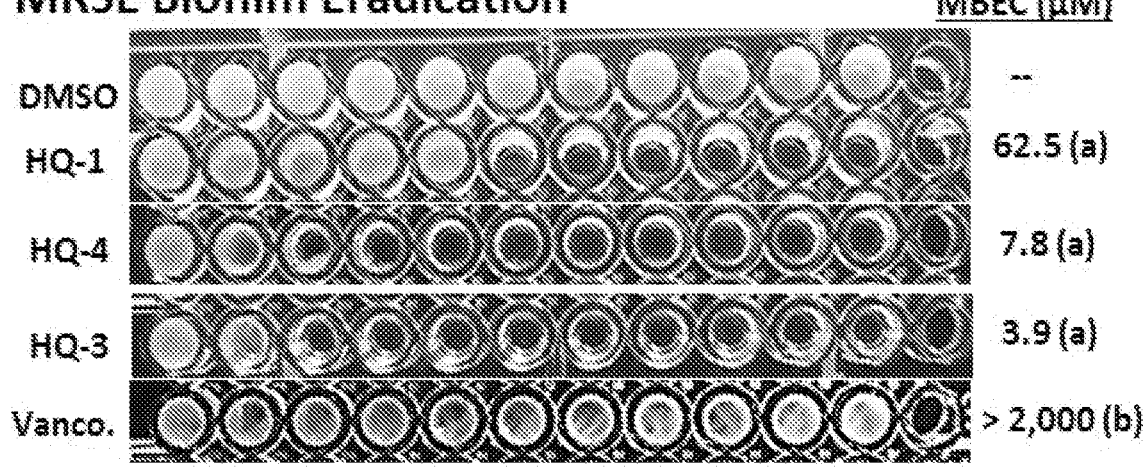

Following antibacterial studies, HQ analogues were evaluated against established bacterial biofilms using the Calgary Biofilm Device (CBD),[24] which is a useful tool for evaluating biofilm eradication activities of small molecules. This assay enables the (1) establishment, (2) compound testing and (3) recovery of viable biofilms on pegs that are attached to the lid of a 96-well plate cover and submerged in media. Following compound treatment, fresh media allows viable biofilms to grow and disperse planktonic cells into the media resulting in turbid wells after the final incubation period (FIG. 3). Eradicated biofilms are unable to recover, thus result in non-turbid microtiter wells after final incubation. The lowest concentration that results in eradicated biofilms corresponds to the MBEC value, which demonstrated ≥99.9% biofilm cell killing.

TABLE 2

Summary of antibacterial, biofilm eradication, and haemolysis activities for halogenated quinoline (HQ) analogues, relevant conventional antibiotics and controls. All concentrations are reported in µM.

| Compound | MRSA-2 MIC | Clinical Isolate MBC/MBEC | MRSE MIC | ATCC 35984 MBC/MBEC | VRE MIC | ATCC 700221 MBC/MBEC | % Haemolysis at 200 µM |
|---|---|---|---|---|---|---|---|
| HQ-1 | 0.78 | 23.5$^a$/188$^a$ | 0.39 | 31.3$^b$/93.8$^a$ | 2.35$^a$ | 2.0/1.5$^a$ | ≤1 |
| HQ-2 | 6.25 | 46.9$^a$/>1,000 | 3.13 | 9.38$^a$/62.5 | 3.13 | 15.6/3.9 | 21.3 |
| HQ-3 | 0.78 | 125/188$^a$ | 0.15$^a$ | 7.8$^b$/3.0$^a$ | 0.78 | 7.8/1.5$^a$ | 3.1 |
| HQ-4 | 1.17$^a$ | 62.5$^b$/188$^a$ | 0.30$^a$ | 9.38$^a$/5.9$^a$ | 0.78 | 1.5$^a$/1.0 | 18.8 |
| HQ-5 | 1.56 | 62.5/750$^a$ | 0.30$^a$ | 1.5$^a$/23.5$^a$ | 0.39 | 2.0$^b$/1.0 | 10.6 |
| HQ-6 | 3.13 | 125/125 | 0.15$^a$ | 5.9$^a$/31.3 | 0.78 | 3.9$^b$/1.0 | 3.7 |
| HQ-7 | 18.8$^a$ | 500/>1,000 | 9.38$^a$ | 250/>1,000 | 75$^a$ | 125/9.38$^a$ | ≤1 |
| Vancomycin | 0.59$^a$ | 3.0/>2,000 | 0.78 | 3.0$^a$/>2,000 | >100 | >200/150$^a$ | ≤1 |
| Daptomycin | 4.69$^a$ | 62.5$^b$/>2,000 | 12.5 | — | — | — | 1.7 |
| Linezolid | 3.13 | 15.6/>2,000 | 3.13 | — | 3.13 | 4.69$^a$/1.56 | ≤1 |
| QAC-10 | 3.13 | 31.3$^b$/125 | 2.35$^a$ | 31.3/31.3 | 2.35$^a$ | 3.0$^a$/3.0$^a$ | >99 |
| CCCP | 3.13 | 31.3/1,000 | 6.25 | 31.3/93.8$^a$ | — | — | 3.5 |

$^a$Midpoint value for a 2-fold range in independent experiments.
$^b$Midpoint value for a 4-fold range in independent experiments.
All MIC, MBC, and MBEC values, and haemolysis data were obtained from 2 to 6 independent experiments.

Figure 4:
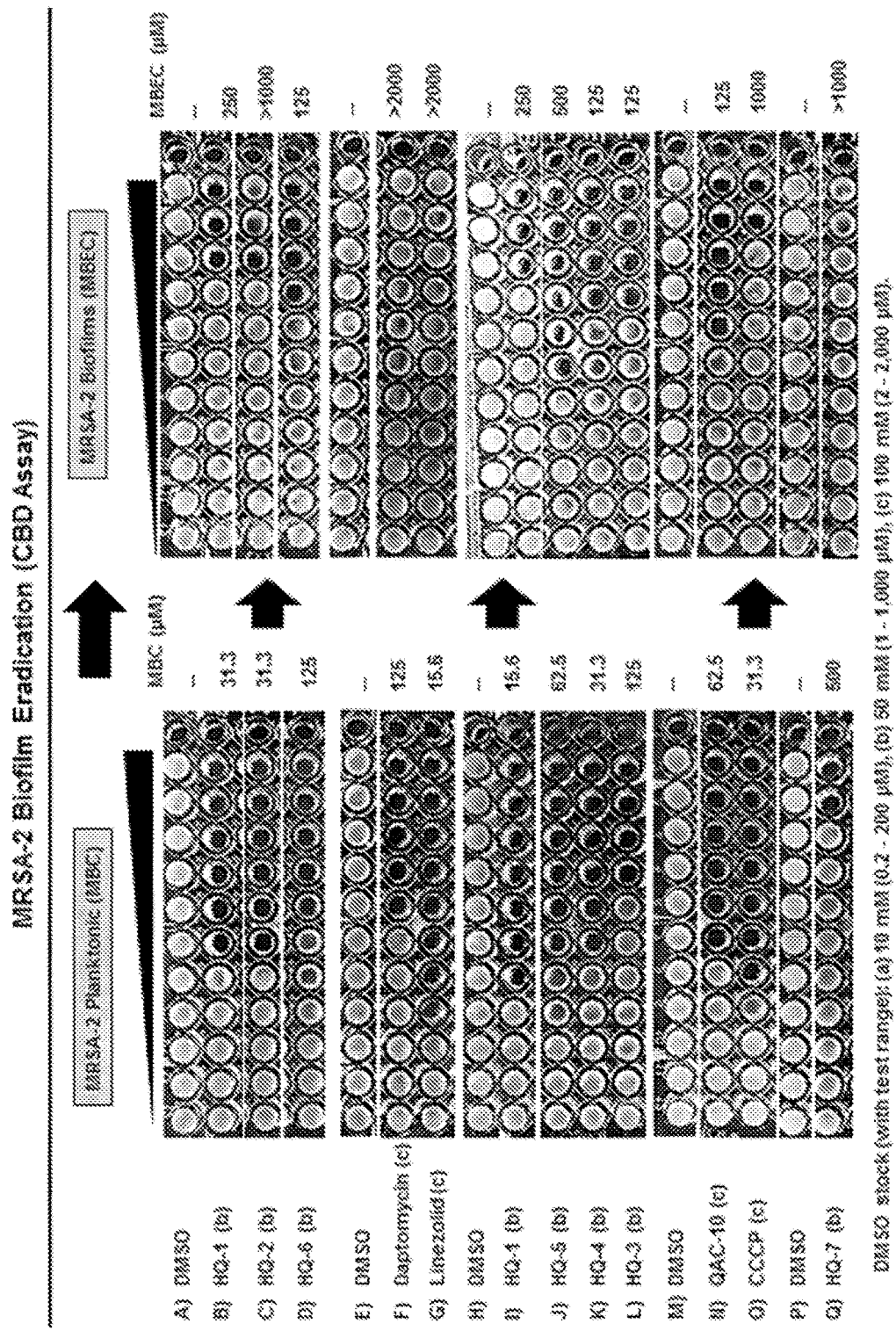
FIG. 4 shows exemplary results of methicillin-resistant strain of *Staphylococcus aureus* 2 (MRSA-2) biofilm eradication (CBD assay).
Figure 5:
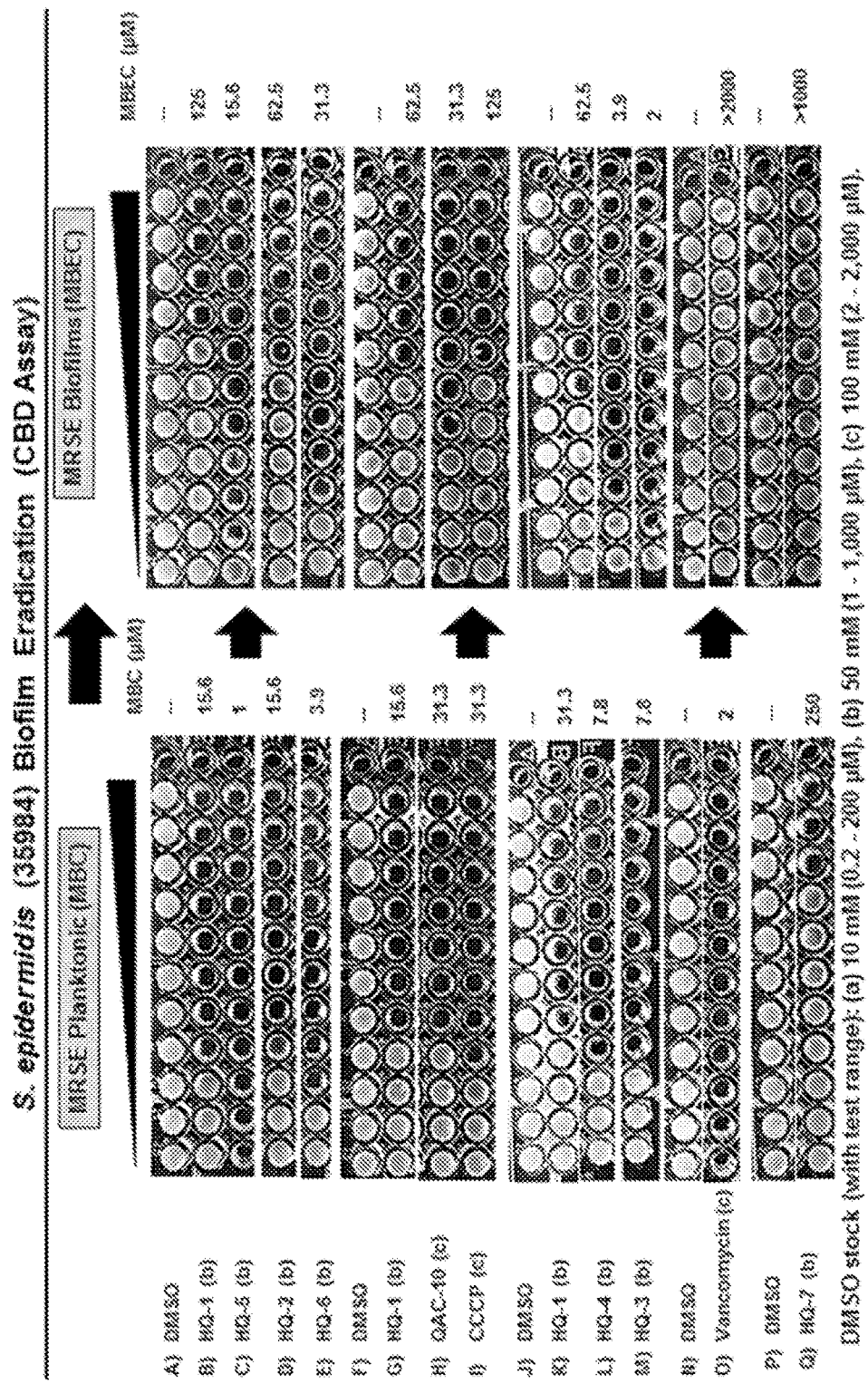
FIG. 5 shows exemplary results of *Staphylococcus epidermidis* (ATCC 35984) biofilm eradication (CBD assay).
Figure 6:
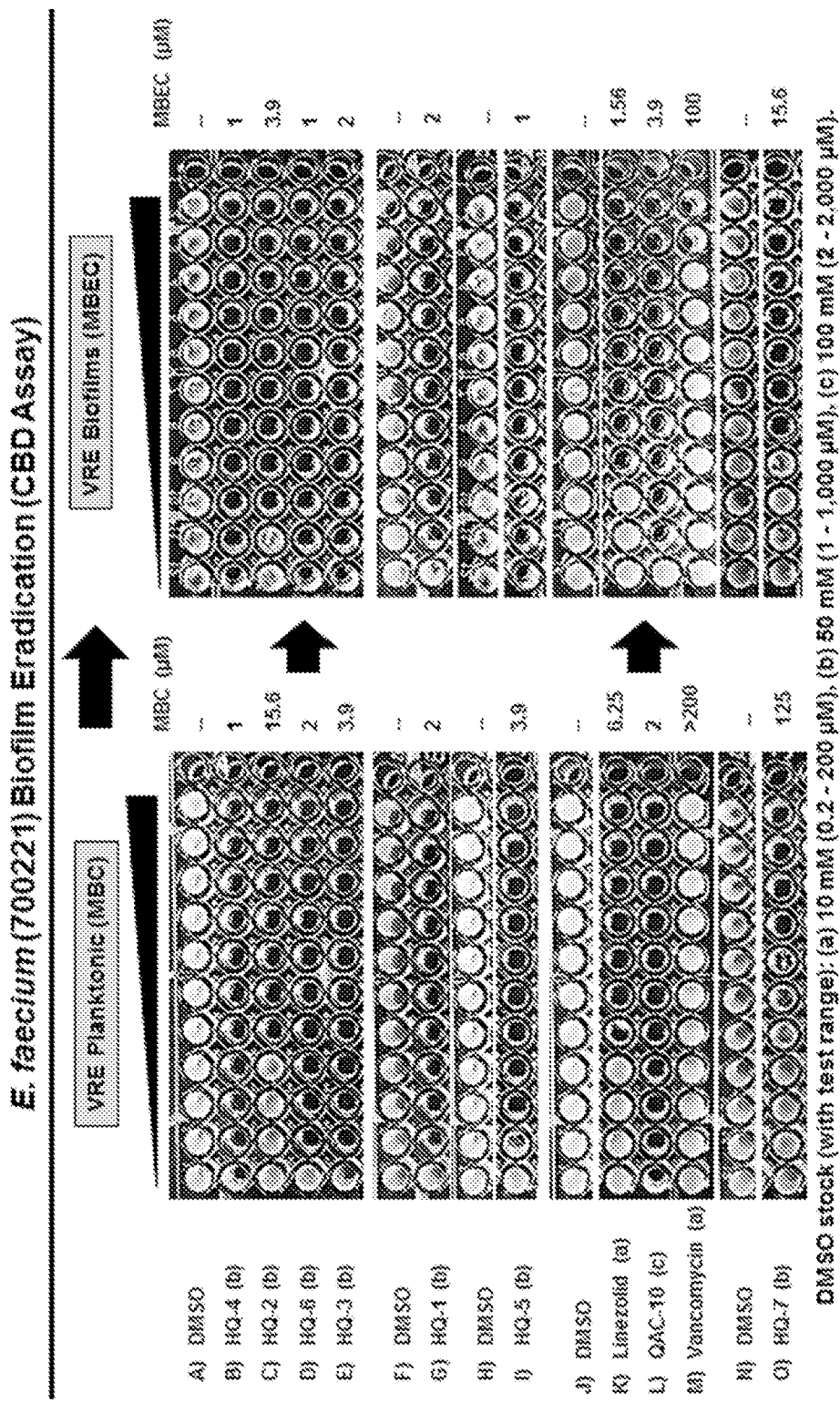
FIG. 6 shows exemplary results of *Enterococcus faecium* (ATCC 700221) biofilm eradication (CBD assay).

In addition to screening and/or evaluating biofilm-eradicating agents, the CBD was utilized to quantify planktonic killing through the determination of minimum bactericidal concentrations (MBC) of test compounds (FIGS. 4 to 6). This enables the assessment of planktonic and biofilm killing dynamics from the same experiment by assessing MBEC:MBC ratios. Ideally, biofilm-eradicating agents should demonstrate equipotent, or near equipotent, killing of both planktonic and biofilm cells (e.g., MBEC:MBC ratio of 1).

HQ analogues were evaluated against MRSA-2 in CBD assays alongside front-running MRSA treatments (vancomycin, daptomycin, linezolid). Using the CBD, HQ-1 demonstrated moderate biofilm eradication activity (MBEC=188 µM) similar to previous studies using a different assay.[22] Four of the six new reductive amination analogues demonstrated biofilm eradication activities against MRSA-2 with HQ-6 demonstrating the best potency (MBEC=125 µM) and demonstrating equipotent killing efficiencies against both planktonic and biofilm cells. Interestingly, analogues HQ-2 and HQ-7 were unable to eradicate MRSA-2 biofilms at 1,000 µM (Table 2).

Vancomycin, daptomycin, and linezolid were unable to eradicate MRSA-2 biofilms at the highest concentration (MBEC>2,000 µM) despite demonstrating moderate to excellent planktonic killing (MBC=3.0-62.5 µM; Table 2). The MBEC:MBC ratios for vancomycin, daptomycin, and linezolid ranged between >32 and >667. The inability of these leading antibiotics to eradicate biofilms at up to 667-times the concentration required to kill corresponding planktonic MRSA-2 (e.g., vancomycin) are illustrative of the antibiotic-tolerant nature of bacterial biofilms that leads to significant problems in treating biofilm-associated bacterial infections.

Figure 10:
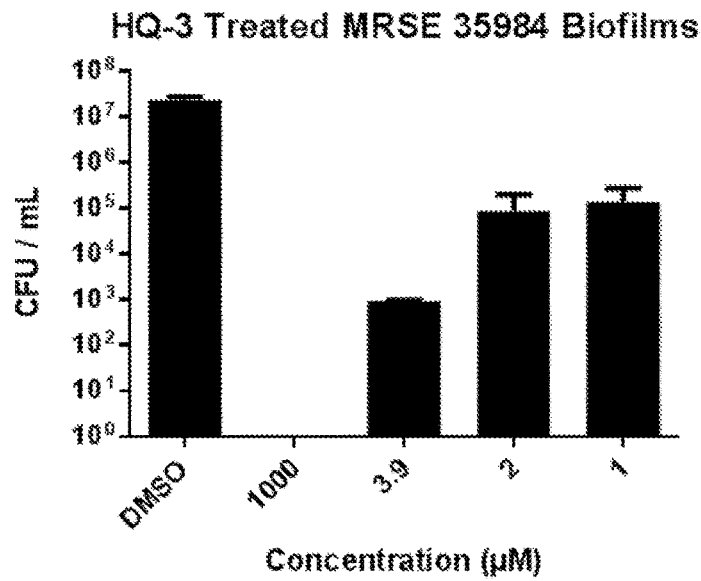
FIG. 10 shows the exemplary methicillin-resistant strain of *Staphylococcus epidermidis* (MRSE, ATCC 35984) biofilm eradication activity of HQ-3.

HQ analogues were also evaluated alongside vancomycin in CBD assays against MRSE 35984 (Table 2). HQ-1 demonstrated good MRSE biofilm eradication activities with an MBEC value of 93.8 µM, which was 3-fold higher than planktonic killing in this assay (MBC=31.3 µM). All reductive amination HQ compounds, except HQ-7, demonstrated enhanced biofilm eradication activities (MBEC=3.0-62.5 µM; Table 2) against MRSE biofilms compared to parent HQ-1. HQ-3 (MBEC=3.0 µM, FIG. 10) and HQ-4 (MBEC=5.9 µM) proved to be the most potent MRSE biofilm eradicators in this series (FIG. 3) while demonstrating equipotent planktonic and biofilm killing in these experiments (MBEC:MBC ratio ~1). Similar to the MRSA-2 results, Vancomycin demonstrated potent bactericidal activities against planktonic MRSE (MBC=3.0 µM) using the CBD, yet was unable to eradicate MRSE biofilms (MBEC>2,000 µM; FIG. 3).

Following the investigations with staphylococcal pathogens, the attention was turned to VRE biofilms. The panel of HQs analogues evaluated were found to be highly potent against VRE (ATCC 700221) biofilms. HQ-1 and HQ-3 through HQ-6 demonstrated potent biofilm eradication activities against VRE biofilms (MBEC=1.0-1.5 µM, Table 1). Interestingly, in the CBD assays with VRE 700221, these biofilms were found to be more sensitive than the corresponding planktonic cells against all compounds that were evaluated. The most potent HQ analogues (HQ-4 through HQ-6) were equipotent to linezolid, which is used to treat VRE infections.

In addition to the new HQ analogues and select antibiotics, the known biofilm eradicators QAC-10 (AMP mimic, membrane disruptor)[21] and carbonyl cyanide m-chlorophenyl hydrazone (CCCP; proton ionophore)[25] were tested as positive controls. Both controls demonstrated positive biofilm eradication in CBD assays with QAC-10 being the more potent control. When comparing the biofilm eradication activities of these HQ analogues to QAC-10, HQ analogues demonstrated equipotent biofilm eradication against MRSA-2 and enhanced biofilm eradication potencies against MRSE and VRE biofilms (Table 2).

HQ analogues, conventional antibiotics and positive controls were subjected to haemolysis assays (Table 2). These assays provide important mechanistic information, especially since successful biofilm-eradicating agents typically destroy bacterial membranes. All compounds were screened against human red blood cells (RBCs) at 200 µM. Despite HQ-2, HQ-4 and HQ-5 exhibiting 10.6-21.3% haemolytic activity, HQ-3 and HQ-6 demonstrated minimal haemolysis (<4%) at 200 µM, which is a relatively high concentration compared to the corresponding MIC and MBEC values against MRSE, MRSA and VRE for these analogues. Membrane-targeting biofilm eradicator, QAC-10, gave >99% haemolysis at 200 µM during these investigations. Due to the drastic differences in haemolytic activities between HQ analogues and QAC-10,[21] it was likely that HQ analogues do not eradicate biofilms through the destruction of bacterial membranes.

During these investigations, iron(II) was found to decrease the antibacterial activity of HQ-3 and HQ-6 against S. aureus; however, this effect is more pronounced in HQ-1. Co-treatment of copper(II) or magnesium(II) with HQ-3 and HQ-6 led to insignificant changes in antibacterial activities. Although detailed mechanistic investigations are required, it was likely that HQs operate through an iron(II)-dependent mode of action possibly through the targeting of a metalloprotein critical to bacterial biofilm viability.

Additional analogs were screened in the biofilm eradication assays discussed above, the data for which is presented in Table 3. Similar to the results presented in Table 2, HQ-1 demonstrated good biofilm eradication activities against MRSA-2 reporting an MBEC value of 188 µM using CBD assays. A-HQ-3 (MBEC=93.8 µM), RA-HQ-8 (MBEC=125 µM), RA-HQ-12 (MBEC=93.8 µM) and RA-HQ-13 (MBEC=93.8 µM) reported improved biofilm eradication activities against MRSA-2 compared to HQ-1. MBEC:MBC ratios of between 1 and 3 against MRSA-2 were observed for lead biofilm-eradicating HQs, demonstrating near equipotent biofilm and planktonic killing efficiencies. A-HQ-4, RA-HQ-5, and RA-HQ-7 demonstrated equipotent biofilm eradication activities against MRSA-2 compared to HQ-1. Surprisingly, the 2-ethyl analogue A-HQ-1 proved to have less potent biofilm eradication activity against MRSA-2, despite the 2-methyl (HQ-1) and 2-propyl (A-HQ-3) analogues demonstrating potent activities. A-HQ-1 possesses potent antibacterial activities against MRSA (and MRSE; Table 3) without similar biofilm eradication activities, which is a phenotype rarely encountered with HQ small molecules against staphylococcal pathogens. In addition to A-HQ-1, a similar activity trend was observed for A-HQ-7.

Also, as shown in Table 2, vancomycin, daptomycin and linezolid were unable to eradicate MRSA-2 biofilms at the highest test concentration (MBEC>2000 µM) despite reporting moderate to excellent planktonic killing (MBC=3.0-62.5 µM) in the same experiment. These large planktonic versus biofilm killing activities (MBEC:MBC ratio for vancomycin is >667 against MRSA-2) is illustrative of the high levels of tolerance that biofilms display towards conventional antibiotics. Against MRSA-2, lead HQ analogues are >20-fold more potent as biofilm-eradicating agents when compared to current anti-MRSA therapeutic agents (Table 3). Other reported biofilm-eradicating agents and persister cell killers (i.e., QAC-10[21a], CCCP[25,26], NAC[27], pyrazinamide[28,29]; Table 3) were also evaluated as positive controls. QAC-10, an antimicrobial peptide mimic and membrane-lysing agent, proved to be the most potent control in this panel; however, lead HQs were found to be more potent than QAC-10 against MRSA, MRSE and VRE biofilms (Table 3).

TABLE 3

Exemplary antibacterial, biofilm eradication, and haemolysis activities for select halogenated quinoline (HQ) analogues, relevant conventional antibiotics, and controls. All concentrations are reported in µM.

| Compound | MRSA-2 MIC | MRSA-2 MBC/ MBEC | MRSE MIC | MRSE MBC/ MBEC | VRE MIC | VRE MBC/ MBEC | % Haemolysis at 200 µM |
|---|---|---|---|---|---|---|---|
| HQ-1 | 0.78 | 23.5$^a$/188$^a$ | 0.30$^a$ | 31.3$^b$/93.8$^a$ | 2.35$^a$ | 2.0/1.5$^a$ | ≤1 |
| A-HQ-1 | 0.78 | 93.8$^a$/1,000 | 0.39 | 31.3/>1,000 | 0.78 | 1.5$^a$/2.0 | ≤1 |
| A-HQ-3 | 0.78 | 125/93.8$^a$ | 0.59$^a$ | 9.38$^a$/62.5 | 0.78 | 2.0$^b$/2.0$^b$ | ≤1 |
| A-HQ-4 | 1.56 | 188$^a$/188$^a$ | 1.17$^a$ | 125/125 | 0.39 | 7.8/7.8 | ≤1 |
| A-HQ-5 | 0.78 | — | — | — | 100 | — | 12.3 |
| A-HQ-7 | 9.38$^a$ | 375$^a$/>1,000 | 1.17$^a$ | 250/>1,000 | 2.35$^a$ | 9.38$^a$/1.5$^a$ | ≤1 |
| RA-HQ-2 | 2.35$^a$ | 31.3$^a$/93.8 | 1.56 | 23.5$^a$/62.5 | 3.13 | 15.6$^b$/7.8 | 87.9 |
| RA-HQ-12 | 0.39 | 31.3$^b$/93.8$^a$ | 0.39 | 3.9/5.9$^a$ | 0.78 | 1.0$^c$/1.0$^c$ | ≤1 |
| RA-HQ-13 | 0.78 | 31.3/93.8$^a$ | 0.30$^a$ | 31.3/46.9$^a$ | 0.78 | 1.5$^a$/1.5$^a$ | 17.6 |
| RA-HQ-14 | 4.69$^a$ | 250/750$^a$ | 0.78 | 46.9$^a$/188 | 4.69$^a$ | 46.9$^a$/1.5$^a$ | 11.0 |
| RA-HQ-15 | 1.56 | 188$^a$/750$^a$ | 0.20 | 31.3$^b$/93.8$^a$ | 0.78 | 7.8$^b$/23.5$^a$ | 37.3 |
| RA-HQ-16 | 1.56 | 188$^a$/500 | 0.20 | 46.9$^a$/125 | 0.78 | 7.8$^b$/1.5$^a$ | ≤1 |
| RA-HQ-17 | 3.13 | 750$^a$/>1,000 | 0.59$^a$ | 188$^a$/>1,000 | 1.56 | 31.3$^b$/3.0$^a$ | 7.4 |
| RA-HQ-22 | >100 | >1,000/>1,000 | 4.69$^a$ | 250/375$^a$ | 9.38$^a$ | 31.3$^b$/7.8 | 3.0 |
| RA-HQ-23 | 25 | >1,000/>1,000 | 12.5 | 125/375$^a$ | 25 | 31.3$^b$/15.6 | 3.3 |
| Vancomycin | 0.59$^a$ | 3.0/>2,000 | 0.78 | 3.0$^a$/>2,000 | >100 | >200/150$^a$ | ≤1 |
| Daptomycin | 4.69$^a$ | 62.5$^b$/>2,000 | 12.5 | — | — | — | 1.7 |
| Linezolid | 3.13 | 15.6/>2,000 | 3.13 | — | 3.13 | 4.69$^a$/1.56 | ≤1 |
| QAC-10 | 3.13 | 31.3$^b$/125 | 2.35$^a$ | 31.3/31.3 | 2.35$^a$ | 3.0$^a$/3.0$^a$ | >99 |
| CCCP | 3.13 | 31.3/1,000 | 6.25 | 31.3/93.8$^a$ | — | — | 3.5 |
| NAC | — | >2,000/>2,000 | — | >2,000/>2,000 | — | >2,000/>2,000 | — |
| Pyrazinamide | — | >2,000/>2,000 | — | — | — | — | ≤1 |
| EDTA | — | 2,000/>2,000 | — | 1,000/>2,000 | — | — | 3.0 |

Notes:
$^a$Midpoint value for a 2-fold range in independent experiments.
$^b$Midpoint value for a 4-fold range in independent experiments.
$^c$Lowest concentration tested. All MIC, MBC, MBEC values and haemolysis data was obtained from at least three independent experiments.
MRSA refers to methicillin-resistant *Staphylococcus aureus*,
MRSE refers to methicillin-resistant *Staphylococcus epidermidis*,
VRE refers to vancomycin-resistant *Enterococcus faecium*.

Also, a small panel of active HQ analogues were screened against a second MRSA strain, ATCC BAA-1707, in CBD assays. This multi-drug resistant MRSA strain was found to be more sensitive to HQ compounds than MRSA-2, which is a clinical isolate from a patient at Shands Hospital (Gainesville, Fla.). Impressively, RA-HQ-12 reported an MBEC value of 7.8 µM (Table 4 and FIG. 11A), which proved to be 6-fold more potent than HQ-1 against MRSA BAA-1707. Similar to MRSA-2, vancomycin, daptomycin and linezolid all were unable to eradicate MRSA BAA-1707 biofilms despite demonstrating moderate to potent planktonic killing activity in CBD assays (Table 4).

TABLE 4

Summary of MRSA BAA-1707 antibacterial and biofilm eradication, and haemolysis activities for halogenated quinoline (HQ) analogues, relevant conventional antibiotics and controls. All concentrations are reported in µM.

| Compound | MRSA BAA-1707 MBC/MBEC |
|---|---|
| HQ-1 | 62.5/46.9$^a$ |
| A-HQ-3 | 31.3/46.9$^a$ |
| A-HQ-5 | 31.3/23.5$^a$ |
| RA-HQ-5 | 62.5$^b$/93.8$^a$ |
| RA-HQ-12 | 15.6$^b$/7.8 |
| RA-HQ-16 | 93.8$^a$/375$^a$ |
| Vancomycin | 5.9$^a$/>2,000 |
| Daptomycin | 125/>2,000 |
| Linezolid | 31.3/>2,000 |

Figure 11A:
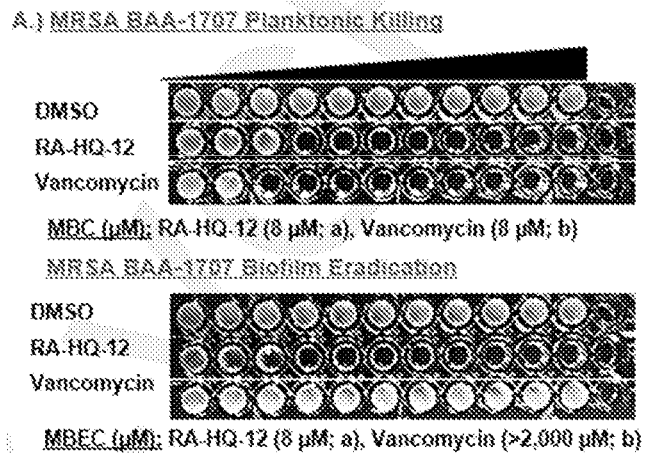
FIG. 11A shows exemplary results of methicillin-resistant strain of *Staphylococcus aureus* (BAA-1707) planktonic killing and biofilm eradication (CBD assay).
Figure 11B:
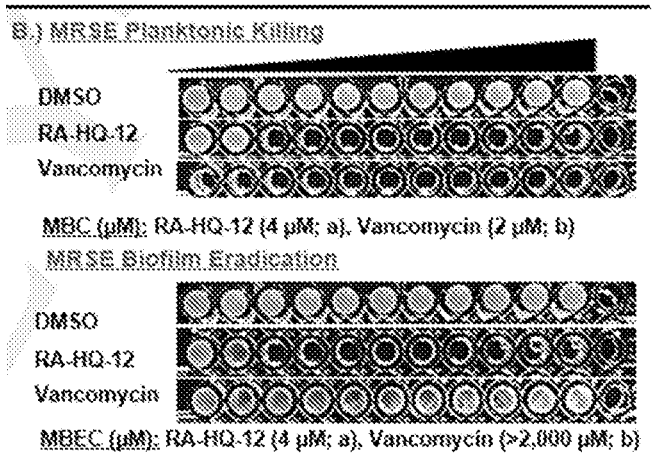
FIG. 11B shows exemplary results of methicillin-resistant *S. epidermidis* (MRSE) planktonic killing and biofilm eradication (CBD assay).
Figure 11C:
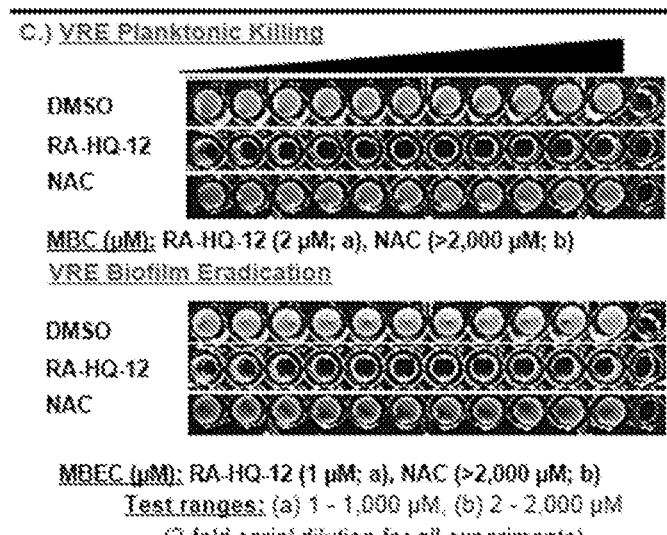
FIG. 11C shows exemplary results of vancomycin-resistant *Enterococcus faecium* (VRE) planktonic killing and biofilm eradication (CBD assay).

MRSE biofilms demonstrated an increased sensitivity to HQs (compared to MRSA-2 results) as nine additional HQ compounds showed improved biofilm eradication activities compared to HQ-1 (MBEC=93.8 µM; Table 3) with RA-HQ-5 (MBEC=3.0 µM), RA-HQ-7 (MBEC=5.9 µM) and RA-HQ-12 (MBEC=5.9 µM; FIG. 11) proving to be the most potent analogues (MBEC:MBC ratios ~1 for these analogues). In addition, RA-HQ-9 (MBEC=23.5 µM), RA-HQ-8 (MBEC=31.3 µM) and RA-HQ-13 (MBEC=46.9 µM) demonstrated excellent eradication activities against MRSE biofilms. Ten HQs demonstrated equipotent or reduced biofilm eradication activities against MRSE (MBEC=125 to >1,000 µM) compared to HQ-1. In contrast. vancomycin was unable to eradicate MRSE biofilms (MBEC>2,000 µM), despite effectively killing planktonic cells (MBC=3.0 µM) in CBD assays (FIGS. 11A and 11B).

Figure 12:
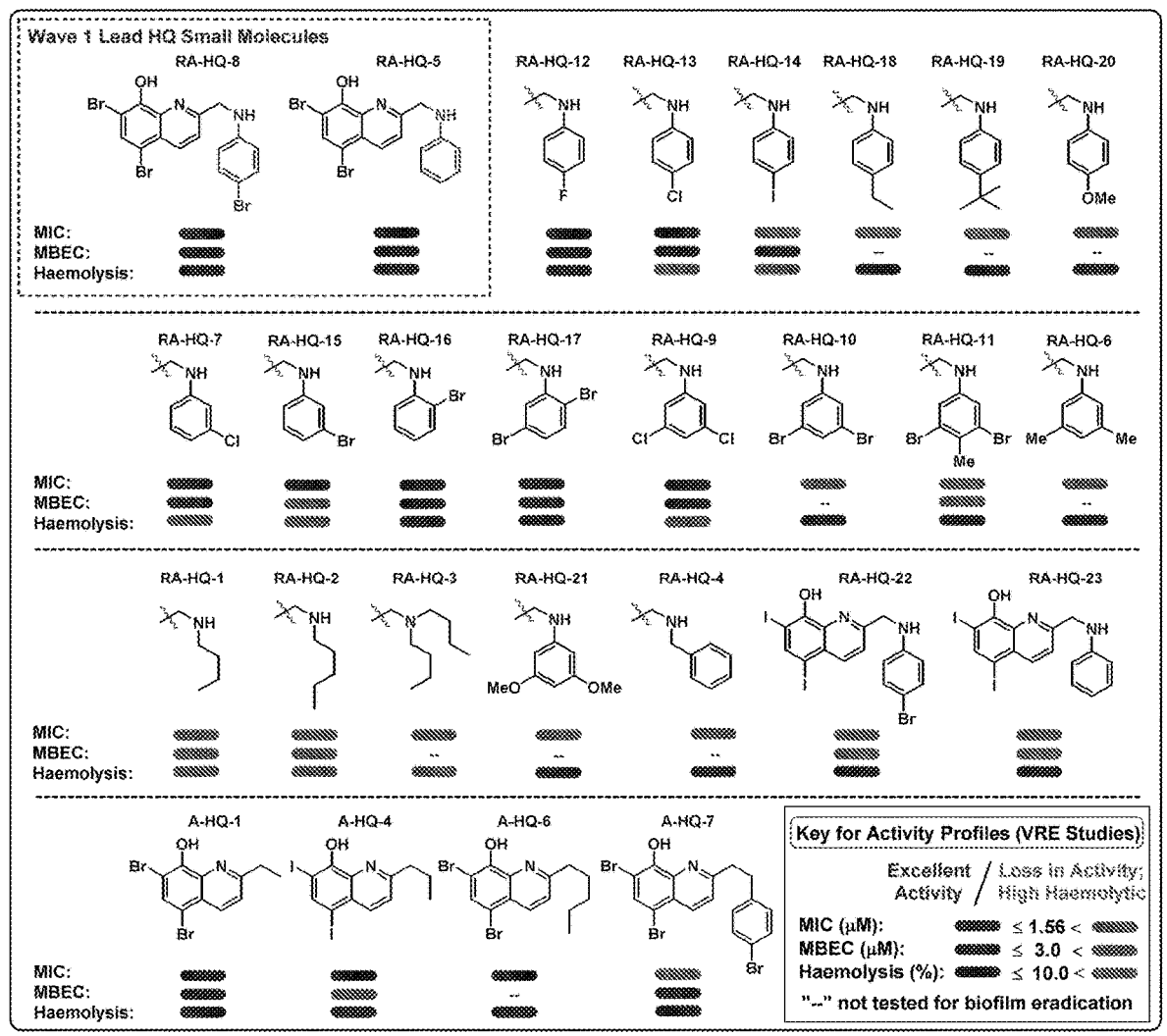
FIG. 12 shows the structure activity relationship (SAR) of various HQ analogues against vancomycin-resistant *Enterococcus faecium* (VRE).
Figure 13:
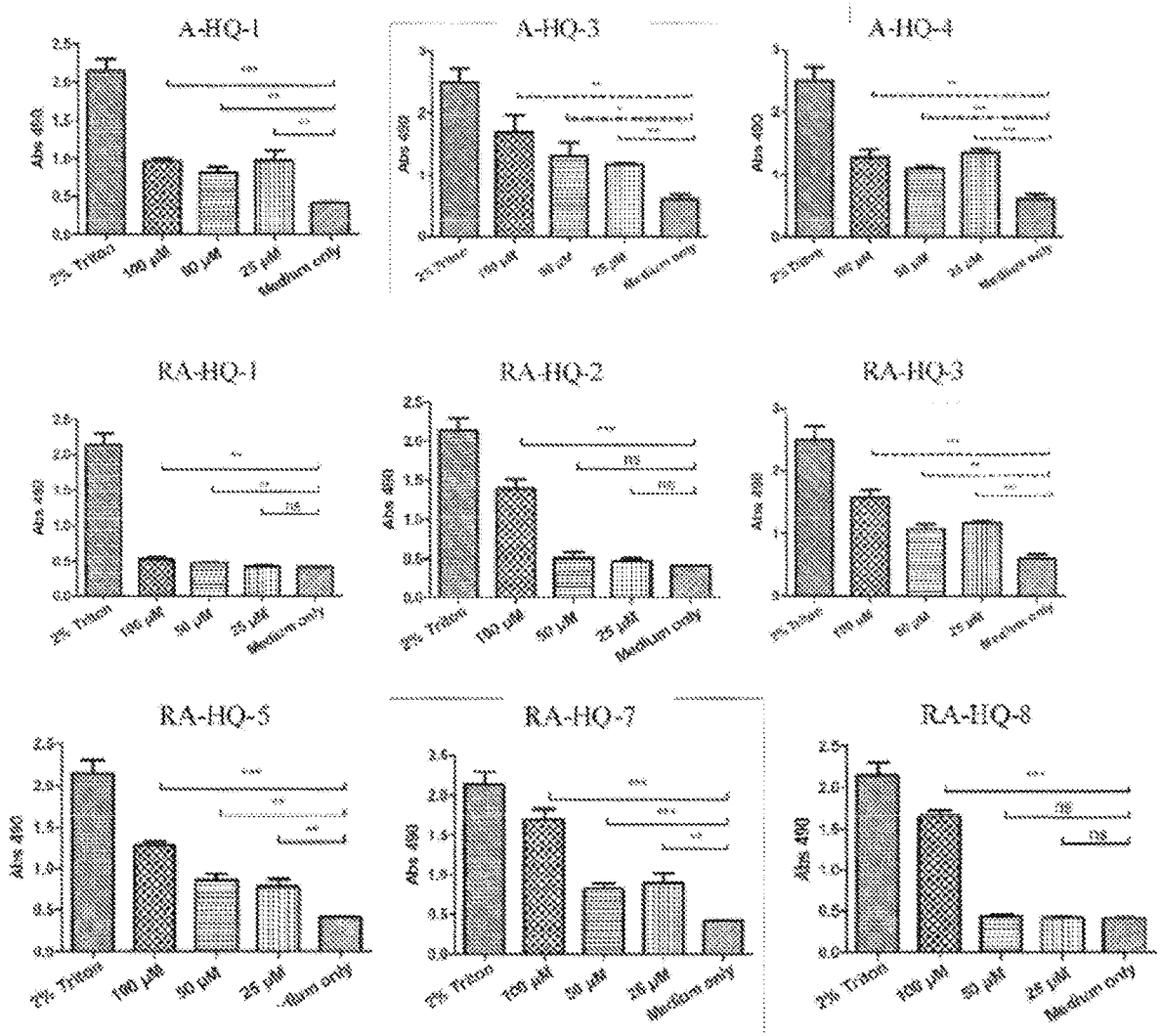
FIG. 13 shows HeLa cytotoxicity results for select HQ compounds.

Against VRE biofilms, 13 new HQ analogues were found to be highly potent biofilm-eradicating agents (MBEC=1.0-3.9 µM, Table 1) while demonstrating equipotent planktonic and biofilm cell killing by comparing MBC:MBEC ratios. Four analogues eradicated VRE biofilms at 1 µM (i.e., RA-HQ-7, RA-HQ-8, RA-HQ-9, RA-HQ-12), which was the lowest concentration tested. Interestingly, N-acetyl cystine (NAC) was unable to eradicate VRE biofilms at the highest test concentration (MBEC>2,000 µM) (FIG. 11) despite a previous report that NAC eradicates *E. faecium* biofilms.[27] Linezolid registered an MBEC value of 1.56 µM against VRE 700221 biofilms while QAC-10 (positive-control) registered an MBEC value of 3.0 µM. The MIC, MBEC, and haemolysis data for the HQ compounds against VRE are summarized in FIG. 12. Select HQs were evaluated against HeLa cells (lactate dehydrogenase release assays) and demonstrated good to excellent mammalian cyctotoxicity (IC$_{50}$>50 to >100 µM; FIG. 13).

In conclusion, a new series of reductive amination-derived HQ analogues that demonstrate potent eradication activities against MRSA, MRSE and VRE biofilms have been discovered. When tested alongside these HQ analogues, several front-running MRSA treatments (vancomycin, daptomycin, linezolid) were ineffective at eradicating MRSA-2 biofilms at very high concentrations (2 mM) despite demonstrating moderate to excellent bactericidal activities against MRSA-2 planktonic cells. Also, it has been concluded it is likely that these HQ analogues do not operate primarily through membrane destruction, but rather an iron (II)-dependent mechanism. This reductive amination route to synthesize highly potent HQ analogues will allow for further optimization of biofilm eradication activities. HQ-based biofilm eradicators are a promising class of antibacterial agents that could be useful in the treatment of persistent, biofilm-associated bacterial infections.

REFERENCES

1. R. M. Donlan and J. W. Costerton, *Clin. Microbiol. Rev.*, 2002, 15, 167-193.
2. D. Davies, *Nat. Rev. Drug Discov.*, 2003, 2, 114-122.
3. N. K. Archer, M. J. Mazaitis, J. W. Costerton, J. G. Leid, M. E. Powers and M. E. Shirtliff, *Virulence*, 2011 2, 445-459.
4. N. Rabin, Y. Zheng, C. Opoku-Temeng, Y. Du, E. Bonsu and H. O. Sintim, *Future Med. Chem.*, 2015, 7, 647-671.
5. D. J. Musk and P. J. Hergenrother, *Curr. Med. Chem.*, 2006, 13, 2163-2177.
6. K. Lewis, *Nat. Rev. Microbiol.*, 2007, 5, 48-56.
7. K. Lewis, *Annu. Rev. Microbiol.*, 2010, 64, 357-372.
8. R. M. Klevens, J. R. Edwards, C. L. Richards, T. C. Horan, R. P. Gaynes, D. A. Pollock and D. M. Cardo, *Public Health Rep.*, 2007, 122, 160-166.
9. M. Otto, *Curr. Top. Microbiol. Immunol.*, 2008, 322, 207-228.
10. J. N. Snowden, M. Beaver, M. S. Smeltzer and T. Kielian, *Infect. Immun.*, 2012, 80, 3206-3214.
11. C. E. Heim, M. L. Hanke and T. Kielian, *Methods Mol. Biol.*, 2014, 1106, 183-191.
12. S. Almohamad, S. R. Somarajan, K. V. Singh, S. R. Nallapareddy and B. E. Murray, *FEMS Microbiol. Lett.*, 2014, 353, 151-156.
13. G. D. Geske, R. J. Wezeman, A. P. Seigel and H. E. Blackwell, *J. Am. Chem. Soc.*, 2005, 127, 12762-12763.
14. M. B. Miller and B. L. Bassler, *Annu. Rev. Microbiol.*, 2001, 55, 165-199.
15. R. J. Worthington, J. J. Richards and C. Melander, *Org. Biomol. Chem.*, 2012, 10, 7457-7474.
16. M. H. Fletcher, M. C. Jennings and W. M. Wuest, *Tetrahedron*, 2014, 70, 6373-6383.
17. T. Garrison, F. Bai, Y. Abouelhassan, N. G. Paciaroni, S. Jin and R. W. Huigens III, *RSC Adv.*, 2015, 5, 1120-1124.
18. G. H. De Zoysa, A. J. Cameron, V. V. Hegde, S. Raghothama and V. Sarojini, *J. Med. Chem.*, 2015, 58, 625-639.
19. J. Hoque, M. M. Konai, S. Gonuguntla, G. B. Manjunath, S. Samaddar, V. Yarlagadda and J. Haldar, *J. Med. Chem.*, 2015, 58, 5486-5500.
20. H. Hirt and S. U. Gorr, *Antimicrob. Agents Chemother.*, 2013, 57, 4903-4910.
21. (a) M. C. Jennings, L. E. Ator, T. J. Paniak, K. P. C. Minbiole and W. M. Wuest, *ChemBioChem*, 2014, 15, 2211-2215.; (b) M. A. Mitchell, A. A. Iannetta, M. C. Jennings, M. H. Fletcher, W. M. Wuest and K. P. C. Minbiole, *Chem Bio Chem*, 2015, published online Sep. 11, 2015, DOI: 10.1002/cbic.201500381.
22. Y. Abouelhassan, A. T. Garrison, F. Bai, V. M. Norwood IV, M. T. Nguyen, S. Jin and R. W. Huigens III, *Chem Med Chem*, 2015, 10, 1157-1162.
23. H. Gershon and R. Parmegiani, *Appl. Microbiol.*, 1963, 11, 62-65.
24. H. Ceri, M. E. Olson, C. Stremick, R. R. Read, D. Morck and A. Buret, *J. Clin. Microbiol.* 1999, 37, 1771-1776.
25. Y. Eun, M. H. Foss, D. Kiekebusch, D. A. Pauw, W. M. Westler, M. Thanbichler and D. B. Weibel, *J. Am. Chem. Soc.* 2012, 134, 11322-11325.
26. A. T. Garrison, Y. Abouelhassan, D. Kallifidas, F. Bai, M. Ukhanova, V. Mai, S. Jin, H. Luesch, R. W. Huigens III, *Angew. Chem., Int. Ed.*, 2015, 54, 14819-14823.
27. S. Y. Quah, S. Wu, J. N. Lui, C. P. Sum, K. S. Tan, *J. Endod.* 2012, 38, 81-85.
28. T. K. Wood, *Biotechnol. Bioeng.* 2016, 113, 476-483.
29. Y. Zhang, D. Mithison, *Int. J. Tuberc. Lung Dis.* 2003, 7, 6-21.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of the formula:

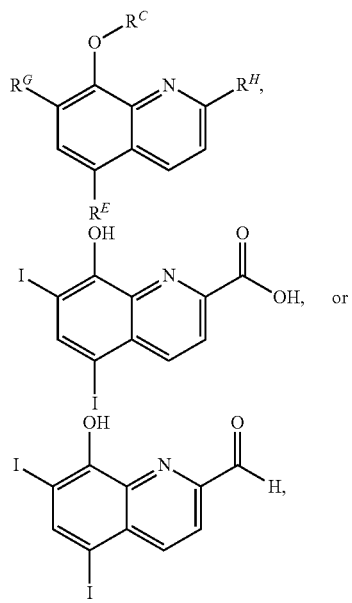
(I')

or a pharmaceutically acceptable salt thereof, wherein:
$R^H$ is:
  $CO_2R^L$, wherein $R^L$ is substituted or unsubstituted, $C_{1-6}$ alkyl or an oxygen protecting group;
  (substituted or unsubstituted $C_{1-6}$-alkylene)-OH;
  CN;
  $NR^M_2$;

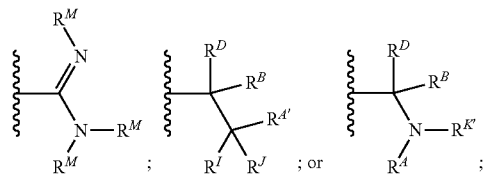

$R^{A'}$ is substituted methyl, substituted or unsubstituted $C_{2-6}$ alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted, monocyclic heteroaryl, or unsubstituted bicyclic heteroaryl;

$R^A$ is substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^B$ is H, halogen, or substituted or unsubstituted $C_{1-6}$ alkyl;

$R^D$ is H, halogen, or substituted or unsubstituted $C_{1-6}$ alkyl;

$R^I$ is H, halogen, or substituted or unsubstituted $C_{1-6}$ alkyl;

$R^J$ is H, halogen, or substituted or unsubstituted $C_{1-6}$ alkyl;

$R^{K'}$ is H, substituted or unsubstituted $C_{1-6}$ alkyl, or a nitrogen protecting group;

$R^K$ is substituted or unsubstituted $C_{1-6}$ alkyl or a nitrogen protecting group;

each $R^M$ is independently H, substituted or unsubstituted $C_{1-6}$ alkyl, or a nitrogen protecting group;

$R^C$ is H or $CH_3$;

$R^E$ is halogen; and $R^G$ is halogen;

provided that at least one of $R^E$ and $R^G$ is Br or I.

2. The compound of claim 1, wherein the compound is of the formula:

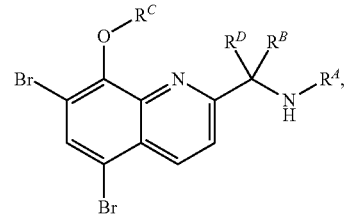

or a pharmaceutically acceptable salt thereof.

3. The compound of claim 1, wherein the compound is of the formula:

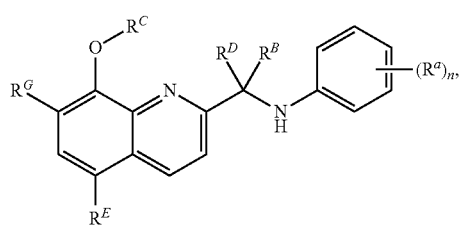

or a pharmaceutically acceptable salt thereof, wherein:
  each instance of $R^a$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^1$, $-N(R^1)_2$, $-SR^1$, $-CN$, $-SCN$, $-C(=NR^1)R^1$, $-C(=NR^1)OR^1$, $-C(=NR^1)N(R^1)_2$, $-C(=O)R^1$, $-C(=O)OR^1$, $-C(=O)N(R^1)_2$, $-NO_2$, $-NR^1C(=O)R^1$, $-NR^1C(=O)OR^1$, $-NR^1C(=O)N(R^1)_2$, $-OC(=O)R^1$, $-OC(=O)OR^1$, or $-OC(=O)N$ ($R^1$)$_2$, wherein each instance of $R^1$ is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^1$ are joined to form a substituted or unsubstituted heterocyclic or substituted or unsubstituted heteroaryl ring; and n is 0, 1, 2, 3, 4, or 5.

4. The compound of claim 3, wherein the compound is of the formula:

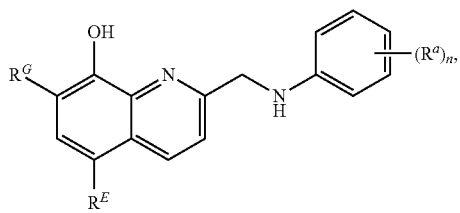

or a pharmaceutically acceptable salt thereof.

5. The compound of claim 3, wherein the compound is of the formula:

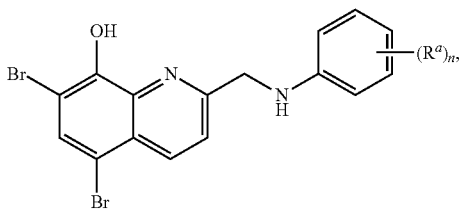

or a pharmaceutically acceptable salt thereof.

6. The compound of claim 1, or a pharmaceutically acceptable salt thereof, wherein $R^A$ is of the formula:

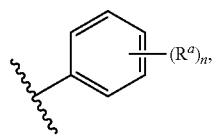

wherein:
each instance of Ra is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^1$, —N(R$^1$)$_2$, —SR$^1$, —CN, —SCN, —C(=NR$^1$)R$^1$, —C(=NR$^1$)OR$^1$, —C(=NR$^1$)N(R$^1$)$_2$, —C(=O)R$^1$, —C(=O)OR$^1$, —C(=O)N(R$^1$)$_2$, —NO$_2$, —NR$^1$C(=O)R$^1$, —NR$^1$C(=O)OR$^1$, —NR$^1$C(=O)N(R$^1$)$_2$, —OC(=O)R$^1$, —OC(=O)OR$^1$, or —OC(=O)N(R$^1$)$_2$, wherein each instance of R$^1$ is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^1$ are joined to form a substituted or unsubstituted heterocyclic or substituted or unsubstituted heteroaryl ring; and n is 1, 2, 3, 4, or 5.

7. The compound of claim 1, wherein the compound is of Formula (I'-a):

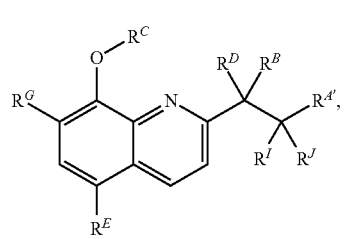

or a pharmaceutically acceptable salt thereof.

8. The compound of claim 1, or a pharmaceutically acceptable salt thereof, wherein $R^{A'}$ is substituted methyl, substituted or unsubstituted $C_{2-6}$ alkyl, or substituted or unsubstituted aryl.

9. The compound of claim 7, wherein the compound is of the formula:

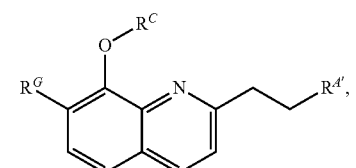

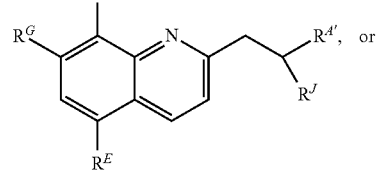

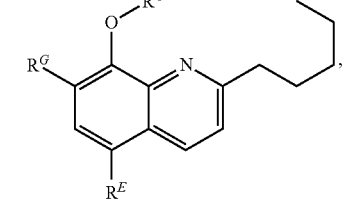

or a pharmaceutically acceptable salt thereof.

10. The compound of claim 1, or a pharmaceutically acceptable salt thereof, wherein $R^C$ is H.

11. The compound of claim 1, or a pharmaceutically acceptable salt thereof, wherein $R^E$ is Br or I.

12. The compound of claim 1, or a pharmaceutically acceptable salt thereof, wherein $R^G$ is Br or I.
13. The compound of claim 1, wherein the compound is of the formula:
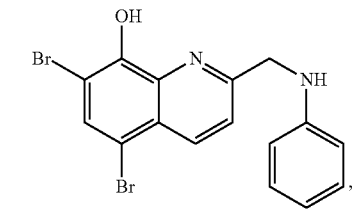
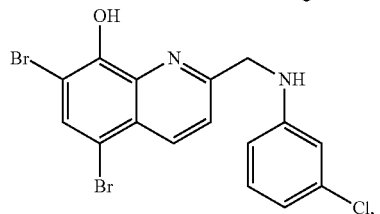
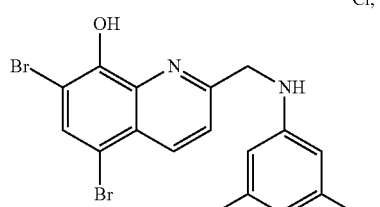
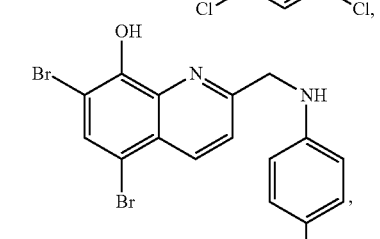
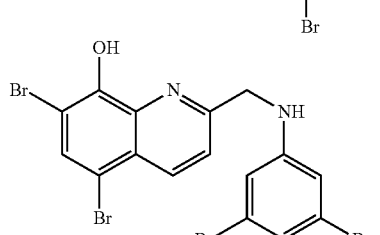
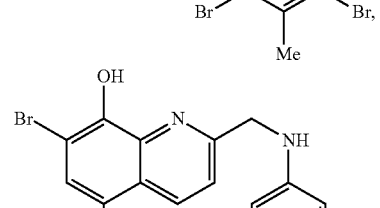
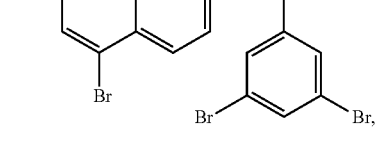
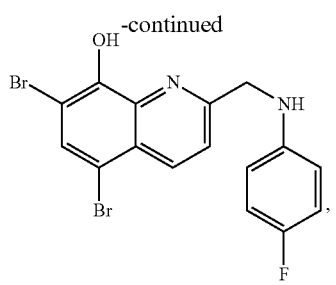
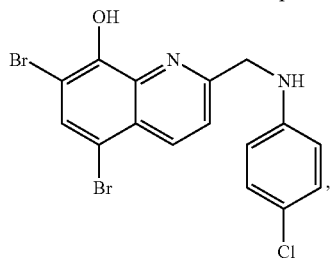
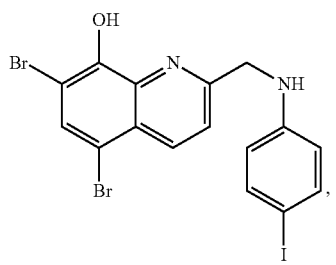
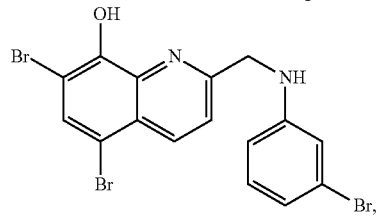
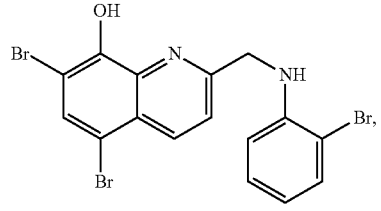
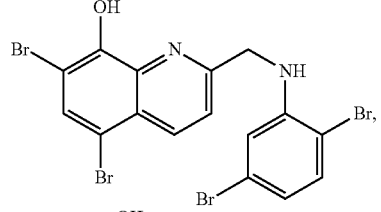
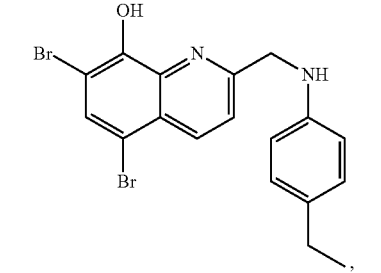

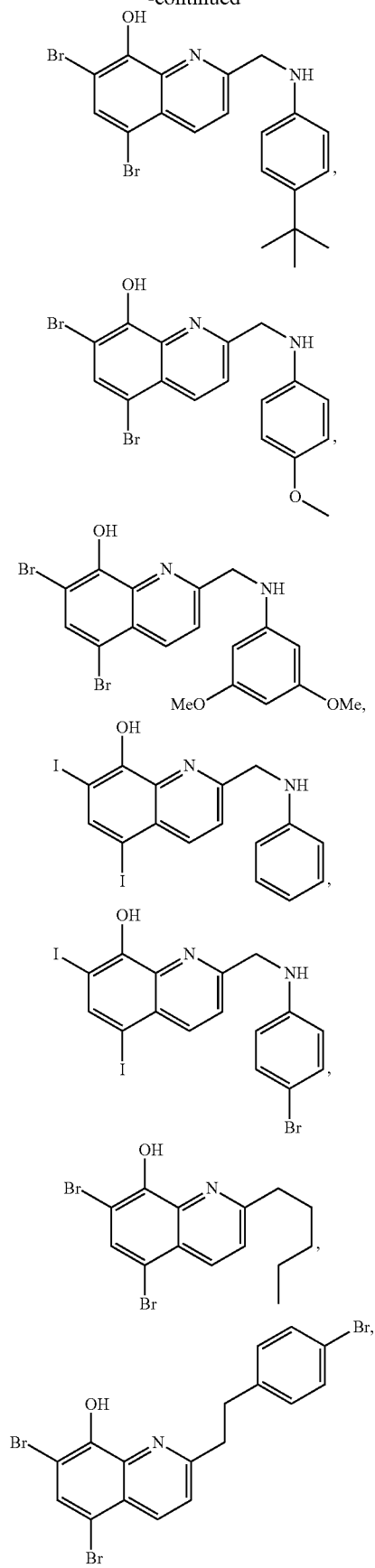
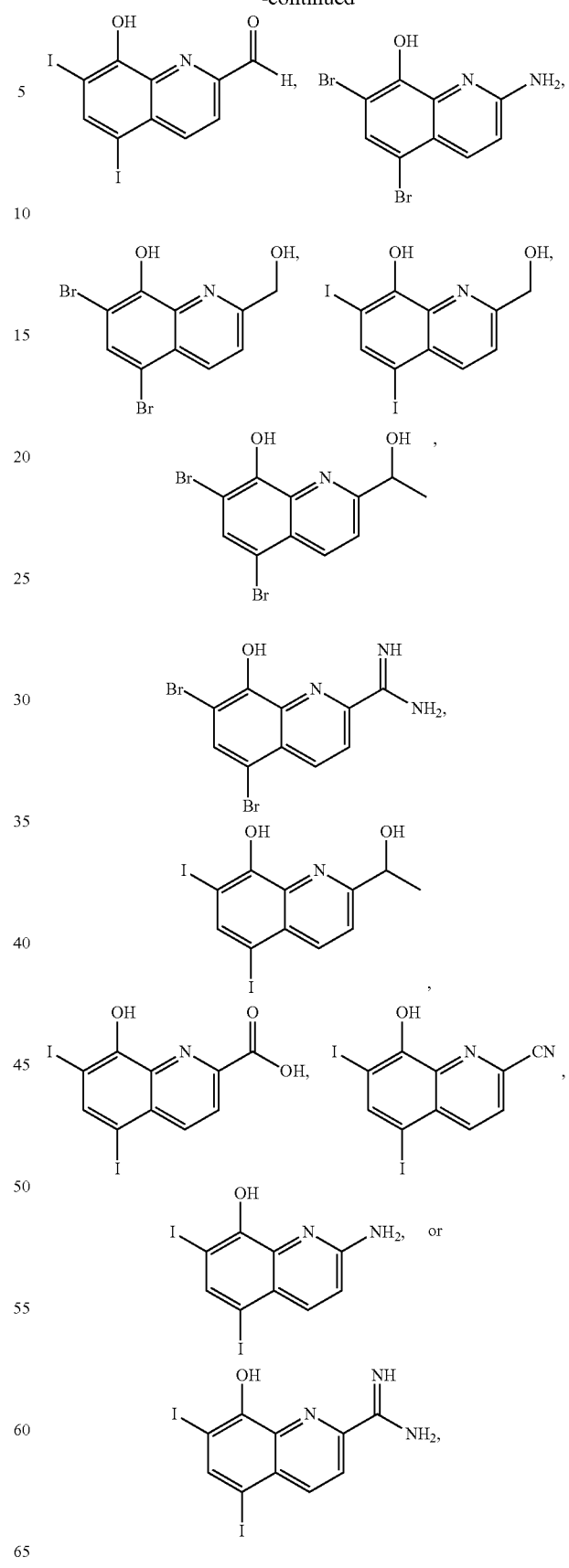
or a pharmaceutically acceptable salt thereof.

14. A method of preparing a compound of claim 1, the method comprising contacting a compound of Formula (B):

(B)

or a salt thereof, with an amine of Formula (C):

$H_2N-R^A$, (C)

or a salt thereof, in the presence of a reductant to provide the compound of claim 1.

15. A composition comprising a compound of claim 1, or a pharmaceutically acceptable salt thereof, and optionally an excipient.

16. A pharmaceutical composition comprising a compound of claim 1, or a pharmaceutically acceptable salt thereof, and optionally a pharmaceutically acceptable excipient.

17. A method of treating a microbial infection in a subject in need thereof, the method comprising administering to the subject an effective amount of a compound of claim 1.

18. A method of inhibiting the growth of reproduction of or killing a microorganism, the method comprising contacting the microorganism with an effective amount of a compound of claim 1.

19. A method of inhibiting the formation or growth of a biofilm, the method comprising contacting the biofilm with an effective amount of a compound of claim 1.

20. A method of disinfecting a surface, the method comprising contacting the surface with an effective amount of a compound of claim 1.

21. The compound of claim 1, wherein the compound is of Formula (I):

(I)

or a pharmaceutically acceptable salt thereof.

22. The compound of claim 1, wherein the compound is of the formula:

or a pharmaceutically acceptable salt thereof.

23. The compound of claim 1, wherein the compound is of the formula:

or a pharmaceutically acceptable salt thereof.

24. The compound of claim 1, or a pharmaceutically acceptable salt thereof, wherein $R^H$ is 25. The compound of claim 1, or a pharmaceutically acceptable salt thereof, wherein $R^H$ is —$CO_2R^L$, -(substituted or unsubstituted $C_{1-6}$-alkylene)-OH, —CN, —$NR^M{}_2$, or 26. The compound of claim 1, or a pharmaceutically acceptable salt thereof, wherein each of $R^E$ and $R^G$ is independently Br or I.

27. The compound of claim 1, wherein the compound is of the formula:

or a pharmaceutically acceptable salt thereof.

28. A method of preventing a microbial infection in a subject in need thereof, the method comprising administering to the subject an effective amount of a compound of claim 1.

* * * * *